US008283505B2

(12) United States Patent
Evanko et al.

(10) Patent No.: US 8,283,505 B2
(45) Date of Patent: *Oct. 9, 2012

(54) RECOVERY OF HIGHER ALCOHOLS FROM DILUTE AQUEOUS SOLUTIONS

(75) Inventors: William A. Evanko, Golden, CO (US); Aharon M. Eyal, Jerusalem (IL); David A. Glassner, Littleton, CO (US); Fudu Miao, Chester Springs, PA (US); Aristos A. Aristidou, Highlands Ranch, CO (US); Kent Evans, Littleton, CO (US); Patrick R. Gruber, Longmont, CO (US); Andrew C. Hawkins, Parker, CO (US)

(73) Assignee: Gevo, Inc., Englewood, CO (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/344,460

(22) Filed: Jan. 5, 2012

(65) Prior Publication Data
US 2012/0107890 A1 May 3, 2012

Related U.S. Application Data

(63) Continuation of application No. 12/342,992, filed on Dec. 23, 2008, now Pat. No. 8,101,808.

(60) Provisional application No. 61/017,141, filed on Dec. 27, 2007, provisional application No. 61/021,495, filed on Jan. 16, 2008, provisional application No. 61/021,558, filed on Jan. 16, 2008, provisional application No. 61/021,567, filed on Jan. 16, 2008.

(51) Int. Cl.
*C07C 29/76* (2006.01)
(52) U.S. Cl. ...................................... 568/916
(58) Field of Classification Search .................. 568/916
See application file for complete search history.

(56) References Cited

U.S. PATENT DOCUMENTS

| 419,332 A | 1/1890 | Horne |
|---|---|---|
| 1,676,700 A | 7/1928 | Lewis |
| 1,860,554 A | 5/1932 | Ricard et al. |
| 2,595,805 A | 5/1952 | Morrell et al. |
| 4,217,178 A | 8/1980 | Katzen et al. |
| 4,251,231 A | 2/1981 | Baird |
| 4,256,541 A | 3/1981 | Muller et al. |
| 4,277,635 A | 7/1981 | Oulman et al. |
| 4,308,109 A | 12/1981 | Griffiths et al. |
| 4,336,335 A | 6/1982 | Muller et al. |
| 4,340,446 A | 7/1982 | Crawford |
| 4,349,628 A | 9/1982 | English et al. |
| 4,359,533 A | 11/1982 | Wilke et al. |
| 4,366,032 A | 12/1982 | Mikitenko et al. |
| 4,381,220 A | 4/1983 | Standiford |
| 4,399,000 A | 8/1983 | Tedder |
| 4,517,298 A | 5/1985 | Tedder |
| 4,520,104 A | 5/1985 | Heady et al. |
| 4,538,010 A | 8/1985 | Diana |
| 4,568,643 A | 2/1986 | Levy |
| 4,628,116 A | 12/1986 | Cenedella |
| 4,654,123 A | 3/1987 | Berg et al. |
| 4,692,432 A | 9/1987 | Tedder |
| 4,703,007 A | 10/1987 | Mulholland et al. |
| 4,777,135 A | 10/1988 | Husted et al. |
| 4,822,737 A | 4/1989 | Saida |
| 4,842,693 A | 6/1989 | Wheldon |
| 4,865,973 A | 9/1989 | Kollerup et al. |
| 5,028,240 A | 7/1991 | Moore et al. |
| 5,030,775 A | 7/1991 | Sircar |
| 5,035,776 A | 7/1991 | Knapp |
| 5,036,005 A | 7/1991 | Tedder |
| 5,063,156 A | 11/1991 | Glassner et al. |
| 5,084,142 A | 1/1992 | Berg et al. |
| 5,085,739 A | 2/1992 | Berg et al. |
| 5,124,004 A | 6/1992 | Grethlein et al. |
| 5,449,440 A | 9/1995 | Rescalli et al. |
| 5,571,387 A | 11/1996 | Marker et al. |
| 5,624,534 A | 4/1997 | Boucher et al. |
| 5,753,474 A | 5/1998 | Ramey |
| 5,795,447 A | 8/1998 | Berg |
| 6,358,717 B1 | 3/2002 | Blaschek et al. |
| 6,753,170 B2 | 6/2004 | Gaddy et al. |
| 6,926,810 B2 | 8/2005 | Cockrem et al. |
| 6,982,026 B2 | 1/2006 | Cockrem et al. |

(Continued)

FOREIGN PATENT DOCUMENTS

BR 0500321-0 A 9/2006
WO WO 2008/076749 6/2008

OTHER PUBLICATIONS

Azeotropic Data, Part I, Gmehling, J; Menke, J; Krafczyk, J; Fischer, K. 2 Cover pages, Introduction, pp. X-XXXVIII, 381-383, 610-611, 619, 624-625, 812-813, 818-819, 831, 837-838, 1001-1002, 1005, 1678-1682, (1994).

Barton et al., "Evaluation of solvents for extractive butanol fermentation with Clostridium acetobutylicum and the use of poly(propylene glycol) 1200," Can. Applied Microbiology and Biotechnology (1992), 36(5), 632-9. CODEN: AMBIDG ISSN: 0175-7598.

Belafi-Bako et al., "Product removal in ethanol and ABE fermentations," Hungarian Journal of Industrial Chemistry (1995), 23(4), 309-19. Publisher: Research Institute of Chemical Engineering, Hungarian Academy of Sciences.

(Continued)

Primary Examiner — Sikarl Witherspoon
(74) Attorney, Agent, or Firm — Cooley LLP

(57) ABSTRACT

This invention is directed to methods for recovery of C3-C6 alcohols from dilute aqueous solutions, such as fermentation broths. Such methods provide improved volumetric productivity for the fermentation and allows recovery of the alcohol. Such methods also allow for reduced energy use in the production and drying of spent fermentation broth due to increased effective concentration of the alcohol product by the simultaneous fermentation and recovery process which increases the quantity of alcohol produced and recovered per quantity of fermentation broth dried. Thus, the invention allows for production and recovery of C3-C6 alcohols at low capital and reduced operating costs.

18 Claims, 2 Drawing Sheets

U.S. PATENT DOCUMENTS

| | | |
|---|---|---|
| 6,984,293 B2 | 1/2006 | Cockrem et al. |
| 7,074,603 B2 | 7/2006 | Verser et al. |
| 7,125,474 B2 | 10/2006 | Beckmann et al. |
| 7,141,707 B2 | 11/2006 | Beckmann et al. |
| 7,144,977 B2 | 12/2006 | Eyal et al. |
| 7,196,218 B2 | 3/2007 | Gaddy et al. |
| 7,297,236 B1 | 11/2007 | Vander Griend |
| 7,851,188 B2 | 12/2010 | Donaldson et al. |
| 7,993,889 B1 | 8/2011 | Donaldson et al. |
| 8,101,808 B2 | 1/2012 | Evanko et al. |
| 2005/0089979 A1 | 4/2005 | Ezeji et al. |
| 2005/0132741 A1 | 6/2005 | Roth et al. |
| 2007/0031954 A1 | 2/2007 | Mairal et al. |
| 2007/0092957 A1 | 4/2007 | Donaldson et al. |
| 2008/0015395 A1 | 1/2008 | D'Amore et al. |
| 2008/0045754 A1 | 2/2008 | D'Amore et al. |
| 2008/0124774 A1 | 5/2008 | Bramucci et al. |
| 2008/0132741 A1 | 6/2008 | D'Amore et al. |
| 2008/0274526 A1 | 11/2008 | Bramucci et al. |
| 2009/0171129 A1 | 7/2009 | Evanko et al. |

OTHER PUBLICATIONS

Card et al., "Separation of Alcohol- Water Mixtures Using Salts," Oak Ridge National Laboratory. Apr. 1982.

Chiueh et al., "Production of acetone-butanol from cellulosic materials. II. Acetone-butanol fermentation of pentoses, glucose and cellobiose," Zhongguo Nongye Huaxue Huizhi (1986), 24(4), 366-75. English translated abstract only provided.

Dadgar et al., "Improving the acetone-butanol fermentation process with liquid-liquid extraction," Biotechnology Progress (1988), 4(1), 36-9. CODEN: BIPRET ISSN: 8756-7938.

Daugulis, "Integrated fermentation and recovery processes," Current opinion in biotechnology (1994), 5(2), 192-5.

Duerre et al., "Acetone-butanol fermentation basis of a modern biotechnological process?" Chemie Ingenieur Technik (1992), 64(6), 491-8. (Translated Abstract).

Durre et al., "New insights and novel developments in clostridial acetone/butanol/isopropanol fermentation," Applied Microbiology and Biotechnology (1998), 49(6), 639-648.

Ennis et al., "The acetone-butanol-ethanol fermentation: a current assessment," Process Biochemistry (Rickmansworth, United Kingdom) (1986), 21(5), 131-47.

Etude De L'Equilibre Vapeur Du Melange Eau-Isobutanol, Phys. Chem. News 12 (2003) 118-122, H. Mazouz, M. Tahiri, A. Kossir.

Ezeji et al. "Butanol fermentation research: Upstream and downstream manipulations." Biotechnology & Bioengineering Group, Department of Food Science & Human Nutrition, University of Illinois, Urbana, IL, USA. Chemical Record (2004), 4(5), 305-314. Publisher: John Wiley & Sons, Inc., CODEN: CRHEAK ISSN: 1527-8999. Journal; General Review.

Ezeji et al., "Bioproduction of butanol from biomass: from genes to bioreactors," Current Opinion in Biotechnology (2007), 18(3), 220-227. Publisher: Elsevier Ltd.

Ezeji et al., "Butanol production from agricultural residues: impact of degradation products on Clostridium beijerinckii growth and butanol fermentation," Biotechnology and Bioengineering (2007), 97(6), 1460-1469. Publisher: John Wiley & Sons, Inc.

Ezeji et al., "Continuous butanol fermentation and feed starch retrogradation: butanol fermentation sustainability using Clostridium beijerinckii BA 101," Journal of Biotechnology (2005), 115(2), 179-187.

Ezeji et al., "Industrially relevant fermentations," Handbook on Clostridia (2005), 797-812.

Ezeji et al., "Production of butanol from corn," Chemical Industries (Boca Raton, FL, United States) (2006), 112(Alcoholic Fuels), 99-122.

Fay et al., "Improving Vacuum Systems", Chemical Engineering, Sep. 2000,86-91.

Gapes et al., "The history of the acetone-butanol project in Austria," Journal of molecular microbiology and biotechnology (2000), 2(1), 5-8.

Gapes, "The economics of acetone-butanol fermentation: theoretical and market considerations," Journal of Molecular Microbiology and Biotechnology (2000), 2(1), 27-32.

Garcia et al., "Butanol fermentation liquor production and separation by reverse osmosis," Biotechnology and Bioengineering (1986), 28(6), 785-91.

Garcia et al., "Butanol fermentation liquor separation by reverse osmosis," Avail. Univ. Microfilms Int., Order No. DA8512211. (1984), 121 pp. From: Diss. Abstr. Int. B 1985, 46(4), 1251.

Geng et al., "Extractive butanol fermentation using pervaporation and a low acid producing Clostridium acetobutylicum B18," Nonmunjip—Sekye Hanminchok Kwahak Kisulcha Jonghap Haksul Taehoe: Kobunja, Chaelyo, Hwakong Punkwa (1993), 1431-5, English translated abstract only provided.

Geng et al., "Pervaporative butanol fermentation by Clostridium acetobutylicum B18," Biotechnology and Bioengineering (1994), 43(10), 978-86.

Groot et al., "3. Integration of pervaporation and continuous butanol fermentation with immobilized cells. II: Mathematical modelling and simulations," Chemical Engineering Journal Amsterdam, Netherlands) (1991), 46(1), B11-B19. CODEN: CMEJAJ ISSN: 0300-9467.

Groot et al., "4. Integration of pervaporation and continuous butanol fermentation with immobilized cells. I: Experimental results," Chemical Engineering Journal (Amsterdam, Netherlands) (1991), 46(1), B1-B10. CODEN: CMEJAJ ISSN: 0300-9467.

Groot et al., "Batch and continuous butanol fermentations with free cells: integration with product recovery by gas-stripping," Applied Microbiology and Biotechnolog, 32, 305-308, 1989.

Hu et al., "Preliminary study on coupling between biodiesel oil and acetone-butanol fermentation," Shengwu Jiagong Guocheng (2007), 5(1), 27-32. Publisher: Nanjing Gongye Daxue Shengwu Jiagong Guocheng Bianjibu, CODEN: SJGHB9 ISSN: 1672-3678. Journal written in Chinese. English translated abstract only provided.

Huesing et al., "Biotechnological production of value-added substances from industrial waste streams with special reference to energy carriers and biopolymers," Systemtechnik und Innovationsforschung, Fraunhofer-Institut, Karlsruhe, Germany. Texte—Umweltbundesamt (2003), (64), i-xviii, a/1-a/22, 1-263. Publisher: Umweltbundesamt, written in German. English translated abstract only provided.

International Search Report for International (PCT) Application No. PCT/US08/88187, mailed May 20, 2009.

Ishii et al., "Acetone and butanol production by extraction fermentation,". Kemikaru Enjiniyaringu (1985), 30(2), 113-17. written in Japanese. English translated abstract only provided.

Jeon et al., "In situ product recovery in butanol fermentation by a novel membrane-assisted extraction," Auburn Univ., Auburn, AL, USA. Avail. Univ. Microfilms Int., Order No. DA8918800. (1988), 244 pp. From: Diss. Abstr. Int. B 1989, 50(5), 2052.

Jeon et al., "Mathematical modeling and simulation of the membrane-extractive butanol fermentation," Hwahak Konghak (1989), 27(4), 451-8. CODEN: HHKHAT ISSN: 0304-128X. Journal written in Korean. English translated abstract only provided.

Jeon et al., "Membrane-assisted extractive butanol fermentation," Annals of the New York Academy of Sciences (1987), 506(Biochem. Eng. 5), 536-42.

Jeon et al., (1989), "In situ product separation in butanol fermentation by membrane-assisted extraction," Enzyme Microb. Technol., 11, 575-582.

Jones et al., "Acetone-butanol fermentation revisited," Microbiological Reviews (1986), 50(4), 484-524.

Jones et al., "Applied acetone-butanol fermentation," Clostridia (2001), 125-168. Publisher: Wiley-VCH Verlag GmbH, Weinheim, Germany.

Karakashev et al., "Anaerobic biotechnological approaches for production of liquid energy carriers from biomass," Biotechnology Letters (2007), 29(7), 1005-1012.

Ladisch, "Fermentation-derived butanol and scenarios for its uses in energy-related applications," Enzyme and Microbial Technology (1991), 13(3), 280-3.

Larsson et al., "Butanol fermentation using a selective adsorbent for product recovery," Eur. Congr. Biotechnol., 3rd (1984), 2 313-16.

Leeper, "Membrane separations in the recovery of biofuels and biochemicals: an update review," Sep. Purif. Technol. (1992), 99-194. Publisher: Dekker, New York, N.Y. English abstract only provided.

Letcher et al., "Ternary Phase Diagrams for Gasoline-Water-Alcohol Mixtures," Fuel, Jul. 1986, vol. 65, Issue 7, pp. 891-894.

Li et al., "Development of integrated biological reaction and separation process of products," Huaxue Jinzhan (1997), 9(3), 283-290. Publisher: Zhongguo Kexueyuan Wenxian Qingbao Zhongxin Chubanbu, written in Chinese (English Abstract).

Liu et al., "Separation of aceton-butanol-ethanol (ABE) from dilute aqueous solutions by pervaporation," Separation and Purification Technology, 42, 273-282, (2005).

Maddox et al., "Application of membrane processes to product recovery from ABE fermentation," Australasian Biotechnology (1993), 3(3), 138-42.

Maddox, "The acetone-butanol-ethanol fermentation: recent progress in technology," Biotechnology & Genetic Engineering Reviews (1989), 7 189-220.

Mariano et al., "Optimization Strategies Based on Sequential Quadratic programming Applied for a Fermentation Process for Butanol Production.," Applied Biochem Biotechnology, Dec. 11, 2008.

Marlatt and Datta, "Acetone-butanol fermentation process development and economic evaluation" Biotechnology Progress, 2(1), 23-28 (1986).

Mollah, "Feasability of in situ fas stripping for continuous acetone-butanol fermentation by clostriduium acetobutylicum," Enzyme Microb. Technol., 15,200-207, 1993.

Nielsen et al., "Adsorbents for extractive bioconversion applied to the acetone-butanol fermentation," Applied Microbiology and Biotechnology (1988), 28(4-5), 335-9.

Nimcevic et al., "The acetone-butanol fermentation in pilot plant and pre-industrial scale," Journal of Molecular Microbiology and Biotechnology (2000), 2(1), 15-20.

Ohno et al., "Extractive butanol fermentation combined with membrane separation," Proceedings of Symposium on Solvent Extraction (1991), 265-72. CODEN: PSEXEC. Abstract only provided.

Park et al., "Mathematical modeling of fed-batch butanol fermentation with simultaneous pervaporation," Korean Journal of Chemical Engineering (1996), 13(6), 612-619.

Park et al., "Simultaneous fermentation and separation in the ethanol and ABE fermentation," Separation and Purification Methods (1992), 21(2), 127-17.

Pozderovic et al., "Concentration of aqueous solutions of organic componenets by reverse osmosis. Influeunce of transmembrane pressure and membrane type on concentration of different alcohol solutions by reverse osmosis," Journal of Food Engineering, vol. 77 (2006) 810-817.

Qureshi et al., "Butanol production from agricultural biomass," Food Science and Technology (Boca Raton, FL, United States) (2006), 148(Food Biotechnology (2nd Edition)), 525-549.

Qureshi et al., "Butanol Production from Corn Fiber Xylan Using Clostridium acetobutylicum," Biotechnology Progress (2006), 22(3), 673-680.

Qureshi et al., "Butanol recovery from model solution/fermentation broth by pervaporation: evaluation of membrane performance," Biomass and Bioenergy (1999), 17(2), 175-184.

Qureshi et al., "Energy-efficient recovery of butanol from model solutions and fermentation broth by adsorption," Bioprocess and biosystems engineering (2005), 27(4), 215-22.

Qureshi et al., "Evaluation of recent advances in butanol fermentation, upstream and downstream processing," Bioprocess and Bissystems Engineering, 219-226, 2001.

Qureshi et al., "Production of acetone butanol ethanol (ABE) by a hyper-producing mutant strain of Clostridium beijerinckii BA101 and recovery by pervaporation," Biotechnology progress (1999), 15(4), 594-602.

Qureshi et al., "Recent advances in ABE fermentation: hyper-butanol producing Clostridium beijerinckii BA101," Journal of Industrial Microbiology & Biotechnology (2001), 27(5), 287-291.

Qureshi et al., "Recovery of butanol from fermentation broth by gas stripping," Renewable Energy (2000), Volume Date 2001, 22(4), 557-564. Publisher: Elsevier Science Ltd.

Qureshi et al., "Reduction in butanol inhibition by perstraction: Utilization of concentrated lactose/whey permeate by Clostridium acetobutylicum to enhance butanol fermentation economics," Food and Bioproducts Processing (2005), 83(C1), 43-52.

Qureshi et al., "Soy molasses as fermentation substrate for production of butanol using Clostridium beijerinckii BA 101," Journal of Industrial Microbiology & Biotechnology (2001), 26(5), 290-295. Publisher: Nature Publishing Group.

Santangelo et al., "Microbial production of acetone and butanol: can history be repeated?" Chimica Oggi (1996), 14(5), 29-35, Abstract only provided.

Schuster, "Applied acetone-butanol fermentation," Molecular Microbiology and Biotechnology (2000), 2(1), 3-4. Publisher: Horizon Scientific Press.

Stichlmair et al., "Separation of Azeotropic Mixtures via Enhanced Distillation," Chemical Engineering Progress, Jan. 1989, pp. 16-20.

Stockhardt et al., "Vapor-Liquid Equilibria and Boiling-Point composition Relatons for Systems n-Butanol-Water and Isobutanol-Water," Industrial and Engineering Chemistry. vol. 23, No. 12, Dec. 1931.

Tashiro et al., "Development of biomass utilization by acetone-butanol-ethanol fermentation," Baiosaiensu to Indasutori (2003), 61(8), 544-547. Publisher: Baioindasutori Kyokai, written in Japanese (English Abstract).

Tatani et al., "Alcohol production by extractive fermentation," Hakko Kogaku Kaishi (1985), 63(5), 463-5. written in Japanese. English abstract only provided.

Taya et al., "Acetone-butanol fermentation with a combined process of fermentation and extraction," Kagaku Sochi (1986), 28(5), 87-91. CODEN: KASOB7 ISSN: 0368-4849. Journal; General Review written in Japanese. English abstract only provided.

Vane, "Review: A review of pervaporation for product recovery from biomass fermentation processes," J. Chem. Technol. Biotechnol. 2005, 80:603-629.

Written Opinion for International (PCT) Application No. PCT/US08188187, mailed May 20, 2009.

Yang et al., "Enhanced acetone-butanol fermentation using repeated fed-batch operation coupled with cell recycle by membrane and simultaneous removal of inhibitory products by adsorption," Biotechnology and Bioengineering (1995), 47(4), 444-50.

Yang et al., "Enhancement of in situ adsorption on the acetone-butanol fermentation by Clostridium acetobutylicum," Separations Technology (1994), 4(2), 81-92.

Yang et al., "Study on acetone/butanol fermentation with in situ solvent extraction," Zhejiang Daxue Xuebao, Ziran Kexueban (1992), 26(4), 388-98,387. CODEN: ZDXKE5 ISSN: 0253-9861. Journal written in Chinese. English abstract only provided.

Yiamsombat et al., "Production of butanol fermentation and increasing butanol concentration by reverse osmosis," Microbial Utilization of Renewable Resources (1991), Volume Date 1990, 7 544-50.

Zverlov et al., "Bacterial acetone and butanol production by industrial fermentation in the Soviet Union: use of hydrolyzed agricultural waste for biorefinery," Applied microbiology and biotechnology (2006), 71(5), 587-97.

"Request for Inter Partes Reexamination of U.S. Patent No. 8,101,808 Under 35 U.S.C. § 311 and 37 C.F.R. § 1.913," 146 pages, U.S. Appl. No. 95/000,666 (filed May 7, 2012).

"Declaration of Dr. Andrew J. Daugulis," 107 pages, Appendix I to Request for Inter Partes Reexamination of U.S. Patent No. 8,101,808 (May 7, 2012).

"Appendices II to CXI," 810 pages, filed as part of Request for Inter Partes Reexamination of U.S. Patent No. 8,101,808 (May 7, 2012).

Willaim A. Evanko et al., U.S. Appl. No. 61/017,141, 53 pages, filed Dec. 27, 2007 (Exhibit B of Request for Inter Partes Reexamination of U.S. Patent No. 8,101,808).

Willaim A. Evanko et al., U.S. Appl. No. 61/021,495, 55 pages, filed Jan. 16, 2008 (Exhibit C of Request for Inter Partes Reexamination of U.S. Patent No. 8,101,808).

Willaim A. Evanko et al., U.S. Appl. No. 61/021,558, 56 pages, filed Jan. 16, 2008 (Exhibit D of Request for Inter Partes Reexamination of U.S. Patent No. 8,101,808).

Willaim A. Evanko et al., U.S.Appl. No. 61/021,567, 57 pages, filed Jan. 16, 2008 (Exhibit E of Request for Inter Partes Reexamination of U.S. Patent No, 8,101,808).

Select papers from U.S. Appl. No. 12/342,992, now U.S. Patent No. 8,101,808 B2, 40 pages (Exhibit F of Request for Inter Partes Reexamination of U.S. Patent No. 8,101,808).

English Translation of BR PI 0500321-0 A, published Sep. 16, 2006, Universidade Estadual de Campinas- UNICAMP (BR/SP). (Exhibit L of Request for Inter Partes Reexamination of U.S. Patent No. 8,101,808).

Lu, X., et al., "Salting-Out Separation and Liquid-Liquid Equilibrium of Tertiary Butanol Aqueous Solution," Chemical Engineering Journal, 78:165-171 (2000). (Exhibit O of Request for Inter Partes Reexamination of U.S. Patent No. 8,101,808).

Freier, D., et al., "Characterization of Clostridium thermocellum JW20," Applied and Environmental Microbiology, 54:204-211 (1998). (Exhibit P of Request for Inter Partes Reexamination of U.S. Patent No. 8,101,808).

Maiorella, B., et al., "Low-Cost, Low-Energy Flash Ethanol Fermentation," Energy and Environmental Division, annual report, 1979, p. 4-9 to 4-14 (1980). (Exhibit Q of Request for Inter Partes Reexamination of U.S. Patent No. 8,101,808).

Shi, Z., et al., "Performance Evaluation of Acetone-Butanol Continuous Flash Fermentation," Bioprocess Biosystems Engineering, 27:175-183 (2005). (Exhibit R of Request for Inter Partes Reexamination of U.S. Patent No. 8,101,808).

Abouzied, M., et al., "Fermentation of Starch to Ethanol by a Complementary Mixture of Amylolytic Yeast and Saccharomyces cerevisiae," Biotechnology Letters, 9:59-62 (1987). (Exhibit U of Request for Inter Partes Reexamination of U.S. Patent No. 8,101,808).

Hess, G., "BP and DuPont Plan 'Biobutanol'," Chemical and Engineering News, p. 9, published Jun. 26, 2006. (Exhibit W of Request for Inter Partes Reexamination of U.S. Patent No. 8,101,808).

"Office Action Summary," U.S. Appl. No. 12/824,050, 22 pages, mailed Feb. 15, 2012 (Exhibit Y of Request for Inter Partes Reexamination of U.S. Patent No. 8,101,808).

"Complaint," *Gevo, Inc.* v. *Butamax*™ Advanced Biofuels LLC and E.I. Dupont De Nemours and Co., 1:12-cv-00070-SLR, United States District Court for the District of Delaware (filed Jan. 24, 2012).

"Answer," *Gevo, Inc.* v. *Butamax*™ Advanced Biofuels LLC and E.I. Dupont De Nemours and Co., 1:12-cv-00070-SLR, United States District Court for the District of Delaware (filed Mar. 9, 2012).

"Office Action in Inter Partes Reexamination," 65 pages, U.S. Appl. No. 95/000,666 (mailed Jul. 18, 2012).

"Order Granting/Denying Request for Inter Partes Reexamination," 20 pages, U.S. Appl. No. 95/000,666 (mailed Jul. 18, 2012).

Schematic Diagram of the continuous vacuum flashing process for isobutanol recovery.

RECOVERY OF HIGHER ALCOHOLS FROM DILUTE AQUEOUS SOLUTIONS

CROSS REFERENCE TO RELATED APPLICATIONS

This application is a continuation of U.S. patent application Ser. No. 12/342,992, filed Dec. 23, 2008 now U.S. Pat. No. 8,101,808, which claims priority to U.S. Provisional Application Ser. No. 61/017,141 filed Dec. 27, 2007; 61/021,495 filed Jan. 16, 2008; 61/021,558 filed Jan. 16, 2008 10 and 61/021,567 filed Jan. 16, 2008. Accordingly, this application incorporates by reference in their entireties each of the above-referenced applications for all purposes.

FIELD OF THE INVENTION

This application relates generally to methods for recovery of C3-C6 alcohols from dilute aqueous solutions, such as fermentation broths.

BACKGROUND OF THE INVENTION

Biofuels have a long history ranging back to the beginning of the 20th century. As early as 1900, Rudolf Diesel demonstrated at the World Exhibition in Paris, France, an engine running on peanut oil. Soon thereafter, Henry Ford demonstrated his Model T running on ethanol derived from corn. Petroleum-derived fuels displaced biofuels in the 1930s and 1940s due to increased supply, and efficiency at a lower cost.

Market fluctuations in the 1970s, due the Arab oil embargo and the Iranian revolution, coupled to the decrease in US oil production, led to an increase in crude oil prices and a renewed interest in biofuels. Today, many interest groups, including policy makers, industry planners, aware citizens, and the financial community, are interested in substituting petroleum-derived fuels with biomass-derived biofuels. The leading motivation for developing biofuels is of economical nature, namely, the threat of 'peak oil', the point at which the consumption rate of crude oil exceeds the supply rate, thus leading to significantly increased fuel cost results in an increased demand for alternative fuels.

Biofuels tend to be produced with local agricultural resources in many, relatively small facilities, and are seen as a stable and secure supply of fuels independent of geopolitical problems associated with petroleum. At the same time, biofuels enhance the agricultural sector of national economies. In addition, since fossil sources of fuels take hundreds of millions of years to be regenerated and their use increases carbon dioxide levels in the atmosphere, leading to climate change concerns, sustainability is an important social and ethical driving force which is starting to result in government regulations and policies such as caps on carbon dioxide emissions from automobiles, taxes on carbon dioxide emissions, and tax incentives for the use of biofuels.

The acceptance of biofuels depends primarily on economical competitiveness of biofuels when compared to petroleum-derived fuels. Biofuels that cannot compete in cost with petroleum-derived fuels will be limited to specialty applications and niche markets. Today, the use of biofuels is limited to ethanol and biodiesel. Currently, ethanol is made by fermentation from corn in the US, sugar cane in Brazil, and other grains worldwide. Ethanol is competitive with petroleum-derived gasoline, exclusive of subsidies or tax benefits, if crude oil stays above $50 per barrel. Biodiesel has a breakeven price of crude oil of over $60/barrel to be competitive with petroleum-based diesel (Nexant Chem Systems, 2006, Final Report, Liquid Biofuels: Substituting for Petroleum, White Plains, N.Y.).

Several factors influence the core operating costs of a carbohydrate based biofuel source. In addition to the cost of the carbon-containing, plant produced raw material, a key factor in product economic costs for ethanol or other potential alcohol based biofuels, such as butanol, is the recovery and purification of biofuels from aqueous streams. Many technical approaches have been developed for the economic removal of alcohols from aqueous based fermentation media. The most widely used recovery techniques today use distillation and molecular sieve drying to produce ethanol. For example, butanol production via the Clostridia-based acetone-butanol-ethanol fermentation also relied on distillation for recovery and purification of the products. Distillation from aqueous solutions is energy intensive. For ethanol, additional processing equipment to break the ethanol/water azeotrope is required. This equipment, molecular sieves, also uses significant quantities of energy.

Many unit operations have been studied for the recovery and purification of fermentation produced alcohols, including filtration, liquid/liquid extraction, membrane separations (e.g., tangential flow filtration, pervaporation, and perstraction), gas stripping, and "salting out" of solution, adsorption, and absorption. Each of the approaches has advantages and disadvantages depending on the circumstances of the product to be recovered and the product's physical and chemical properties and the matrix in which it resides.

Variables which control the production costs of biofuels can be characterized as those impacting operating costs, capital costs, or both. Typically, key variables that control fermentation economic performance include carbohydrate yield to desired product, product concentration and volumetric productivity. All three key variables, yield, product concentration, and volumetric productivity, impact both capital and operating costs.

As product yield on carbohydrate fermented is increased, the production costs for a given unit of product decrease linearly relative to raw material costs. The product yield on carbohydrate also impacts equipment size, capital expenditures, utilities consumption and feed stock preparation materials such as enzymes, minerals, nutrients (vitamins), and water. For example an increase in product yield on glucose to butanol from 50% to 90% of theoretical results in a 44% decrease in direct operating costs. Also, the increased yield of 90% reduces the amount of raw materials handled and processed. The increased yield directly reduces capital investment required for the production facility as all equipment from carbohydrate preparation through purification and recovery are reduced in size. Equipment, piping, and utility requirements can be reduced by 32% if yield is increased from 50% to 90%. The direct influence of product yield on production costs makes it a key influence on the cost and market viability for biofuels. An approach to increase product yield involves Genetically Engineered Microorganisms (GEMs) that can be constructed to manipulate the organism's metabolic pathway to reduce or eliminate undesired products, increase the efficiency of the desired metabolite or both. This allows for the deletion of one or both of low cost products and undesired products, which increases production of desired products.

For example, US Patent Application Publication 2005/0089979 discloses a fermentation process that utilizes a *Clostridium beijerinckii* microorganism that produces a mixture of products including 5.3 g/L acetone, 11.8 g/L, butanol, and 0.5 g/L ethanol. An appropriately modified Genetically Engineered Microorganism eliminates acetone and ethanol production while increasing conversion of carbohydrates to butanol. The redirection of a carbohydrate feedstock away from ethanol and acetone to butanol increases butanol production from 11.8 g/L to 18.9 g/L, a 60% increase in butanol production relative to carbohydrate consumption. The elimination of the ethanol and acetone byproducts also allows for reduced capital costs as less equipment is necessary to complete recovery and purification.

Application of biochemical tools, including, genetic engineering and classical strain development can also impact the final product concentration (g/L) and fermentation volumetric productivity (g/L-hr) of the biocatalyst. Final product concentration and volumetric productivity impacts several aspects of product economics, including equipment size, raw material use, and utility costs. As the tolerable product concentration increases in the fermentation, recovery volumes of aqueous solutions are decreased which results in reduced capital costs and smaller volumes of materials to process within the production facility.

Volumetric productivity directly impacts the required fermentor capacity to achieve the same product output. For example, a traditional *Clostridium beijerinckii* acetone-butanol-ethanol (ABE) fermentation produces a ratio of acetone, butanol, and ethanol. Genetically engineered microbes allow the designed production of a single product, such as n-butanol, isobutanol or 2-butanol (Donaldson et al., U.S. patent application Ser. No. 11/586,315). Butanol tolerant hosts can be identified utilizing techniques to identify and enhance the butanol tolerance (Bramucci et al., U.S. patent application Ser. No. 11/743,220). These two techniques can then be combined to produce butanol at commercially relative concentrations, and volumetric productivity.

The utilization of GEMs to increase product volumetric productivity and concentration may strongly influence product economics. For example, a butanol fermentation completed at twice the volumetric productivity will reduce fermentor cost by almost 50% for a large industrial biofuels fermentation facility. The fermentor capital cost and size reduction decreases depreciation and operating costs for the facility. Similarly, if the GEMs result in an organism that is tolerant to higher butanol concentrations, operating and capital costs are reduced for a given production volume. For example, if a wild type strain is capable of tolerating 20 g/L butanol and a corresponding genetically improved or genetically enhanced microorganism tolerates 40 g/L butanol, the water load in the fermentor broth volume handled in downstream recovery and purification equipment is reduced by half. In this example, the doubling of product concentration in the fermentation broth almost halves the amount of water to be recovered and processed in recovery unit operations.

A large number of minor cost components also impact operating and capital costs for biofuels production. Example factors that can impact fermentation include, but are not limited to, chemical additives, pH control, surfactants, and contamination are some of the factors but many additional factors can impact fermentation product cost.

SUMMARY OF THE INVENTION

In one embodiment, the present invention provides a method to recover a C3-C6 alcohol from a fermentation broth containing microorganisms and the C3-C6 alcohol. The method includes the step of increasing the activity of the C3-C6 alcohol in a portion of the fermentation broth to at least that of saturation of the C3-C6 alcohol in the portion. Alternatively, the method may include the step of decreasing the activity of water in a portion of the fermentation broth to at least that of saturation of the C3-C6 alcohol in the portion. The method also includes the step of forming a C3-C6 alcohol-rich liquid phase and a water-rich liquid phase from the portion of the fermentation broth. The method also includes the step of separating the C3-C6 alcohol-rich phase from the water-rich phase.

In another embodiment, the present invention provides a method to produce a C3-C6 alcohol. The method includes the step of culturing a microorganism in a fermentation medium to produce the C3-C6 alcohol. The method also includes the step of increasing the activity of the C3-C6 alcohol in a portion of the fermentation medium to at least that of saturation of the C3-C6 alcohol in the fermentation medium. The method also includes the step of forming a C3-C6 alcohol-rich liquid phase and a water-rich phase from the portion of the fermentation medium. The method also includes the step of separating the C3-C6 alcohol-rich phase from the water-rich phase. The method also includes the step of conducting the water rich phase to the fermentation medium.

In another embodiment, the present invention provides a method to produce a C3-C6 alcohol. The method includes hydrolyzing a feedstock comprising a polysaccharide and at least one other compound to produce fermentable hydrolysis products. The method also includes fermenting at least a portion of the fermentable hydrolysis products in a fermentation medium to produce the C3-C6 alcohol, wherein the fermentation medium further includes at least one non-fermented compound. The method also includes increasing the activity of the C3-C6 alcohol from a portion of the fermentation medium to at least that of saturation of the C3-C6 alcohol in the fermentation medium. The method also includes forming a C3-C6 alcohol-rich liquid phase and a water-rich phase from the portion of the fermentation medium. The method also includes separating the C3-C6 alcohol-rich phase from the water-rich phase. The method also includes separating the at least one non-fermented compound from the fermentation medium, the water-rich phase or both. In some embodiments, the step of hydrolyzing a feedstock includes saccharification. In some embodiments, at least two of the steps of hydrolyzing, fermenting and increasing the activity of the C3-C6 alcohol are conducted simultaneously for at least a portion of time. In some embodiments, the step of fermenting is conducted with a microorganism that is capable of hydrolyzing the feedstock.

In another embodiment, the present invention provides a method to produce a product from a C3-C6 alcohol in a fermentation broth including microorganisms and the C3-C6 alcohol. The method includes the steps of distilling a vapor phase comprising water and C3-C6 alcohol from the fermentation broth and reacting the C3-C6 alcohol in the vapor phase to form the product. In some embodiments, the C3-C6 alcohol is propanol and the ratio of the C3-C6 alcohol to water in the vapor phase is greater than about 0.2 (w/w). In some embodiments, the C3-C6 alcohol is butanol and the ratio of the C3-C6 alcohol to water in the vapor phase is greater than about 1 (w/w). In some embodiments, the C3-C6 alcohol is pentanol and the ratio of the C3-C6 alcohol to water in the vapor phase is greater than about 4 (w/w). In some embodiments, the step of reacting is in the presence of a catalyst. In some embodiments, the catalyst is a heterogeneous catalyst.

In another embodiment, the present invention provides a method to produce a C3-C6 alcohol. This method includes the steps of culturing a microorganism in a fermentation medium to produce the C3-C6 alcohol. This method also includes the step of increasing the activity of the C3-C6 alcohol in a portion of the fermentation medium. The method also includes the step of distilling the portion of the fermentation medium to produce a vapor phase that includes water and C3-C6 alcohol and a liquid phase, and the step of conducting the liquid phase to the fermentation medium.

In another embodiment, the present invention provides a method to recover a C3-C6 alcohol from a dilute aqueous solution that includes a first amount of the C3-C6 alcohol. The method includes distilling a portion of the dilute aqueous solution to a vapor phase containing C3-C6 alcohol and water, wherein the vapor phase contains between about 1% by weight and about 45% by weight of the first amount of C3-C6 alcohol from the portion of the dilute aqueous solution. The method further includes condensing the vapor phase. In various embodiments, the vapor phase may contain between about 2% by weight and about 40%, between about 3% by weight and about 35%, between about 4% by weight and about 30%, or between about 5% by weight and about 25% by weight of the C3-C6 alcohol from the dilute aqueous solution. In some embodiments, the method includes forming a C3-C6 alcohol-rich liquid phase and a water-rich liquid phase from the condensed vapor phase. In some embodiments, the method includes separating the C3-C6 alcohol-rich phase and the water-rich phase. In some embodiments, the step of distilling is a single stage distillation. The distilling may be adiabatic or isothermal. In various embodiments, the enrichment of alcohol from the dilute aqueous solution to the condensed vapor may be at least about 5 fold, at least about 10 fold or at least about 15 fold.

In another embodiment, the present invention provides a method to operate a retrofit ethanol production plant. In some embodiments, the retrofit plant includes a pretreatment unit, multiple fermentation units, and a beer still to produce a C3-C6 alcohol. The method includes pretreating a feedstock to form fermentable sugars in the pretreatment unit. The method also includes culturing a microorganism in a fermentation medium comprising the fermentable sugars in a first fermentation unit to produce the C3-C6 alcohol. The method also includes treating a portion of the fermentation medium comprising the C3-C6 alcohol to remove a portion of the C3-C6 alcohol. The method also includes returning the treated portion of the fermentation medium to the first fermentation unit. The method also includes transferring the fermentation medium from the first fermentation unit to the beer still. In various embodiments, the C3-C6 alcohol output of the retrofit plant is at least about 80%, at least about 90%, or at least about 95% of the C3-C6 alcohol equivalent of the ethanol maximum output of the plant before retrofit.

In another embodiment, the present invention provides a method for extraction of a C3-C6 alcohol from an aqueous solution. The method includes contacting the aqueous solution with an acidic, amine-based alcohol-selective extractant. In some embodiments, two phases form after the step of contacting. In some embodiments, the acidic amine based extractant is formed by acidifying an organic amine solution.

In various embodiments, the ratio of the C3-C6 alcohol to water in the fermentation broth or fermentation medium may be less than about 9/91 (w/w), less than about 6/94 (w/w) or less than about 3/97 (w/w).

In some embodiments, the step of increasing the activity may include addition of a hydrophilic solute. In some embodiments, this step may include distilling a vapor phase containing water and C3-C6 alcohol. In some embodiments, this step may include reverse osmosis. In some embodiments, this step may include dialysis. In some embodiments, this step may include adsorption of the C3-C6 alcohol on an alcohol-selective adsorbent. In some embodiments, this step may include extraction of the C3-C6 alcohol into an alcohol-selective extractant. In some embodiments, this step may include adsorption of water on a water-selective adsorbent. In some embodiments, this step may include extraction of water into a water-selective extractant. In some embodiments, this step may include selective removal of water, selective binding of water, or selective rejection of water.

In various embodiments, the C3-C6 alcohol is propanol, butanol, pentanol, or hexanol. In some embodiments, the propanol may be 1-propanol or 2-propanol. In some embodiments, the butanol may be 1-butanol, 2-butanol, tert-butanol (2-methyl-2 propanol), or iso-butanol (2-methyl-1-propanol). In some embodiments, the pentanol may be 1-pentanol, 2-pentanol, 3-pentanol, 2-methyl-1-butanol, 3-methyl-1-butanol, 2-methyl-2-butanol, 3-methyl-2-butanol, or 2,2-dimethyl-1-propanol. In some embodiments, the hexanol may be 1-hexanol, 2-hexanol, 3-hexanol, 2-methyl-1-pentanol, 3-methyl-1-pentanol, 4-methyl-1-pentanol, 2-methyl-2-pentanol, 3-methyl-2-pentanol, 4-methyl-2 pentanol, 2-methyl-3-pentanol, 3-methyl-3-pentanol, 3,3-dimethyl-1-butanol, 2,2-dimethyl-1-butanol, 2,3-dimethyl-1-butanol, 2,3-dimethyl-2-butanol, 3,3-dimethyl-2-butanol, or 2 ethyl-1-butanol. In a preferred embodiment, the C3-C6 alcohol is iso-butanol.

In some embodiments, the method of the instant invention further includes the step of cooling the alcohol-rich phase to increase the ratio of the alcohol to water in the alcohol-rich phase.

In some embodiments, the method includes the step of recovering the C3-C6 alcohol from the alcohol-rich phase. In various embodiments, the step of recovering may include the step of distillation, dialysis, water adsorption, extraction of the C3-C6 alcohol by solvent extraction, contact with a hydrocarbon liquid that is immiscible in water or contact with a hydrophilic compound. This step may produce two phases including a first phase containing the C3-C6 alcohol and water and a second phase containing the C3-C6 alcohol, wherein the ratio of water to C3-C6 alcohol in the second phase is less than in the first phase. In various embodiments, the second phase may contain at least about 90% by weight alcohol, at least about 95% by weight alcohol or at least about 99% by weight alcohol.

In some embodiments, the step of recovering may include distilling the C3-C6 alcohol-rich phase. In such embodiments, the first phase is a vapor phase containing the alcohol and water and the second phase is a high boiling product containing the alcohol. In some embodiments, the method may further include combining the fermentation broth with the high boiling product, prior to the step of increasing the activity of the C3-C6 alcohol. In some embodiments, the method may include combining the fermentation broth with the water-rich phase prior to the step of increasing the activity of the C3-C6 alcohol.

In some embodiments, after the step of increasing the activity, the remaining portion of the dilute aqueous solution may be conducted to a fermentation vessel. In some embodiments, the remaining portion may contain an impurity and the method further includes removing at least a portion of the impurity from at least a portion of the remaining portion before conducting the solution to the fermentation vessel. In some embodiments, the fermentation broth contains an impurity and the ratio of the impurity to the C3-C6 alcohol in the C3-C6 alcohol-rich liquid phase is greater than the ratio in the water-rich phase.

In some embodiments, the step of increasing the activity of the C3-C6 alcohol may include distilling a vapor phase containing water and alcohol and condensing the vapor phase. In some of these embodiments, the portion of the fermentation broth may be treated for water removal before the step of distilling. In some embodiments, the C3-C6 alcohol-rich phase may be treated for water removal. In some embodiments, water removal may be done simultaneously with the step of distilling. The water removal may be by selective removal of water, selective binding of water or selective rejection of water. In various embodiments, the water removal may be effected by addition of a hydrophilic solute, addition of a carbon source, reverse osmosis, dialysis, adsorption of the alcohol on an alcohol-selective adsorbent, extraction of the alcohol into an alcohol-selective extractant, adsorption of water on a water-selective adsorbent or extraction of water into a water selective extractant.

In some embodiments, the ratio of the C3-C6 alcohol to water in the C3-C6 alcohol-rich phase is greater than the ratio of the C3-C6 alcohol to water in the fermentation broth by at least about 5 fold.

In some embodiments, distilling is conducted at below atmospheric pressure and at a temperature of between about 20° C. and about 95° C. In some embodiments, the step of distilling is conducted at a pressure of from about 0.025 bar to about 10 bar. The step of distilling may be conducted in a fermentation vessel or in a distillation vessel. In some embodiments, the portion of the fermentation broth is at the temperature of between about 20° C. and about 95° C. prior to introduction into the distillation vessel. In some embodiments, the portion of the fermentation broth is subjected to below atmospheric pressure in the distillation vessel. In some embodiments, after the step of distilling, the remaining portion of the fermentation broth is conducted from the distillation vessel to the fermentation vessel. In various embodiments, the fermentation vessel may be at the atmospheric pressure, below atmospheric pressure or above atmospheric pressure.

In some embodiments, the C3-C6 alcohol is propanol and the ratio of the alcohol to water in the alcohol-rich phase is greater than about 0.2 (w/w). In some embodiments, the C3-C6 alcohol is butanol and the ratio of the alcohol to water in the alcohol-rich phase is greater than about 1 (w/w). In some embodiments, the C3-C6 alcohol is pentanol and the ratio of the C3-C6 alcohol to water in the C3-C6 alcohol-rich phase is greater than about 4 (w/w).

In some embodiments, where the step of increasing activity of the alcohol includes distilling a vapor phase containing water and the C3-C6 alcohol and condensing the vapor phase, the vapor phase may contain an azeotrope of water and the alcohol. In some embodiments, the ratio of the alcohol to water in the alcohol-rich phase is greater than the ratio in the azeotrope.

In some embodiments, the methods of the present invention further include processing the C3-C6 alcohol-rich phase. In some embodiments, the step of processing may include distilling substantially pure C3-C6 alcohol from the C3-C6 alcohol-rich phase. In some embodiments, processing may include distilling an azeotrope of the C3-C6 alcohol from the C3-C6 alcohol-rich phase. In some embodiments, processing may include contacting the C3-C6 alcohol-rich phase with a C3-C6 alcohol-selective adsorbent. In some embodiments, processing may include converting C3-C6 alcohol in the C3-C6 alcohol-rich phase to an olefin. In some embodiments, processing may include combining the C3-C6 alcohol-rich phase with a hydrocarbon liquid that is immiscible in water. In some embodiments, the combination may form a single uniform phase. In some embodiments, the combination may form a light phase and a heavy phase and the ratio of alcohol to water in the light phase may be greater than the ratio in the heavy phase.

In some embodiments, the culturing may include the process of batch fermentation, a fed-batch fermentation, continuous fermentation, cell recycle fermentation, or an enzyme reaction process. In some embodiments, the microorganism may be *Clostridium butyricum, Clostridium acetobutylicum, Clostridium saccharoperbutylacetonicum, Clostridium saccharobutylicum* or *Clostridium beijerinckii*. In some embodiments, the microorganism may be a temperature resistant microorganism. In some embodiments, the microorganism may be viable at temperatures from about 20° C. to about 95° C. In some embodiments, the microorganism may have a productivity of at least about 0.5 g/L per hour.

DETAILED DESCRIPTION OF THE INVENTION

Figure 1:
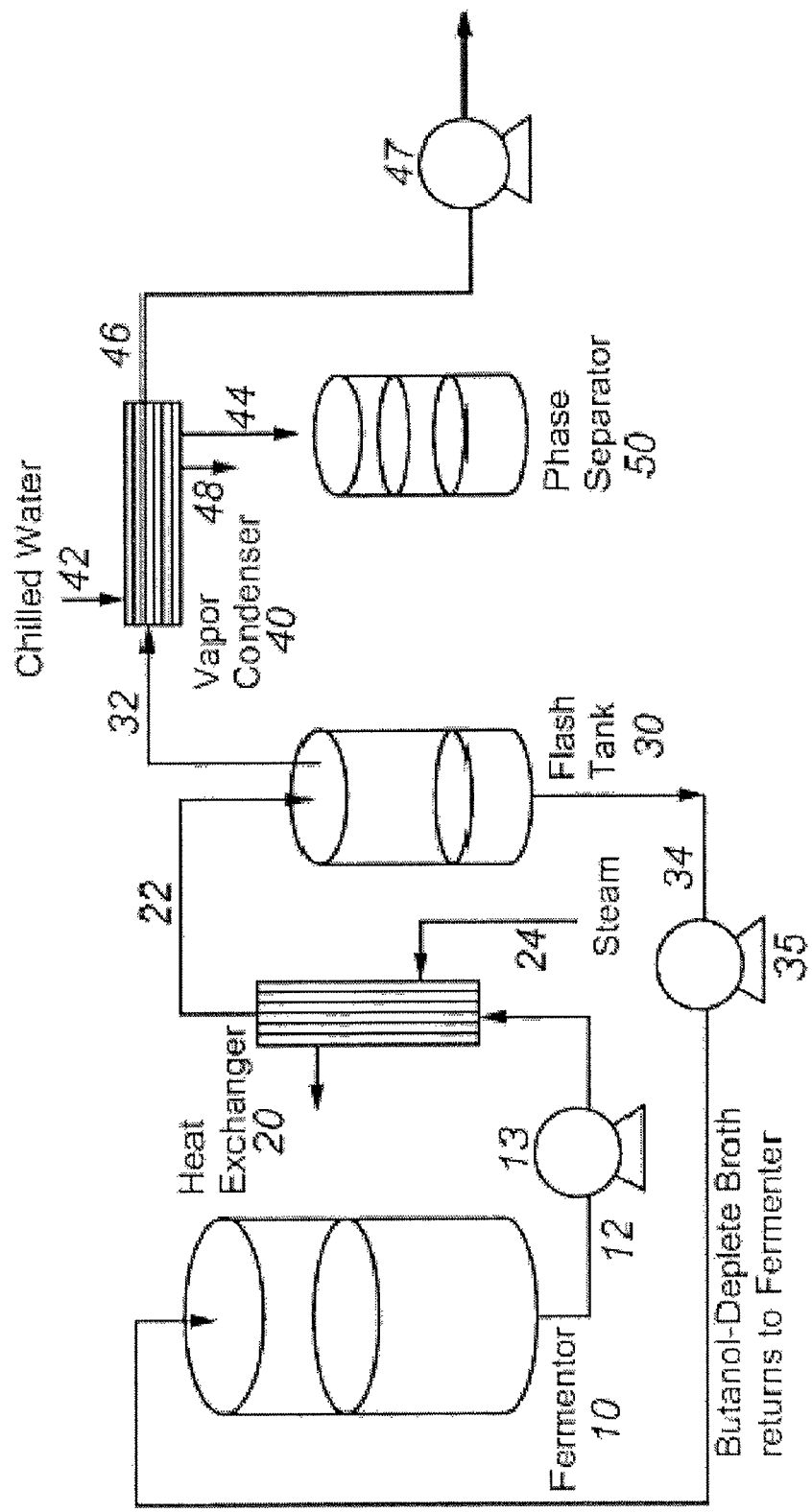
FIG. 1 represents an embodiment of the present invention for the production and recovery of iso-butanol.

The present invention describes methods for recovery of C3-C6 alcohols from dilute aqueous solutions, such as fermentation broths. Fermentation and recovery may be conducted simultaneously. The combination of recovery during fermentation has several key economic advantages. This combination provides improved volumetric productivity for the fermentation and allows recovery of the alcohol. An additional economic advantage is the reduction in energy required to dry the spent fermentation broth. This reduction occurs because the batch concentration of the alcohol product recovered for a given fermentation is raised by the simultaneous fermentation and recovery process which increases the quantity of alcohol produced and recovered per quantity of fermentation broth dried. The term "batch concentration" refers to the concentration for a given fermentor volume based on all of the C3-C6 alcohol produced during the batch fermentation even if some of the C3-C6 alcohol is removed during the fermentation. Thus, the present invention allows for production and recovery of C3-C6 alcohols at low capital and reduced operating costs.

The term "fermentation" or "fermentation process" is defined as a process in which a biocatalyst is cultivated in a culture medium containing raw materials, such as feedstock and nutrients, wherein the biocatalyst converts raw materials, such as a feedstock, into products. A biocatalyst, and related fermentation processes, suitable for the present invention are discussed in detail in the U.S. patent application Ser Nos. 12/263,436 and 12/263,442, filed Oct. 31, 2008, Provisional Application 61/110,543, filed Oct. 31, 2008, and Provisional Application 61/121,830, filed Dec. 11, 2008, which are incorporated by reference in their entirety. The biocatalyst may be any microorganism capable of converting a selected feedstock to a desired C3-C6 alcohol. Further aspects of the biocatalyst are discussed below. Any feedstock that contains a fermentable carbon source is suitable for the present invention.

The terms fermentation broth and fermentation medium are synonymous. Unless explicitly noted, the term fermentation broth should be construed to include both fermentation broth containing micro-organisms as well as fermentation broth which does not contain microorganisms.

In one embodiment, the present invention includes a method to recover a C3-C6 alcohol from a dilute aqueous solution of the C3-C6 alcohol, such as a fermentation broth comprising microorganisms and the C3-C6 alcohol. This method includes increasing the activity of the C3-C6 alcohol in a portion of the aqueous solution to at least that of saturation of the C3-C6 alcohol in the portion. The term saturation of the C3-C6 alcohol in the aqueous solution refers to the maximum concentration of the C3-C6 alcohol under the conditions (e.g. temperature and pressure) of that aqueous solution. The method also includes forming a C3-C6 alcohol-rich liquid phase and a water-rich liquid phase from the portion of the aqueous solution, and the method includes separating the C3-C6 alcohol-rich phase from the water-rich phase.

In an alternative embodiment, the present invention includes a method to recover a C3-C6 alcohol from a dilute aqueous solution of the C3-C6 alcohol, such as a fermentation broth comprising microorganisms and the C3-C6 alcohol. This method includes decreasing the activity of water in a portion of the aqueous solution to at least that of saturation of the C3-C6 alcohol in the portion. The method also includes forming a C3-C6 alcohol-rich liquid phase and a water-rich liquid phase from the portion of the aqueous solution, and the method includes separating the C3-C6 alcohol-rich phase from the water rich phase. An example of increasing the activity of an alcohol is when an alcohol is removed selectively compared with water to form another phase, such as by distillation, extraction and adsorption where the other phase is gaseous, solvent phase and solid adsorbent phase, respectively. Upon condensation of the gaseous phase, separation from the solvent or separation from the adsorbent, a second liquid phase is formed in which the activity of the alcohol is higher than starting solution. An example of decreasing water activity is when water is removed selectively compared with alcohol to form another phase, such as selective adsorption, extraction and even freezing of water. The result is decreasing the activity of water in the starting solution. Some processes both increase the activity of an alcohol and decrease the activity of water. For example, if a hydrophilic solute is added to an aqueous solution of an alcohol, it leads to both decreasing water activity and increasing the alcohol activity.

As used herein the term C3-C6 alcohols refers to an alcohol containing three, four, five or six carbon atoms, including all of the isomers thereof, and mixtures of any of the foregoing. Thus, the C3-C6 alcohol can be selected from propanols, butanols, pentanols, and hexanols. More particularly, the C3 alcohol may be 1-propanol, or 2-propanol; the C4 alcohol may be 1-butanol, 2-butanol, tert-butanol (2-methyl-2-propanol), or iso-butanol (2-methyl-1-propanol); the C5 alcohol may be 1-pentanol, 2-pentanol, 3-pentanol, 2-methyl-1-butanol, 3-methyl-1-butanol, 2-methyl-2-butanol, 3-methyl-2-butanol, or 2,2-dimethyl-1-propanol; and the C6 alcohol may be 1-hexanol, 2-hexanol, 3-hexanol, 2-methyl-1-pentanol, 3-methyl-1-pentanol, 4-methyl-1-pentanol, 2-methyl-2-pentanol, 3 methyl-2-pentanol, 4-methyl-2-pentanol, 2-methyl-3-pentanol, 3-methyl-3-pentanol, 3,3-dimethyl-1-butanol, 2,2-dimethyl-1-butanol, 2,3-dimethyl-1-butanol, 2,3-dimethyl-2-butanol, 3,3-dimethyl-2-butanol, or 2-ethyl-1-butanol. In a preferred embodiment, the C3-C6 alcohol is isobutanol (2-methyl-1-propanol).

A "dilute" aqueous solution as used herein means a solution containing the C3-C6 alcohol at a concentration below the solubility limit of the C3-C6 alcohol in the solution. Concentration can be expressed in a variety of different units, e.g. weight or volume percent, molar concentration, molal concentration or alcohol/water w/w of v/v ratio. Unless specified otherwise, however, the concentrations are presented here as weight percent. In case of a stream comprising at least one additional compound (e.g. solute, solvent, adsorbent, etc.), alcohol weight concentration as used herein is calculated by 100 times alcohol weight in that stream divided by the combined weights of alcohol and water in that stream. In some embodiments, the ratio of the C3-C6 alcohol to water in the dilute aqueous solution is less than about 10/90 (w/w). In some preferred embodiments, the ratio is less than about 9/91 (w/w), less than about 8/92 (w/w), less than about 7/93 (w/w), less than about 6/94 (w/w), less than about 5/95 (w/w), less than about 4/96 (w/w), less than about 3/94 (w/w), less than about 2/98 (w/w), less than about 1/99 (w/w), or less than about 0.5/99.5 (w/w).

In some embodiments, the dilute aqueous solution may comprise a fermentation broth. In other embodiments it may be a recycled stream of the fermentation broth and/or a product of the processing thereof, such as the water rich phase from the step of separating the C3-C6 alcohol-rich phase from the water-rich phase or the high boiling point product comprising the C3-C6 alcohol described below or combinations of those with a fermentation broth. The fermentation broth may comprise the C3-C6 alcohols, along with any impurities. The term "impurity" or "impurities" means any compound other than water and the alcohol being purified. The term impurity includes any byproduct or co-product of the fermentation process i.e. a product related to the production of alcohol, other than the alcohol, in any amount or in an undesired amount. Reference herein to purification means increasing the ratio between a product and another compound other than water.

The method includes increasing the activity of the C3-C6 alcohol in a portion of the aqueous solution to at least that of saturation of the C3-C6 alcohol in the portion. As used herein, reference to a "portion" of a thing, such as a fermentation broth, includes both the entire thing (e.g., an entire fermentation broth) or some part of the entire thing that is less than the entire thing (e.g., a sidestream of a fermentation broth). A portion of a solution or fermentation broth also includes the solution or fermentation broth if it is converted to vapor phase. The activity of a C3-C6 alcohol refers to the effective concentration of the C3-C6 alcohol in an aqueous solution. The activity of the C3-C6 alcohol will depend on temperature, pressure, and composition. The activity of a species can be changed or modified because molecules in a non-ideal solution, such as a fermentation medium interact with each other and interact differently with different types of molecules. For example, if a hydrophilic solute is introduced into an aqueous isobutanol solution, the hydrophilic solute will interact with greater affinity with the water in the solution than with the isobutanol. The activity of the isobutanol in the solution will thereby be increased. The activity coefficient for a compound in an aqueous solution is an indicator of what concentration of that compound will be in a vapor phase in equilibrium with the solution and is a function of the concentration of the compound in water. The activity of a compound in a solution is the product of the concentration of the compound and its activity coefficient. For example, in an isobutanol-water mixture, the activity coefficient for isobutanol is higher than water. Therefore, the concentration of isobutanol in the vapor phase in equilibrium with the aqueous solution will be higher than in the solution.

Increasing the activity of the C3-C6 alcohol to at least that of saturation of the C3-C6 alcohol in an aqueous solution refers to processing a portion of the aqueous solution to form a composition comprising C3-C6 alcohol in which the effective concentration of the C3-C6 alcohol with respect to the aqueous solution is greater than in the starting portion. This step promotes the condition that some of the C3-C6 alcohol is no longer soluble in the aqueous solution and enables the formation of a C3-C6 alcohol-rich liquid phase and a water-rich liquid phase. Such processing can encompass a variety of process steps including, but not limited to addition of a hydrophilic solute, distilling a vapor phase comprising water and the C3-C6 alcohol, reverse osmosis, dialysis, selective adsorption and solvent extraction.

As used herein, the term dialysis means selective transfer of water from the solution through a membrane into another compartment. Dialysis differs from reverse osmosis in that in reverse osmosis, water transfer is induced by applying pressure on alcohol solution, while in dialysis, water transfer is induced into a compartment by having a concentrated solution in the compartment.

According to an embodiment of the invention, increasing the activity of the C3-C6 alcohol may comprise adding a hydrophilic solute to the aqueous solution. In some embodiments in which the aqueous solution is a fermentation broth, the hydrophilic solute may be added to the entire fermentation broth in the fermentor or to a partial stream taken from the fermentor, either with microorganisms in the broth or after removal of them. Reference to adding a hydrophilic solute can refer to increasing the concentration of a hydrophilic solute already existing in the portion of the solution or to addition of a hydrophilic solute that was not previously in the solution. Such increase in concentration may be done by external addition. Alternatively, or additionally, increasing concentration may also be conducted by in situ treatment of the solution, such as by hydrolyzing a solute already existing in the solution, e.g. hydrolyzing proteins to add amino acids to the solution, hydrolyzing starch or cellulose to add glucose to the solution and/or hydrolyzing hemicellulose to add pentoses to the solution. According to another preferred embodiment, the hydrophilic solute may be one that has a nutritional value and optionally ends up in a fermentation coproduct stream, such as distillers dried grains and solubles (DDGS). In addition or alternatively, the hydrophilic solute can be fermentable and can be transferred with the water-rich liquid phase to the fermentor.

Sufficient hydrophilic solute is added to enable the formation of a second liquid phase, either solely by addition of the hydrophilic solute or in combination with other process steps. The required amount depends on the chemical nature of the alcohol, typically decreasing with increasing number of carbon atoms in the alcohol and being smaller for normal alcohols and linear ones compared with secondary or tertiary alcohols and branched ones. The required amount further decreases with increasing concentration of the alcohol in the fermentation liquid and possibly also with increasing concentration of other solutes there. The amount required in each case can be determined, in view of the present invention, experimentally.

Preferred hydrophilic solutes are those that have a strong effect of lowering the water partial vapor pressure of aqueous solutions. The added hydrophilic solute may be a salt, an amino acid, a water-soluble solvent, a sugar or combinations of those. In related embodiments, the hydrophilic solute can be recovered. For example, if the dilute aqueous solution is fermentation broth and the hydrophilic solute added to increase the activity of the C3-C6 alcohol in the fermentation broth is $CaCl_2$, then $CaCl_2$, after formation of alcohol-rich and water-rich liquid phases, will be primarily found the water-rich liquid phase and can be recovered therefrom.

In some embodiments, the hydrophilic solute may be a water soluble carbon source. In the embodiments in which the aqueous solution is a fermentation broth, the water soluble carbon source may be added to the entire fermentation broth in the fermentor or to a partial stream taken from the fermentor, either with microorganisms in the broth or after removal of them. Reference to adding a water soluble carbon source can refer to increasing the concentration of a water soluble carbon source already existing in the portion of the solution or to addition of a hydrophilic solute that was not previously in the solution. Such increase in concentration may be done by external addition. Alternatively, or additionally, increasing concentration may also be conducted by in situ treatment of the solution, such as by hydrolyzing a carbon source already existing in the solution, e.g. hydrolyzing proteins to add amino acids to the solution, hydrolyzing starch or cellulose to add glucose to the solution and/or hydrolyzing hemicellulose to add pentoses to the solution. According to another preferred embodiment, the water soluble carbon source may have a nutritional value and optionally may end up in a fermentation coproduct stream, such as distillers dried grains and solubles (DDGS).

Preferred water soluble carbon source are those that have a strong effect of lowering the water partial vapor pressure of aqueous solutions and ones that are well fermented. The added water soluble carbon source may be a carbohydrate such as a monosaccharide, a disaccharide or an oligosaccharide and their combinations. Such saccharide may comprise hexoses, e.g. glucose and fructose and pentoses (e.g. xylose or arabinose) and their combination. Also suitable is a precursor of such carbohydrate, such as starch, cellulose, hemicellulose and sucrose or combinations of those. In related embodiments, the water soluble carbon source can be recovered or used. For example, if the dilute aqueous solution is a portion of a fermentation broth and the water soluble carbon source added to increase the activity of the C3-C6 alcohol in the fermentation broth is glucose, then glucose will be primarily found in a water-rich liquid phase and can be conducted back to the fermentation broth to provide carbon for fermentation.

In some embodiments, the step of increasing the activity of the C3-C6 alcohol comprises distilling a vapor phase comprising water and the C3-C6 alcohol. The aqueous solution, such as a fermentation broth, can be distilled wherein the alcohol and water are vaporized to form an alcohol-depleted liquid phase and an alcohol-enriched vapor phase. The step of distillation can be accomplished by increasing the temperature of the aqueous solution, reducing the atmospheric pressure on the aqueous solution or some combination thereof. The C3-C6 alcohol concentration in the vapor phase is greater than in the aqueous solution. According to a preferred embodiment, C3-C6 alcohol concentration in the vapor phase is at least about 5 times greater than the concentration in the aqueous solution, preferably about 10 times, preferably about 15 times, preferably about 20 times, preferably about 25 times, and preferably about 30 times. The vapor phase may be condensed, such as at conditions selected so that immiscible alcohol-rich and water-rich (i.e., alcohol-poor) solutions are formed.

The step of distilling can be conducted at below atmospheric pressure, at about atmospheric pressure or above atmospheric pressure. Reference herein to atmospheric pressure is to atmospheric pressure at sea level and unless otherwise specified, all pressures expressed herein are absolute pressures. Suitable below atmospheric pressures include pressures from about 0.025 bar to about 1.01 bar, from about 0.075 bar to about 1.01 bar, and from about 15 bar to about 1.01 bar. Suitable above atmospheric pressures include pressures from about 1.01 bar to about 10 bar, from about 1.01 bar to about 6 bar, and from about 1.01 bar to about 3 bar.

In the embodiment when the step of distilling is conducted at below atmospheric pressures, the temperature can be between about 20° C. and about 95° C., between about 25° C. and about 95° C., between about 30° C. and about 95° C., or between about 35° C. and about 95° C.

In a further embodiment, in which the aqueous solution is a portion of a fermentation broth and comprises microorganisms, and in which the step of distilling is conducted in a distillation vessel, the portion of the fermentation broth is at the temperature of between about 20° C. and about 95° C., between about 25° C. and about 95° C., between about 30° C. and about 95° C., or between about 35° C. and about 95° C. prior to introduction into the distillation vessel. In another embodiment, the temperature of the portion of the fermentation broth is brought to the desired value after it is introduced in the distillation vessel. Preferably, microorganisms are used that are viable, and even more preferably, both viable and productive at these temperatures.

Optionally, after the step of distilling, the alcohol-depleted remaining portion of the fermentation broth can be conducted from the distillation vessel to a fermentation vessel. Optionally, the alcohol-depleted remaining portion of the fermentation broth can be mixed with water, with feedstock and/or possibly other nutrients to form the culture medium for further fermentation.

In a further embodiment, in which the portion of the aqueous solution is a portion of a fermentation broth, the step of distilling can be conducted in a fermentation vessel.

In the case where the step of increasing the activity of the C3-C6 alcohol comprises distilling a vapor phase comprising water and the C3-C6 alcohol and condensing the vapor phase, the method can also include treating the portion of the dilute aqueous solution for decreasing water activity. In various embodiments, said decreasing water activity comprises water removal before the step of distilling or simultaneously with the step of distilling. The step of treating can include selective removal of water, selective binding of water or selective rejection of water. According to various embodiments, the step of treating can include addition of a hydrophilic solute, addition of a carbon source, reverse osmosis, dialysis, adsorption of the alcohol on a selective adsorbent, extraction of the alcohol into a selective extractant, adsorption of water on a selective adsorbent, or extraction of water into a selective extractant.

In a further embodiment in which the step of increasing the activity of the C3-C6 alcohol comprises distilling a vapor phase comprising water and the C3-C6 alcohol and condensing the vapor phase, the method can also include treating C3-C6 alcohol-rich phase for water removal. The step of treating can include selective removal of water, selective binding of water or selective rejection of water. Alternatively, the step of treating can include addition of a hydrophilic solute, addition of a carbon source, reverse osmosis, dialysis, adsorption of the butanol on a selective adsorbent, extraction of the butanol into a selective extractant, adsorption of water on a selective adsorbent, or extraction of water into a selective extractant.

In a preferred embodiment, the step of distilling is conducted in a flash tank, that can be operatively connected to a fermentation vessel and the process can further comprise circulating the culture medium from the fermentation vessel to the flash tank, and circulating the culture medium from the flash tank to the fermentation vessel. A flash is a one stage distillation where the vapor and liquid outlet from the flash system are in equilibrium with each other and the temperature and pressure of each phase is nearly identical. Distillation, on the other hand, comprises a series of flash stages strung together sequentially. During distillation i.e. in a multi stage flash system, such as a distillation column, the vapor that comes out the top and the liquid that comes out the bottom leave at different temperatures than in a flash.

According to another embodiment, the process includes reducing pressure in a distillation vessel compared with that in the fermentation vessel. Such a pressure reduction coupled with adiabatic vaporization allows for removal of heat from the portion of the fermentation broth of the aqueous solution generated in the fermentation vessel within the distillation vessel. Alternatively or in addition, the process can include increasing pressure on the aqueous solution from the distillation vessel in the fermentation vessel. Such a pressure increase creates heat, which can be used to preheat the system at various points. For example, the heat can be used to preheat the feed in the flash tank, the beer still and/or the distillation column and can also be used in the evaporators used to concentrate the thin stillage to syrup. These components are discussed in detail below.

Flash tank vacuum evaporation operations have less engineering concerns regarding pressure drop under vacuum because the flash tank acts as a single stage of separation without stages of liquid above the flash tank impacting pressure drop on the system, and the differential pressure across flash tank operations can be very low. Design calculations for vapor generation in the flash tank and sizing of piping systems can be appropriately selected to achieve low pressure drop. The distillation of a C3-C6 alcohol in a flash tank requires less vacuum than a distillation column and, thus, the flash tank has lower operating cost and capital costs inasmuch as the equipment is smaller in size and simpler in construction.

In a preferred embodiment, when the step of increasing the activity of the C3-C6 alcohol comprises distilling a vapor phase comprising water and the C3-C6 alcohol, the mixed vapor includes an azeotropic composition. Azeotropes are formed when molecular forces cause two or more molecular species to behave as a new vapor or/liquid species. Azeotropes are generally viewed as a limitation by chemical process industries because the azeotrope composition "pinch point" prevents the distillation of the mixture into pure components. Instead of producing pure components from the distillation process, the azeotrope manifests itself as an azeotropic composition at the top of the distillation column, as a minimum boiling point azeotrope, or from the bottom of the distillation column, as a maximum boiling point azeotrope.

When fermentation products form a maximum boiling point azeotrope with water, all of the non-azeotrope bound water must be vaporized and distilled overhead. Products within fermentation broth are typically dilute. As a result, when maximum boiling point azeotropes are formed, the amount of energy required to boil up and remove the excess un-bound water is a large heat load and can often make the vaporization and condensation processes of distillation uneconomical. Additionally, the maximum boiling point azeotrope occurs at temperatures above the boiling points of the pure species, elevating the bottom temperatures in the distillation system. As a result, the bottoms product in the maximum boiling point experiences a higher heat history than the pure species. This high temperature heat history can degrade the value of the primary product and co-products of fermentation. Distiller's dry grains and solubles (DDGS), which are typically used as a feed ingredient, are one example of such a co-product which can be degraded with exposure to high heat and lose nutritional values.

Minimum boiling point azeotropes are also known as positive azeotropes because the azeotrope has an activity coefficient of greater than 1. Maximum boiling point azeotropes are also referred to as negative azeotropes because their activity coefficient is less than 1. The magnitude of the activity coefficient dictates the degree of non-ideal activity of the azeotropic entity. This non-ideality and difficulty in separation of azeotropes has been studied. The activity coefficient is not fixed but is a function of concentration of the compound in water. As a result, the solution boiling point of the azeotrope composition varies as the concentration of the component varies. As a result, the azeotropic composition developed in the vapor phase can be affected by component concentration and operating pressure.

According to a preferred embodiment, an aqueous solution of the C3-C6 alcohol forms a minimum boiling point azeotrope. According to a related preferred embodiment, the concentration of the C3-C6 alcohol in the mixed vapor is substantially equal to the concentration of the alcohol in the minimum boiling point azeotrope at the pressure selected for distillation. In some particularly preferred embodiments, the concentration of the C3-C6 alcohol in the mixed vapor is greater than the concentration of the alcohol in the minimum boiling point azeotrope, as in some cases where the aqueous solution comprises other solutes in addition to the alcohol that affect the water partial vapor pressure.

Some azeotropes are known to be stable under a broad range of operating pressures, while other azeotrope systems can be "broken" by low and high pressure. For example, the ethanol-water azeotrope is broken at pressures less than 70 torr. For azeotropes that can be broken under vacuum, the use of distillation columns is sometimes limited due to the fact that the vacuum distillation columns require that the pressure drop in the distillation column is significant enough that it requires deeper vacuum to be pulled at the vacuum source. For example, attempting to maintain the vacuum distillation column feed pressure to 150 mm Hg requires that the pressure drop in the column be very small so as to ensure that the vacuum pump can maintain proper vacuum levels. To achieve low pressure drop in vacuum columns with multiple trays requires small liquid heights on the distillation trays. The low pressure drop and low liquid height in the column typically increases the column capital cost by increasing the diameter of the column.

In some embodiments, the step of increasing the activity of the C3-C6 alcohol comprises dialysis. Dialysis works on the principle of diffusion of solutes and ultra-filtration of fluid across a semi-permeable membrane. Any membrane separation system that selectively removes water from the aqueous solution is suitable for the process of the present invention. According to a preferred embodiment, dialysis is conducted in a system comprising two or more compartments. The aqueous solution of the alcohol is introduced into one and water from this solution transfers selectively through the membrane into the other. According to a preferred embodiment, the water transfer is induced by osmotic pressure. The water-receiving compartment contains a hydrophilic compound, e.g. $CaCl_2$ or a carbohydrate, or a concentrated solution of such compound. A concentrated solution is formed in the water-receiving compartment. That solution is treated according to various embodiments to regenerate the solute or its concentrated solution, or for other applications. Regeneration can be done by known means such as water distillation. In the case where the solute is a carbohydrate or another source of fermentable carbon, the solution can be used provide fermentables to the fermentation step.

In some embodiments, the step of increasing the activity of the C3-C6 alcohol comprises reverse osmosis. In reverse osmosis, the aqueous solution is contacted in a first compartment with a reverse osmosis membrane under pressure, whereby water selectively transfers through the membrane to a second compartment, while the alcohol is retained in the first compartment. As a result of selective water transfer into the second compartment, the concentration (and activity) of the alcohol in the liquid of the first compartment increases and preferably reaches saturation, whereby a second phase is formed in that first compartment. That compartment comprises according to this embodiment two liquid phases one of which is an alcohol-saturated aqueous phase and the other is a water saturated alcohol solution.

In some embodiments, the step of increasing the activity of the C3-C6 alcohol comprises solvent extraction. In solvent extraction, the aqueous solution is contacted with another liquid phase (solvent or extractant), wherein at least one of water and the alcohol are not fully miscible. The two phases are mixed and then allowed to settle. According to one embodiment, the step of increasing the activity of the C3-C6 alcohol comprises extraction of the C3-C6 alcohol into an alcohol-selective extractant. The term "alcohol-selective extractant" means an extractant preferring alcohol over water so that the alcohol/water ratio in the extractant is greater than in the remaining aqueous solution. Thus, the alcohol-selective extractant or solvent is selective to the alcohol (similarly or more hydrophobic than the alcohol) and the alcohol transfers preferentially into the extractant or solvent to form alcohol-containing extractant or solvent, also referred to as extract. In some preferred embodiments, the alcohol-selective solvent may be butylacetate, tributylphosphate, decanol, 2-heptanone or octane. In another embodiment, the step of increasing the activity of the C3-C6 alcohol comprises extraction of water into a water selective extractant. The term "water-selective extractant" means an extractant preferring water over alcohol so that the alcohol/water ratio in the extractant is lower than in the remaining aqueous solution. Thus, the water-selective extractant or solvent is selective to water (more hydrophilic than the alcohol), so that water transfers preferentially into the water-selective extractant or solvent.

In a preferred embodiment, the alcohol-selective solvent can be an acidic, amine based extractant. Such an extractant can be prepared by mixing an amine with a diluent and contacting the mixture with an acid. Amines that are suitable for forming the extractant include primary, secondary, tertiary and quaternary amines, and preferably include primary, secondary, tertiary amines. Suitable amines are also water-insoluble in both free and salt form (i.e. when an acid is bound to them). Preferably the aggregate/total number of carbon atoms on the amines is at least 20. Both aliphatic and aromatic amines are suitable and aliphatic ones are preferred. The diluent can be a hydrocarbon or another non-reactive organic solvent with boiling point of at least about 60° C., and preferably at least about 80° C. The acid can be any strong acid, such as one with a pKa (-log dissociation constant) of not greater than 3, and can either be a mineral acid or an organic acid. In one example, the amine can be trioctyl amine, the acid can be sulfuric acid and the diluent can be decane. The acid is extracted (binds to the amine) to form the extractant.

In some embodiments the step of increasing the activity of the C3-C6 alcohol comprises adsorption of the C3-C6 alcohol or water on a selective adsorbent. In adsorption, the aqueous solution is contacted with a selective adsorbent that has greater selectivity for either alcohol or water. In one embodiment, the step of increasing the activity of the C3-C6 alcohol comprises adsorption of the C3-C6 alcohol on an alcohol selective adsorbent. An "alcohol-selective adsorbent" means an adsorbent preferring alcohol over water so that the alcohol/water ratio on the adsorbent is greater than in the remaining aqueous solution. In another embodiment, the step of increasing the activity of the C3-C6 alcohol comprises adsorption of water on a water-selective adsorbent. A "water-selective adsorbent" means an adsorbent preferring water over alcohol so that the alcohol/water ratio on the adsorbent is lower than in the remaining aqueous solution. Thus, the aqueous phase is contacted with a water-selective adsorbent, a water-carrying adsorbent is formed and the aqueous solution is enriched in the C3-C6 alcohol. According to various embodiments, the water adsorbent is hydrophilic, has surface functions capable of forming hydrogen bonds and/or has pores suitable in size to the size of water molecules. In some embodiments the adsorbent may be solid. According to a preferred embodiment, a fermentation feedstock, such as ground corn may be the adsorbent. For example, the feedstock may be contacted with the aqueous solution to selectively adsorb water out of it. In some embodiments the adsorbent may be a molecular sieve.

The method further includes the step of forming a C3-C6 alcohol-rich liquid phase and a water-rich liquid phase from the portion of the aqueous solution which has been treated to increase the activity of the C3-C6 alcohol. As used here, the term "alcohol-rich liquid phase" means a liquid phase wherein the alcohol-to-water ratio is greater than that in the portion of the aqueous solution. The term "water-rich liquid phase" means a liquid phase wherein the water-to-alcohol ratio is greater than that of the alcohol-rich liquid phase. The water-rich phase is also referred to in the following as alcohol-lean phase. The step of forming the two phases can be active. For example, in some embodiments, the step of forming may comprise condensing a distilled vapor phase that forms two phases after condensation. Alternatively or in addition, chilling or cooling the treated portion of the aqueous solution can result in the formation of the two phases. Other steps for actively forming the two phases can include using equipment shaped to promote the separation of phases. Separation of the phases can be accomplished in various unit operations including liquid-liquid separators comprising a liquid/liquid separator utilizing specific gravity differences between the phases and a water boot, g-force separation as in a centrifuge, or centrifugal liquid-liquid separators. Also suitable are settlers as in mixer settler units used for solvent extraction processes. In some embodiments the step of forming is passive and may simply be a natural consequence of the previous step of increasing the activity of the C3-C6 alcohol to at least that of saturation.

In the alcohol-rich liquid phase, the ratio of the concentration of the C3-C6 alcohol with respect to the water is effectively greater than in the starting portion. In the water-rich phase, the ratio of concentration of the C3-C6 alcohol with respect to water is effectively less than in the alcohol-rich liquid phase. The water-rich phase may also be referred to as the alcohol-poor phase.

In some embodiments, the C3-C6 alcohol is propanol and the weight ratio of propanol to water in the alcohol-rich phase is greater than about 0.2, greater than about 0.5, or greater than about 1. In some embodiments, the C3-C6 alcohol is butanol and the ratio of butanol to water in the alcohol-rich phase is greater than about 1, greater than about 2, or greater than about 8. In some embodiments, the C3-C6 alcohol is pentanol and the ratio of pentanol to water in the alcohol-rich phase is greater than about 4, greater than about 6, or greater than about 10.

The concentration factor or enrichment factor for a given phase can be expressed as the ratio of alcohol to water in that phase divided by the ratio of alcohol to water in the dilute aqueous solution. Thus, for example, the concentration or enrichment factor for the alcohol-rich phase may be expressed as the ratio of alcohol/water in the alcohol-rich phase divided by that ratio in the aqueous dilute solution.

In some embodiments, the ratio of the C3-C6 alcohol to water in the C3-C6 alcohol-rich phase is greater than the ratio of the C3-C6 alcohol to water in the fermentation broth by at least about 5 fold, at least about 25 fold, at least about 50 fold, at least about 100 fold, or at least about 300 fold.

The process further includes separating the C3-C6 alcohol-rich phase from the water-rich phase. Separating the two phases refers to physical separation of the two phases and can include removing, skimming, pouring out, decanting or otherwise transferring one phase from another and may be accomplished by any means known in the art for separation of liquid phases.

In some embodiments, the method further comprises the step of cooling the C3-C6 alcohol-rich phase to increase the ratio of the C3-C6 alcohol to water in the alcohol-rich phase.

In some embodiments, the method further comprises recovering the C3-C6 alcohol from the alcohol-rich phase. Recovering refers to isolating the C3-C6 alcohol from the alcohol-rich phase. Recovering also includes enriching or increasing the concentration of the C3-C6 alcohol in the alcohol-rich phase. In various embodiments, this step may comprise a process selected from the group consisting of distillation, dialysis, water adsorption (e.g., such as use of molecular sieves), solvent extraction, contact with a hydrocarbon liquid that is immiscible in water and contact with a hydrophilic compound to produce a first phase comprising the C3-C6 alcohol and water and a second phase comprising C3-C6 alcohol, wherein the ratio of water to C3-C6 alcohol in the second phase is less than in the first phase. In preferred embodiments, the second phase comprises at least about 80%, about 85%, about 90%, about 95% or about 99% by weight C3-C6 alcohol. As used herein a liquid that is immiscible in water has a miscibility in water of less than about 1 wt %.

Methods of distillation and dialysis are discussed above with respect to the step of increasing the activity of C3-C6 alcohols and similar processes can be used to recover C3-C6 alcohol from a C3-C6 alcohol-rich phase. Regarding the use of water adsorption to recover C3-C6 alcohol from a C3-C6 alcohol-rich phase, the alcohol-rich phase is contacted with an adsorbent that selectively adsorbs water out of the alcohol rich phase. A water-carrying adsorbent is formed and the alcohol-rich phase is further enriched in the C3-C6 alcohol. According to various embodiments, the water adsorbent is hydrophilic, has surface functions capable of forming hydrogen bonds and/or has pores suitable in size to the size of water molecules. In some embodiments the adsorbent may be solid. According to a preferred embodiment, a fermentation feedstock, such as ground corn may be the adsorbent. For example, the feedstock may be contacted with the C3-C6 alcohol-rich phase to selectively adsorb water out of it. In some embodiments the adsorbent may be a molecular sieve.

Solvent extraction can also be used to recover C3-C6 alcohol from a C3-C6 alcohol-rich phase. In solvent extraction, the alcohol-rich phase is contacted with another liquid phase (solvent), wherein at least one of water and the alcohol are not fully miscible. The two phases are mixed and then allowed to settle. According to one embodiment, the solvent is selective to water (more hydrophilic than the alcohol), water transfers preferentially to the solvent phase and the alcohol-to-water ratio in the other phase increases. According to another embodiment, the solvent is selective to the alcohol (similarly or more hydrophobic than the alcohol). In some preferred embodiments the alcohol-selective solvent may be butylacetate, tributylphosphate, decanol, 2-heptanone or octane. The alcohol transfers preferentially into the solvent. In a following step, the alcohol is separated from the solvent in a form having higher alcohol-to-water ratio compared with that of the alcohol-rich phase.

Contact with a hydrocarbon liquid that is immiscible in water can also be used to recover C3-C6 alcohol from a C3-C6 alcohol-rich phase. Such liquids are hydrophobic solvents and act as described above for hydrophobic solvents, i.e. extracting the alcohol from the alcohol-rich phase. Examples of such hydrocarbon liquids include gasoline, crude oil, Fischer Tropsch materials and biofuels.

Contact with a hydrophilic compound can also be used to recover C3-C6 alcohol from a C3-C6 alcohol-rich phase. This method for recovery is similar to that described above for use of a hydrophilic compound to increase alcohol activity or to decrease water activity.

In the case of distillation to recover C3-C6 alcohol from a C3-C6 alcohol-rich phase, the first phase comprises a vapor phase comprising C3-C6 alcohol and water and the second phase comprises a high boiling product comprising C3-C6 alcohol.

In a further embodiment of the present invention, the process can include after the step of increasing the activity, conducting (or transporting) the remaining portion of the dilute aqueous solution, such as a fermentation broth, to a fermentation vessel. In this embodiment, the remaining portion of the dilute aqueous solution can comprise an impurity and the process further includes removing at least a portion of the impurity from at least a portion of the remaining portion before conducting the remaining portion to the fermentation vessel. Such impurities can be, for example, ethanol, acetate, aldehydes such as butyraldehyde, and short chain fatty acids. In some embodiments, the dilute aqueous solution can include an impurity and the ratio of the impurity to the C3-C6 alcohol in the C3-C6 alcohol-rich liquid phase is greater than the ratio in the water-rich phase. In some embodiments, the ratio of the impurity to the C3-C6 alcohol in the C3-C6 water-rich liquid phase is greater than the ratio in the alcohol-rich phase.

In further embodiments of the invention, the C3-C6 alcohol-rich phase is further processed to increase the value or utility of the phase. Other embodiments of further processing are disclosed in U.S. patent application Ser. No. 12/327,723, filed Dec. 3, 2008, which is incorporated by reference in its entirety. For example, the C3-C6 alcohol-rich phase can be further processed by (i) distilling substantially pure C3-C6 alcohol from the C3-C6 alcohol-rich phase, (ii) distilling an azeotrope of the C3-C6 alcohol from the C3-C6 alcohol-rich phase, (iii) contacting the C3-C6 alcohol-rich phase with a C3-C6 alcohol-selective adsorbent; or (iv) combining the C3-C6 alcohol-rich phase with a hydrocarbon liquid that is immiscible in water. In the case of distilling substantially pure C3-C6 alcohol from the C3-C6 alcohol-rich phase, the substantially pure C3-C6 alcohol can have a low proportion of impurities (such as reflected by having a low ratio of impurities to C3-C6 alcohol). For example, the ratio of impurities to C3-C6 alcohol, in the substantially pure C3-C6 alcohol can be less than about 5/95, less than about 2/98, or less than about 1/99. Alternatively the substantially pure C3-C6 alcohol can have a water content of less than about 5 wt %, less than about 1 wt % or less than about 0.5 wt %.

In the case of combining the C3-C6 alcohol-rich phase with a hydrocarbon liquid that is immiscible in water, the resulting combination can form a single uniform phase. Alternatively, in the case of combining the C3-C6 alcohol-rich phase with a hydrocarbon liquid that is immiscible in water, the combination can form a light phase and a heavy phase and the ratio of C3-C6 alcohol to water in the light phase is greater than in the heavy phase. According to an embodiment of the method, the hydrocarbon liquid is a fuel, such as gasoline. According to a related embodiment, a C3-C6 alcohol-enriched fuel is formed by combining a fuel with a C3-C6 alcohol-rich phase, further comprising water. As a result of combining the C3-C6 alcohol selectively transfers into the fuel phase to form said enriched fuel, whereas the majority of the water contained initially in the alcohol-rich phase separates as a water-rich heavy phase, which is separated from the fuel.

In other embodiments of the invention, in which the dilute aqueous solution is a fermentation medium, the process can include a step of culturing a microorganism in a fermentation medium to produce the C3-C6 alcohol before the steps of increasing the activity of the C3-C6 alcohol in a portion of the fermentation medium, forming a C3-C6 alcohol-rich liquid phase and a water-rich phase and separating the C3-C6 alcohol-rich phase from the water-rich phase. In one preferred embodiment, the invention further includes the step of conducting the water rich phase to the fermentation medium before the step of increasing the activity of the alcohol. In such embodiments, the step of culturing can be a process selected from a batch fermentation, a fed-batch fermentation, a continuous fermentation, a cell recycle fermentation, and an enzyme reaction process.

As noted above, a suitable biocatalyst, and related fermentation processes, are discussed in detail in the U.S. patent application Ser. Nos. 12/263,436 and 12/263,442, filed Oct. 31, 2008, provisional application 61/110,543, filed Oct. 31, 2008 and provisional application 61/121,830, filed Dec. 11, 2008. Suitable microorganisms can be selected from naturally occurring microorganisms, genetically engineered microorganisms and microorganisms developed by classical techniques, or a combination thereof. Such microorganisms can include, without limitation, bacteria and fungi (including yeast). For example, suitable bacteria can include those that are capable of alcohol production such as the bacteria of the *Clostridium* species. Examples of these include without limitation, *Clostridium butyricum*, *Clostridium acetobutylicum*, *Clostridium saccharoperbutylacetonicum*, *Clostridium saccharobutylicum* and *Clostridium beijerinckii*.

Suitable bacteria and fungi also include those that are capable of hydrolyzing carbohydrates and can be genetically engineered to produce alcohols. Examples include, without limitation, bacteria of the order Clostridiales (e.g. *Butyrovibrio fibrisolvens*), Bacilliales (e.g. *Bacillus circulans*), Actinomycetales (e.g. *Streptomyces cellulolyticus*), Fibrobacterales (e.g. *Fibrobacter succinogenes*), Xanthomonadales (*Xanthomonas* species) and Pseudomonadales (e.g. *Pseudomonas mendocina*) and fungi such as those of the order *Rhizopus, Saccharomycopsis, Aspergillus, Schwanniomyces* and *Polysporus*. The fungi may be able to do the conversion aerobically or anaerobically. Examples of anaerobic fungi include, without limitation, *Piromyces* species (e.g. strain E2), *Orpinomyces* species (e.g. *Orpinomyces Bovis*), *Neocallimastix* species (*N. frontalis*), *Caecomyce* species, *Anaeromyces* species and *Ruminomyces* species. S.E.→+$_2$ →+$^+$→+→+$_2$ →+$^+$ As noted above, any microorganism, whether naturally occurring or manmade, that is capable of producing alcohol can be used and the methods of the present invention are not limited to the examples listed here. In some embodiments, the microorganism is viable at temperatures from about 20° C. to about 95° C. Reference to a microorganism being viable at a given temperature or range of temperatures refers to a microorganism being able to survive exposure to such temperatures and subsequently be able to grow and/or produce metabolic products under the same or different conditions. In other embodiments, the microorganism is a temperature resistant microorganism. The term "resistance" is defined as the property of a biocatalyst to have a low rate of inhibition in the presence of increasing concentrations of an inhibitor in the fermentation broth. The term "more resistant" describes a biocatalyst that has a lower rate of inhibition towards an inhibitor than another biocatalyst with a higher rate of inhibition towards the same inhibitor. For example, two biocatalysts A and B, both with a tolerance of 2% to an inhibitor biofuel precursor and a specific productivity of 1 g product per g CDW per h, exhibit at 3% biofuel precursor a specific productivity of 0.5 g product per g CDW per h and 0.75 g product per g CDW per h for A and B, respectively. The biocatalyst B is more resistant than A. The term "temperature resistant" describes a biocatalyst that has a lower rate of inhibition at a given temperature than another biocatalyst with a higher rate of inhibition at the same temperature.

The term "tolerance" is defined as the ability of the biocatalyst to maintain its specific productivity at a given concentration of an inhibitor. The term "tolerant" describes a biocatalyst that maintains its specific productivity at a given concentration of an inhibitor. For example, if in the presence of 2% of an inhibitor a biocatalyst maintains the specific productivity that it had at 0 to 2%, the biocatalyst is tolerant to 2% of the inhibitor or has a tolerance to 2% of the inhibitor. The term "tolerance to temperature" is defined as the ability of the biocatalyst to maintain its specific productivity at a given temperature.

In some embodiments, the microorganism has a productivity of at least about 0.5 g/L per hour of the C3-C6 alcohol in aggregate over the lifetime of a batch fermentation cycle. In some embodiments, the productivity is at least about 1, at least about 1.5, at least about 2.0, at least about 2.5, at least about 3.0, at least about 3.5, at least about 4.0, at least about 4.5, and at least about 5.0 g/L per hour of the C3-C6 alcohol in aggregate over the lifetime of a batch fermentation cycle. In some embodiments, the productivity ranges from about 0.5 g/L per hour to about 5 g/L per hour of the C3-C6 alcohol over the lifetime of a batch fermentation cycle.

In other embodiments, preferred microorganisms are ones that produce the desired alcohol with no or minimal coproducts or byproducts. Also preferred are microorganisms that use simple and low cost fermentation media.

Any feedstock that contains a fermentable carbon source is suitable for embodiments of the present invention that include a step of culturing a microorganism. Examples include feedstocks containing polysaccharides, such as starch, cellulose and hemicellulose, feedstocks containing disaccharides, such as sucrose, sugarcane juice and sucrose-containing molasses, and monosaccharides, such as glucose and fructose. Suitable feedstocks include starchy crops, such as corn and wheat, sugarcane and sugar beet, molasses and lignocellulosic material. Suitable feedstocks also include algae and microalgae. Where desired, the feedstock may undergo treatments such as comminution, milling, separation of the carbon source from other components, such as proteins, decrystallization, gelatinization, liquefaction, saccharification, and hydrolysis catalyzed by means of chemical and/or enzymatic catalysts. Such treatment can be conducted prior to fermenting or simultaneously with it, e.g. as in simultaneous saccharification and fermentation.

The fermentation broth of the present invention typically has a single liquid phase, but is not necessarily homogeneous since it may contain non-fermented insoluble solids, e.g. in a suspended form. The fermentation feedstock may contain compounds of limited water solubility and optionally also of limited or no fermentability. For example, according to an embodiment of the invention, the fermentation feedstock is comminuted corn and the carbon source is starch contained in it. Possibly, the starch is gelatinized, liquefied and/or saccharified, but insoluble components whether starchy or others (e.g. non-fermented protein) may still exist in the fermentation liquid. According to another embodiment, the fermentation feedstock is a lignocellulosic material and the carbon source is hydrolyzed cellulose and/or hemicellulose. Here again, some of the feedstock components are of limited water solubility. In these and other cases, the fermentation liquid may consist of an aqueous solution of the alcohol with solids suspended in it. Yet, according to an important aspect of the invention, in all those cases, only a single liquid phase exists in the fermentation broth.

A further embodiment of the invention is a method to produce a C3-C6 alcohol that includes hydrolyzing a feedstock that comprises a polysaccharide and at least one other compound to produce fermentable hydrolysis products, a portion of which are fermented in a fermentation medium to produce the C3-C6 alcohol. In this embodiment, the fermentation medium further comprises at least one non-fermented compound. The method further comprises increasing the activity of the C3-C6 alcohol from a portion of the fermentation medium, forming a C3-C6 alcohol-rich liquid phase and a water-rich phase, and separating the C3-C6 alcohol-rich phase from the water-rich phase, as described above in earlier embodiments of the invention. This method further includes separating the at least one non-fermented compound from the fermentation medium, the water-rich phase or both. For example, the at least one non-fermented compound can include a material such as DDGS.

In various embodiments of the invention that include fermentation, the step of fermentation can be conducted simultaneously with other process steps such as various recovery methods disclosed herein, that include the steps of increasing the activity of a C3-C6 alcohol and also the steps of hydrolyzing feed stocks to prepare a fermentation substrate.

In this method, the step of hydrolyzing can include any method capable of breaking polymeric carbohydrates into fermentable products. Thus, the step of hydrolyzing may be chemically or enzymatically catalyzed hydrolysis or autohydrolysis, and saccharification. In this method, the steps of hydrolyzing and fermenting can be conducted simultaneously for at least a portion of time of the method, can be conducted simultaneously for all the time of the method, or can be conducted at distinct times.

In a particular embodiment of this method, the step of fermenting is conducted with a microorganism that is capable of hydrolyzing the feedstock. Suitable microorganisms can be selected from naturally occurring microorganisms, genetically engineered microorganisms and microorganisms developed by classical techniques, or a combination thereof. and have been discussed in detail above.

An alternative embodiment of the present invention is a method to produce a C3-C6 alcohol that includes culturing a microorganism in a fermentation medium to produce the C3-C6 alcohol. The step of culturing is described in detail above. The method further includes increasing the activity of the C3-C6 alcohol in a portion of the fermentation medium and distilling the portion of the fermentation medium to produce a vapor phase comprising water and C3-C6 alcohol and a liquid phase. The steps of increasing the activity and distilling are discussed above in regard to other embodiments of the present invention. The method further includes conducting the liquid phase resulting from the distillation step (the depleted liquid phase) to the fermentation medium. In a preferred embodiment, the portion of the fermentation medium in which the activity of the C3-C6 alcohol is increased comprises microorganisms that remain in the depleted liquid phase and are returned to the fermentation medium for further production of C3-C6 alcohol by the microorganism. In some embodiments, the liquid phase comprises an impurity and the method further includes removing at least a portion of the impurity from at least a portion of the liquid phase before the step of conducting the liquid phase to the fermentation medium. In embodiments of this method, the ratio of the C3-C6 alcohol to water in the portion of the fermentation medium is less than about 10/90 (w/w), less than about 7.5/92.5 (w/w), less than about 5.0/95 (w/w), less than about 2.5/97.5 (w/w), less than about 2/98 (w/w), less than about 1.5/98.5 (w/w), less than about 1/99 (w/w), or less than about 0.5/99.5 (w/w).

A further alternative embodiment of the present invention is a method to recover a C3-C6 alcohol from a dilute aqueous solution comprising the steps of distilling a portion of the dilute aqueous solution to a vapor phase comprising C3-C6 alcohol and water and condensing the vapor phase.

In this embodiment, the vapor phase comprises between about 1% by weight and about 45% by weight of the C3-C6 alcohol that is present in the portion of the dilute aqueous solution. While it is possible to distill more than 45% of the C3-C6 alcohol from the portion of the dilute aqueous solution into the vapor phase, by controlling or limiting the amount of alcohol in the solution that is distilled to the vapor phase (i.e., leaving a significant amount of alcohol behind), a number of important advantages are achieved. As a greater portion of the alcohol in the solution is distilled, the amount of water relative to the amount of alcohol is increased resulting in the need to handle increased water load downstream which can result in increased energy requirements. In addition, for example, in the context of a fermentation, the non-distilled portion of the solution can be returned to the fermentation vessel and used as part of the fermentation medium for production of additional alcohol that can be recovered in a similar process. This process, therefore, is highly efficient because it allows for alcohol recovery in the step of distillation in a range in which the relative amount of alcohol to water is high. In various alternative embodiments, the vapor phase can comprise between about 2% by weight and about 40% by weight of the C3-C6 alcohol, between about 3% by weight and about 35% by weight of the C3-C6 alcohol and between about 4% by weight and about 30% by weight of the C3 C6 alcohol and between about 5% by weight and about 25% by weight of the C3-C6 alcohol present in the portion of the dilute aqueous solution.

In some embodiments, the step of distilling comprises a single stage distillation. Single stage distillation may take place in a flash tank. The design of a flash tank has been described in detail above.

In some embodiments, the ratio of the C3-C6 alcohol to water in the dilute aqueous solution is less than about 10/90 (w/w). In some preferred embodiments, the ratio is less than about 7.5/92.5 (w/w), less than about 5.0/95 (w/w), less than about 2.5/97.5 (w/w), less than about 2/98 (w/w), less than about 1.5/98.5 (w/w), less than about 1/99 (w/w), or less than about 0.5/99.5 (w/w).

The step of distilling may be adiabatic or isothermal. In adiabatic distilling no significant heat transfer takes place between the distillation system and the surroundings, and the pressure of the system is held constant. In isothermal distilling heat transfer is allowed between the distillation system and the surroundings, and the temperature of the system is held constant.

In various embodiments of this method, the enrichment of alcohol from the dilute aqueous solution to the vapor is at least about 5 fold, about 6 fold, about 7 fold, about 8 fold, about 9 fold, about 10 fold, about 11 fold, about 12 fold, about 13 fold, about 14 fold or about 15 fold. The term "enrichment" refers to the ratio of alcohol/water in the condensed vapor divided by the ratio of alcohol/water in the aqueous dilute solution.

In some embodiments, the method further comprises the step of forming a C3-C6 alcohol-rich liquid phase and a water-rich liquid phase from the portion of the dilute aqueous solution. In some embodiments, the method further comprises separating the C3 C6 alcohol-rich phase and the water-rich phase. The steps of forming an alcohol-rich liquid phase and a water-rich liquid phase, and of separating the two have been discussed in detail above.

A further alternative embodiment of the present invention is a method to produce a product from a C3-C6 alcohol in a dilute aqueous solution, such as a fermentation broth comprising microorganisms and the C3-C6 alcohol. This method includes distilling a vapor phase comprising water and C3-C6 alcohol from the dilute aqueous solution and reacting the C3-C6 alcohol in the vapor phase to form the product. This embodiment further comprises other process steps disclosed herein leading to the formation of the vapor phase.

An embodiment of the present invention is shown in FIG. 1. Fermentation is conducted in fermentor 10. The fermentation broth in the fermentor 10 includes the C3-C6 alcohol product, such as butanol, and other components of the fermentation medium. During the course of the fermentation, a stream of the fermentation broth, which may include microorganisms, is conducted from the fermentor 10 to a heat exchanger 20 via 12. The heat exchanger 20 is used to raise the temperature of the fermentation broth to a temperature suitable for a subsequent distillation. After the temperature of the fermentation broth is raised to an appropriate temperature, the broth is further conducted to a flash tank 30 for distillation via 22. The fermentation heat can partially supply the heat required for vaporization in the flash system. The flash tank 30 is maintained at a below atmospheric pressure so that upon introduction of the heated fermentation broth into the flash tank 30, a portion of the fermentation broth gets vaporized. The portion of the vaporized fermentation broth includes only a portion of the butanol in the fermentation broth along with water vapor. After distillation in the flash tank 30, the remaining portion of the fermentation broth that is not distilled is returned to the fermentor 10 via 34. This fermentation broth that is being returned to the fermentor is now partially depleted of butanol. The portion of the fermentation broth that is vaporized in the flash tank 30 is conducted as a vapor to a vapor condenser 40 via 32, which can be cooled, for example, by chilled water via 42. Upon condensation of the mixed butanol and water vapor, the condensed solution is conducted to a phase separator 50 via 44. The remaining vapor that is not condensed is then further conducted to an outlet via 48. The condensed solution in the phase separator is allowed to separate into a heavy liquid phase and a light liquid phase. The heavy liquid phase consists primarily of water with some amount of butanol soluble in the water. The light phase consists primarily of butanol with some amount of soluble water. From the phase separator, the light phase containing butanol can be recovered by separation from the heavy phase and can be treated for further purification. The heavy phase consisting primarily of water can be conducted for other applications or uses in the system. 13, 35 are liquid pumps and 47 is a vacuum pump.

Figure 2:
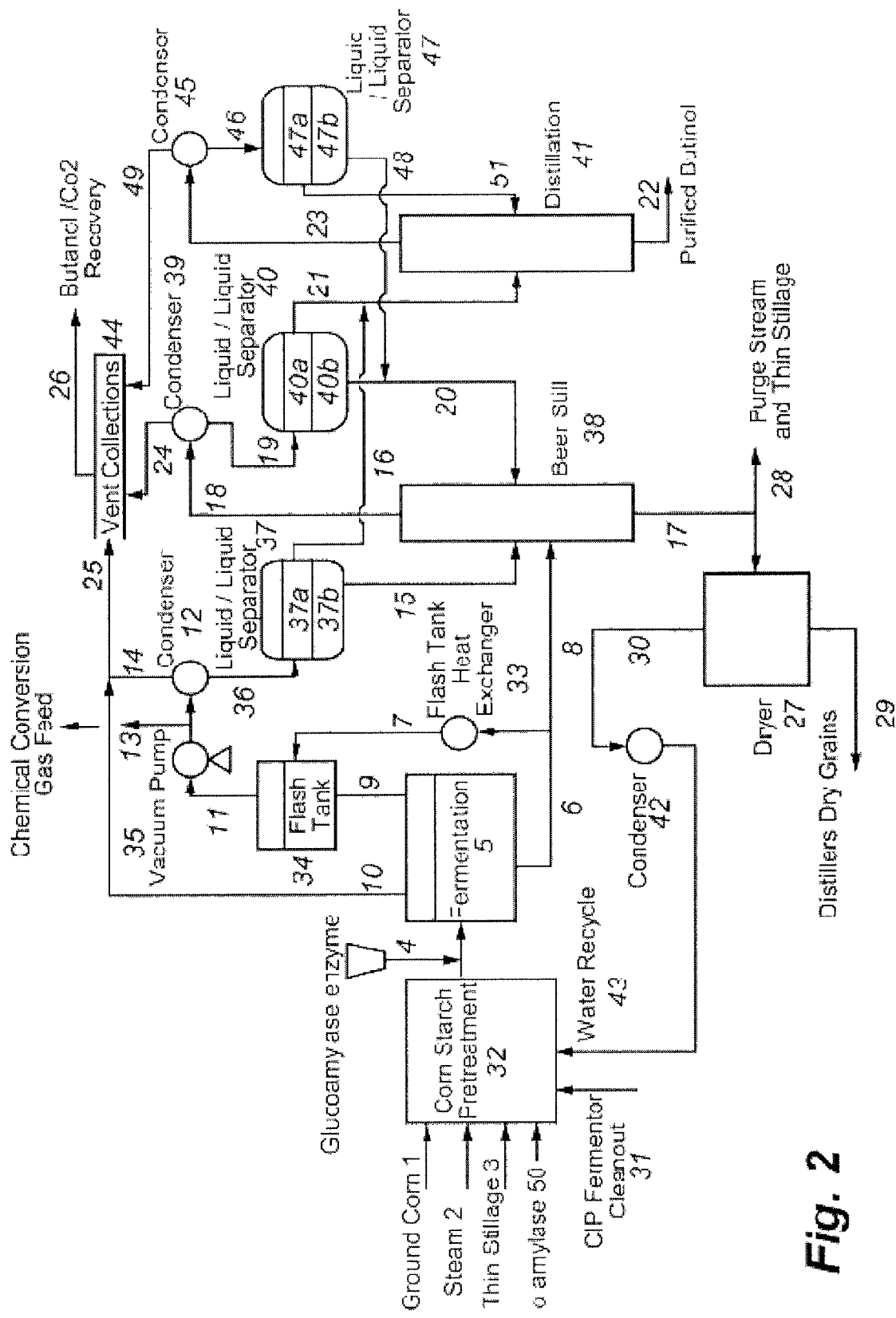
FIG. 2 represents an embodiment of the present invention for the production and recovery of butanol from fermentation broth in a process of simultaneous saccharification and fermentation of pretreated corn.

With reference to FIG. 2, a specific embodiment of the present invention is presented, illustrating the production of butanol by simultaneous saccharification and fermentation of pretreated corn, and azeotropic distillation of a side stream of butanol. Dry corn is milled into a fine powder. The milled (ground) corn 1, thin stillage 3, CIP fermentor cleanout 31, recycled water 43, and steam 2 are added to a corn starch pretreatment system 32 where the mixture is slurried and heated to about 99° C. (A CIP (Clean in Place) fermentor cleanout is a caustic water solution that is used to clean and sanitize the fermentors between batches. NaOH is often used but other strong bases and other sanitization chemicals can also be used. The waste CIP solution contains solids, nutrients, carbohydrates etc from the fermentor (clinging to walls) that can be reintroduced into the front end of the corn pretreatment.) Alpha-amylase 50 is added to the corn starch pretreatment system 32 where the holding time can be about 1 hour or less. Glucoamylase enzyme 4 is added after the solution is cooled to a temperature ranging from about 50° C. to about 65° C. After a short saccharification time of about 5-6 hours the slurry is cooled to about 32° C. The slurry solids concentration at this point can be about 361 g/kg, including insoluble and soluble solids. Enzymes 4 sufficient to complete the saccharification in about 32 hours are also added to the corn mash mixture, which is transferred to the fermentor 5. The fermentation is run under simultaneous saccharification and fermentation (SSF) mode at 32° C. A side stream 6 containing about 4 wt. % butanol is continuously removed from the fermentor 5 and a flash tank heat exchanger 33 is used to control the temperature of a flash tank feed 7 at about 34° C. Vacuum of about 50 mm Hg is pulled on a flash tank 34 and an azeotropic vapor composition 11 is formed. The composition of the butanol water vapor azeotrope 11 can be about 54 wt % butanol and about 46 wt % water. The azeotrope vapor 11 is pumped by the vacuum pump 35 and is either fed to a chemical conversion process 13 or to a condenser 12. The condensed vapor phase 36 is conducted to a liquid/liquid separator 37 where it is phase separated. The condensed vapor phase separates into a butanol rich phase 37a and a water rich phase 37b. The butanol rich phase 37a has a butanol concentration of about 680 g/L butanol. The water rich phase 37b has a butanol concentration of about 86 g/L. The ratio of the volumes produced for the upper layer 37a to the lower layer 37b is 3 to 1.

The unvaporized components 9 in the flash tank 34 including cells, water, nutrients, carbohydrates, and about 2 wt % unvaporized butanol are returned to the fermentor 5. The unvaporized components 9 are depleted of butanol and when returned to the fermentor 5, can continue to produce butanol to be recovered by treatment of the side stream 6 as described above.

The water rich heavy phase 37b from the liquid/liquid separator 37 is conducted 15 to a beer still 38 and distilled. A butanol-water azeotropic composition 18 is generated in the beer still 38 and is conducted to a condenser 39 to be condensed. The condensed vapor 19 is conducted to a liquid/liquid separator 40 to be separated into a water rich heavy phase 40b and a butanol rich light phase 40a. The water rich heavy phase 40b contains about 86 g/L butanol is recycled 20 back to the beer still 38. The butanol rich phase 40a has a butanol concentration of about 680 g/L butanol.

The butanol rich light phase 40a in the liquid/liquid separator 40 is conducted 21 to a distillation system 41. The butanol rich light phase 37a in the liquid/liquid separator 37 is also conducted 16 to the distillation system 41, and can be combined with the butanol rich light phase 40a. The distillation system 41 is operated at atmospheric pressure and purified butanol is produced as a high boiling product 22 at a concentration of about 99 wt % butanol. (In other embodiments, the distillation system can be operated at sub atmospheric, atmospheric, or super atmospheric pressures.) A butanol water azeotrope vapor 23 is produced and sent to the condenser 45 and condensed. The condensed vapor 46 is conducted to a liquid/liquid separator 47 to be separated into a water rich heavy phase 47b and a butanol rich light phase 47a. The water rich heavy phase 47b is recycled 48 to the beer still 38. The butanol rich light phase 47a is conducted 51 to the distillation system 41 and can be combined with other inputs 16, 21.

The SSF fermentation in the fermentor 5 is conducted for 52 hours. The fermentation broth containing about 2% butanol that is not removed by the vacuum flash tank 34 is conducted 8 to the beer still 38. The butanol in the broth is distilled overhead as a butanol-water azeotrope 18. From the beer still 38, water, unconverted carbohydrates, nutrients, cells, fiber, corn germ, enzymes, and other fermentation components are taken as a bottoms product 17 and contains about 0.05 wt % butanol. The beer still bottoms stream 17 is divided to a distillers dry grain dryer 27 and a purge stream 28. Thin stillage 3 is produced by the purge stream 28. Dried distillers grains 29 are produced by the dryer 27. The dryer 27 also produces water vapor 30 that is condensed by a condenser 42 and recycled 43 to the corn starch pretreatment system 32.

The fermentor 5, condenser 12 (having an inflow from the flash tank 34), condenser 39 (having an inflow from the beer still 38), and condenser 45 (having an inflow from the distillation system 41) have vent streams 10, 25, 24, 49 that contain butanol, water, $CO_2$, and other inert gases. These streams are combined in a vent collection system 44 and are processed in downstream equipment 26 to recover and purify butanol and $CO_2$.

The foregoing embodiment of the invention can be conducted in a retrofit corn ethanol production plant in which the primary operations, including corn starch pretreatment system, fermentor, beer still, distillation system, and dryer are operations that previously were used to produce ethanol. Such systems have multiple fermentors (typically from five to seven) that are operated in cycle so that each one conducts a fermentation for about 52 hours before being emptied into a beer still. The operations upstream of the fermentors (e.g., the corn starch pretreatment system) operate essentially continuously preparing a feedstock for a first fermentor and then preparing a feedstock for a second fermentor and so forth. The operations downstream of the fermentors (e.g., the beer still, distillation system, and dryer) operate essentially continuously taking the fermentation broth from each fermentor as it finishes a fermentation cycle to recover ethanol, produce DDGS, a purge stream and thin stillage.

Such an ethanol production plant can be retrofitted to produce butanol by incorporating various production and recovery processes as described herein. Typically, microorganisms that produce ethanol are tolerant to high concentrations of ethanol in the fermentation broth. However, high concentrations of C3-C6 alcohols in the fermentation broth can be toxic to microorganisms. Therefore, a low cost method to simultaneously remove alcohols as they are produced is required to operate an ethanol plant to produce a C3-C6 alcohol instead of ethanol.

Since butanol concentrations cannot be generated that are as high as ethanol concentrations before butanol production organisms shut down, the production and recovery processes described herein are useful for incorporation into an ethanol plant to allow efficient production of butanol. By incorporating butanol recovery processes in which a portion of a fermentation broth that can include microorganisms is taken to a recovery operation such as a flash tank for recovery of a portion of the butanol from the portion of the fermentation broth and returning a butanol-depleted stream to a fermentor, the effective butanol concentration of the fermentation can be significantly increased so that a butanol production process can be conducted into an ethanol production plant.

The process of retrofitting a plant can include introducing equipment to produce a side stream 6, flash tank feed 7, and unvaporized components stream 9, as described above into a plant. In addition, equipment for conducting liquid/liquid separations such as separators 37, 40, can be introduced to provide for efficient recovery of butanol.

Accordingly, in one embodiment, the present invention includes a method to operate a retrofit ethanol production plant to produce a C3-C6 alcohol. In this embodiment, the retrofit ethanol production plant comprises a pretreatment unit, multiple fermentation units, and a beer still to produce the C3-C6 alcohol. The method includes the steps of pretreating a feedstock to form fermentable sugars in the pretreatment unit; fermenting the fermentable sugars with a microorganism that produces the C3-C6 alcohol in a fermentation medium in a first fermentation unit; treating a portion of the fermentation medium to remove the C3-C6 alcohol; returning the treated portion to the first fermentation unit; and transferring the fermentation medium from the first fermentation unit to the beer still.

The method includes the step of pretreating a feedstock to form fermentable sugars in the pretreatment unit. The pretreatment unit continuously receives the feedstock for pretreatment. The term pretreatment refers to treatments such as comminution, milling, separation of the carbon source from other components such as proteins, decrystallization, gelatinization, liquefaction, saccharification, and hydrolysis catalyzed by means of chemical and/or enzymatic catalysts. For example, the feedstock may be dry corn which may be ground, mixed with water, heated and reacted with amylases in the pretreatment unit to produce a mash or slurry containing fermentable sugars that are suitable as substrate for fermentation by microorganisms.

The method further includes the step of fermenting the fermentable sugars with a microorganism that produces the C3-C6 alcohol in a fermentation medium in a first fermentation unit. A fermentation unit contains fermentation medium comprising microorganisms that are capable of converting the fermentable sugars into the C3-C6 alcohol. Such microorganisms have been described in detail above. The retrofit plant comprises multiple fermentation units. A stream of the pretreated feedstock containing fermentable sugars from the pretreatment unit is introduced into the first fermentation unit, where it is combined with the fermentation medium comprising microorganisms. The microorganisms ferment the fermentable sugars present to produce the C3-C6 alcohol.

The method further includes the step of treating a portion of the fermentation medium to remove the C3-C6 alcohol. The fermentation medium comprises the C3-C6 alcohol, water, as well as the microorganisms. A portion (e.g., a side stream) of the fermentation medium from the first fermentation unit is taken to remove the C3-C6 alcohol contained therein. Treating can include any one or more of the methods for purification and recovery of C3-C6 alcohols from dilute aqueous solutions described herein and specifically, can include the steps of distilling a vapor phase comprising water and C3-C6 alcohol, addition of a hydrophilic solute, addition of a water soluble carbon source, reverse osmosis, and dialysis, and mixtures thereof, all of which steps have been described in detail above. In a preferred embodiment, this step comprises directing a sidestream from the first fermentation unit to a flash tank where the step of distilling is conducted at below atmospheric pressures. The design of a flash tank has been described in detail above.

The method further includes the step of returning the treated portion to the first fermentation unit. The treated portion is depleted in the C3-C6 alcohol and comprises water and can include microorganisms, both of which are returned to the fermentation medium. By removing a portion of the C3-C6 alcohol from fermentation medium and returning the medium to the fermentor, the concentration of the C3-C6 alcohol in the fermentation broth is maintained below a concentration that is detrimental to further production of the C3-C6 alcohol.

The method further includes the step of transferring the fermentation medium from the fermentation unit to a beer still. This step is conducted when it is desired to have the fermentation completed. Fermentation completion occurs when all fermentable carbohydrates are consumed or when the rate of carbohydrate conversion is reduced such that termination of the fermentation is desired.

In some embodiments of this method, the rate of pretreating is the same as for the plant when it produced ethanol and/or the same as for conventional ethanol plants. As used herein, reference to a rate being the "same" includes the rate being identically the same, but also being within (plus or minus) about 25% of the rate, within about 15% of the rate, within about 10% of the rate, within about 9% of the rate, within about 8% of the rate, within about 7% of the rate, within about 6% of the rate, within about 5% of the rate, within about 4% of the rate, within about 3% of the rate, within about 2% of the rate, within about 1% of the rate. Thus, if the retrofit ethanol plant had a pretreatment rate of about 115 metric tons per hour, a pretreatment rate within about 25% of that rate would include a rate from about 7.5 tons per hour to about 12.5 tons per hour. The rate of pretreating refers to the rate at which pretreated feedstock is conducted to a fermentation unit.

In some other embodiments of this method, the cycle time for a fermentation unit is the same as for the plant when it produced ethanol and/or the same as for conventional ethanol plants. The cycle time refers to the time from introduction of an inoculum to the time of emptying the fermentor to a beer still. For example, a typical cycle time for a fermentor is about 52 hours.

In one embodiment, the C3-C6 alcohol output of the retrofit plant is at least about 80% of the C3-C6 alcohol equivalent of the ethanol maximum output of the plant before retrofit. In other embodiments, the C3-C6 alcohol output of the retrofit plant is at least about 81%, at least about 82%, at least about 83%, at least about 84%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, at least about 99% of the C3-C6 alcohol equivalent of the ethanol maximum output of the plant before retrofit.

The maximum output of an alcohol plant is a measure of the amount of alcohol produced by that plant, and may be expressed as gallons of alcohol produced per year or other units measuring volume or weight per time period. The output of a plant depends on the size and design of the specific plant. The term "ethanol maximum output of the plant before retrofit" refers to the maximum amount of ethanol produced by a plant or for which the plant was engineered before it is retrofit to produce a C3-C6 alcohol.

As recognized above, microorganisms used for production of ethanol are tolerant to high concentrations of ethanol in the fermentation broth, but microorganisms used for production of C3-C6 alcohols are typically not tolerant to high concentrations of C3-C6 alcohols. Advantageously, using the methods of the present invention it is possible to retrofit an ethanol plant to produce a C3-C6 alcohol at output levels comparable to that of ethanol, limited only by the theoretical conversion efficiency of that particular alcohol. The theoretical conversion efficiency of glucose to ethanol, on a weight basis, is 51% or 0.51. (In practice however, some of the glucose is used by the micro-organisms for production of cell mass and metabolic products other than the alcohol, and the actual conversion efficiency is less than the theoretical maximum.) Depending on the fermentation pathway used by the microorganism, the theoretical conversion efficiency of glucose to propanol can range from 0.33 to 0.44, that of butanol can range from 0.27 to 0.41, that of pentanol can range from 0.33 to 0.39, and that of hexanol can range from 0.28 to 0.38. The term "C3-C6 alcohol equivalent" refers to the ratio of the theoretical conversion efficiency of a particular C3-C6 alcohol to that of ethanol and is specific for the fermentation pathway used. Thus, the "iso-butanol equivalent of ethanol" (for the pathway in which one molecule of glucose is broken into one molecule of isobutanol, two molecules of ATP and two molecules of $CO_2$) as used herein is 0.401÷0.51=0.806. For example, consider an ethanol plant with an ethanol maximum output of the plant before retrofit of about 100 million gallons/year. Using the methods of the present invention, it is possible to retrofit the plant and operate it to produce butanol at a theoretical maximum output of about 80.6 million gallons per year. However, given that the density of ethanol is 0.7894 and the density of isobutanol is 0.8106, the actual theoretical maximum output of isobutanol is about 78 million gallons per year. The exact number of gallons per year can be calculated using the density information, the theoretical yields and/or the actual practical yields achieved.

In various embodiments, an ethanol plant can be retrofit and operated at an output of at least about 80% of the theoretical maximum output for any given C3-C6 alcohol, accounting for density differences. In other embodiments, the C3-C6 alcohol output of the retrofit plant could be at least about 81%, at least about 82%, at least about 83%, at least about 84%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, at least about 99% of theoretical maximum output, accounting for density differences.

Another embodiment of the invention is a method for extraction of a C3-C6 alcohol from an aqueous solution that includes contacting an aqueous solution with an acidic, amine-based extractant. The acidic amine-based extractant can be formed by acidifying an organic amine solution as described above. Upon contact of the aqueous solution with the extractant, the extraction is carried out by mixing the acidic, amine-based extractant with the aqueous solution. The C3-C6 alcohol can be recovered from an extractant phase that forms after contact.

Various aspects of the invention are described in detail in the examples provided below. However, these examples are provided for the purpose of illustration and are not intended to limit the scope of the present invention. Each publication and reference cited herein is incorporated herein by reference in its entirety. While various embodiments of the present invention have been described in detail, it is apparent that modifications and adaptations of those embodiments will occur to those skilled in the art. It is to be expressly understood, however, that such modifications and adaptations are within the scope of the present invention, as set forth in the following exemplary claims.

EXAMPLES

Example 1

Enrichment of C3-C6 Alcohols from Aqueous Solutions Using Solvents

This example illustrates the enrichment of C3-C6 alcohols, such as propanol (PrOH), butanol (BuOH), isobutanol (i-BuOH) and pentanol (PenOH), from aqueous solutions using various solvents.

Several aqueous solutions were prepared for each alcohol, differing in their alcohol concentrations, all of which were sub-saturated. Each of those aqueous solutions was mixed with a solvent, such as butylacetate, tributylphosphate, decanol, 2-heptanone or octane. The phase ratio between the aqueous solution and the solvent differed from one case to the other. Mixing was continued until equilibrium was reached. At equilibrium, phase separation could be observed forming an upper, alcohol-rich phase (light phase) and a lower, alcohol-lean phase (heavy phase). Both phases were analyzed for alcohol and water content. The alcohol concentrations were analyzed by high pressure liquid chromatography (HPLC) at 25° C. using a YMC-Pack ODS-AM column The eluents were methanol-water solutions, in which the methanol concentration was 20%, 30%, 30% and 40% for propanol, butanol, isobutanol and pentanol, respectively. The water content of the organic phases was determined by the Karl-Fischer method. These analytical methods were also used for the analyses in the other examples.

The distribution coefficient of the alcohol was calculated for each experiment by dividing the alcohol concentration in the light phase by the alcohol concentration in the heavy phase. Similarly, the distribution coefficient for water was calculated by dividing the water concentration in the light phase by the water concentration in the heavy phase. The enrichment factor was calculated by dividing the distribution coefficient of alcohol by the distribution coefficient of water. In addition, the alcohol to water ratio (w/w) was calculated for the light phase. The results are reported in tables 1.1 to 1.8.

TABLE 1.1

Enrichment of isobutanol (i-BuOH) by contact with butyl acetate at 25° C.

| Light phase | | | Heavy phase | | | Distribution coefficients | | Enrichment factor |
|---|---|---|---|---|---|---|---|---|
| i-BuOH Wt % | $H_2O$ Wt % | i-BuOH/$H_2O$ w/w | i-BuOH Wt % | $H_2O$ Wt % | Butyl acetate Wt % | i-BuOH Da | $H_2O$ Dw | |
| 0.83 | 1.3 | 0.63 | 0.34 | 99.7 | 0.39 | 2.5 | 0.013 | 187 |
| 3.1 | 1.9 | 1.7 | 1.5 | 98.4 | 0.31 | 2.0 | 0.019 | 105 |
| 4.4 | 3.1 | 1.4 | 2.5 | 97.5 | 0.34 | 1.8 | 0.032 | 57 |

TABLE 1.2

Enrichment of iso-butanol (i-BuOH) by contact with tri-butyl phosphate (TBP) at 25° C.

| Light phase | | | Heavy phase | | | Distribution coefficients | | Enrichment factor |
|---|---|---|---|---|---|---|---|---|
| i-BuOH Wt % | $H_2O$ Wt % | i-BuOH/$H_2O$ w/w | i-BuOH Wt % | $H_2O$ Wt % | TBP Wt % | i-BuOH Da | $H_2O$ Dw | |
| 1.2 | 7.1 | 0.17 | 0.22 | 99.8 | 0.016 | 5.4 | 0.071 | 76 |
| 5.6 | 6.5 | 0.86 | 1.2 | 98.8 | 0.023 | 4.9 | 0.066 | 74 |
| 9.8 | 6.3 | 1.6 | 1.9 | 98.1 | 0.024 | 5.2 | 0.064 | 82 |

TABLE 1.3

Enrichment of iso-butanol (i-BuOH) by contact with decanol at 25° C.

| Light phase | | | Heavy phase | | | Distribution coefficients | | Enrichment factor |
|---|---|---|---|---|---|---|---|---|
| i-BuOH Wt % | $H_2O$ Wt % | i-BuOH/$H_2O$ w/w | i-BuOH Wt % | $H_2O$ Wt % | Decanol Wt % | i-BuOH Da | $H_2O$ Dw | |
| 1.11 | 3.8 | 0.29 | 0.30 | 99.7 | 0.0020 | 3.8 | 0.038 | 99 |
| 7.5 | 4.4 | 1.7 | 1.4 | 98.6 | 0.0043 | 5.2 | 0.045 | 116 |
| 12.0 | 4.6 | 2.6 | 2.2 | 97.8 | 0.0053 | 5.5 | 0.047 | 119 |

TABLE 1.4

Enrichment of iso-butanol (i-BuOH) by contact with 2-Heptanone at 25° C.

| Light phase | | | Heavy phase | | | Distribution coefficients | | Enrichment factor |
|---|---|---|---|---|---|---|---|---|
| i-BuOH Wt % | $H_2O$ Wt % | i-BuOH/$H_2O$ w/w | i-BuOH Wt % | $H_2O$ Wt % | 2-Heptanone Wt % | i-BuOH Da | $H_2O$ Dw | |
| 1.15 | 1.7 | 0.68 | 0.44 | 99.2 | 0.40 | 2.6 | 0.017 | 155 |
| 5.4 | 2.5 | 2.2 | 1.7 | 98.0 | 0.34 | 3.3 | 0.026 | 125 |
| 8.4 | 3.5 | 2.4 | 2.0 | 97.7 | 0.29 | 4.1 | 0.036 | 116 |

TABLE 1.5

Enrichment of propanol (PrOH) by contact with octane at 24° C.

| PrOH in light phase Wt % | Water in the light phase Wt % | PrOH in heavy phase Wt % | Water in the heavy phase Wt % | Da | Dw | Enrichment factor |
|---|---|---|---|---|---|---|
| 0.03 | <0.05 | 0.66 | 99.3 | 0.047 | <0.0005 | >100 |
| 0.07 | <0.05 | 1.9 | 98 | 0.037 | <0.0005 | >80 |
| 0.24 | <0.05 | 5.7 | 94.3 | 0.042 | <0.0005 | >80 |

TABLE 1.6

Enrichment of iso-butanol (i-BuOH) by contact with octane at 24° C.

| Light phase | | | Heavy phase | | Distribution coefficients | | Enrichment factor |
|---|---|---|---|---|---|---|---|
| i-BuOH Wt % | $H_2O$ Wt % | i-BuOH/ $H_2O$ w/w | i-BuOH Wt % | $H_2O$ Wt % | i-BuOH Da | $H_2O$ Dw | |
| 0.10 | 0.048 | 2.1 | 0.64 | 99.4 | 0.15 | 0.0005 | 300 |
| 0.30 | 0.059 | 5.1 | 1.9 | 98.1 | 0.16 | 0.0006 | 250 |
| 2.5 | 0.076 | 33 | 4.6 | 95.4 | 0.54 | 0.0008 | 650 |

TABLE 1.7

Enrichment of butanol (BuOH) by contact with octane at 24° C.

| Light phase | | | Heavy phase | | Distribution coefficients | | Enrichment factor |
|---|---|---|---|---|---|---|---|
| BuOH Wt % | $H_2O$ Wt % | BuOH/ $H_2O$ w/w | BuOH Wt % | $H_2O$ Wt % | BuOH Da | $H_2O$ Dw | |
| 0.11 | 0.06 | 1.8 | 0.65 | 99.4 | 0.17 | 0.0006 | 250 |
| 0.29 | 0.05 | 5.9 | 1.8 | 98.2 | 0.16 | 0.0005 | 300 |
| 2.5 | 0.07 | 36 | 4.6 | 95.4 | 0.55 | 0.0008 | 650 |

TABLE 1.8

Enrichment of Pentanol (PenOH) by contact with octane at 24° C.

| Light phase | | | Heavy phase | | Distribution coefficients | | Enrichment factor |
|---|---|---|---|---|---|---|---|
| PenOH Wt % | $H_2O$ Wt % | PenOH/ $H_2O$ w/w | PenOH Wt % | $H_2O$ Wt % | PenOH Da | $H_2O$ Dw | |
| 0.63 | 0.06 | 10.5 | 0.59 | 99.4 | 1.08 | 0.006 | 180 |
| 2.95 | 0.08 | 37 | 1.5 | 98.5 | 2.0 | 0.03 | 67 |
| 12.6 | 0.50 | 25 | 2.7 | 97.3 | 4.6 | 0.13 | 35 |

The results show that the enrichment is dependent on the alcohol and on the selected solvent. For example, for the lower molecular weight alcohols, the more polar solvents, such as butyl acetate and tri-butyl phosphate had higher distribution coefficients compared with those of a less polar solvent, such as octane. On extraction by octane, alcohols with higher molecular weights extracted better. For a given alcohol and solvent combination, the distribution coefficients and the enrichment factor were dependent on the alcohol concentration in the equilibrium aqueous phase. Yet, for all tested solvents a high enrichment factor was observed. The light or upper phase was the alcohol-rich phase in all cases. The alcohol to water ratio was 50 to 600 times higher in the light phase as compared to the heavy phase.

Example 2

Extraction of Isobutanol from Aqueous Solutions Using Solvents

This example illustrates the efficiency of the enrichment of isobutanol from sub-saturated aqueous solutions using various solvents. Table 2 summarizes the results of various isobutanol enrichment experiments. Isobutanol was extracted from aqueous solutions of various starting concentrations. Several solvents were used to carry out a single step extraction at 25° C. In addition, the solvent phase to aqueous phase ratio was varied. The isobutanol concentration in the solvent was measured for each experiment and the extraction yield was calculated for each experiment by dividing the alcohol amount in the solvent by the initial alcohol amount in the aqueous solution.

TABLE 2

Enrichment of i-BuOH from aqueous solutions of various concentrations with several extractants: butyl acetate (BuAc), decanol (DeOH), tri-butyl-phosphate (TBP) and 2-heptanone.

| Initial i-BuOH conc. (Wt %) in aqueous solution | Solvent | Solvent/aqueous solution (w/w ratio) | Final i-BuOH conc. (Wt %) in aqueous solution | i-BuOH conc. (Wt %) in solvent solution | Extraction yield (%) |
|---|---|---|---|---|---|
| 0.7 | butyl acetate | 0.5 | 0.3 | 0.8 | 60 |
| 0.8 | decanol | 0.5 | 0.3 | 1.1 | 60 |
| 1.0 | 2-Heptanone | 0.5 | 0.4 | 1.1 | 60 |
| 1.4 | tri-butyl phosphate | 1.0 | 0.2 | 1.2 | 85 |
| 1.6 | 2-Heptanone | 1.0 | 0.4 | 1.1 | 75 |
| 2.0 | butyl acetate | 2.0 | 0.3 | 0.8 | 85 |
| 2.5 | decanol | 2.0 | 0.3 | 1.1 | 85 |
| 2.6 | tri-butyl phosphate | 2.0 | 0.2 | 1.2 | 90 |
| 2.7 | 2-Heptanone | 2.0 | 0.4 | 1.1 | 85 |
| 3.0 | butyl acetate | 0.5 | 1.5 | 3.1 | 50 |
| 4.0 | tri-butyl phosphate | 0.5 | 1.1 | 5.6 | 72 |
| 4.4 | 2-Heptanone | 0.5 | 1.7 | 5.4 | 61 |
| 4.6 | butyl acetate | 1.0 | 1.5 | 3.1 | 67 |
| 4.7 | butyl acetate | 0.5 | 2.5 | 4.4 | 47 |

TABLE 2-continued

Enrichment of i-BuOH from aqueous solutions of various concentrations with several extractants: butyl acetate (BuAc), decanol (DeOH), tri-butyl-phosphate (TBP) and 2-heptanone.

| Initial i-BuOH conc. (Wt %) in aqueous solution | Solvent | Solvent/aqueous solution (w/w ratio) | Final i-BuOH conc. (Wt %) in aqueous solution | i-BuOH conc. (Wt %) in solvent solution | Extraction yield (%) |
|---|---|---|---|---|---|
| 5.1 | decanol | 0.5 | 1.4 | 7.5 | 73 |
| 8.0 | butyl acetate | 1.5 | 2.1 | 3.9 | 80 |
| 8.0 | tri-butyl phosphate | 1.3 | 1.1 | 5.6 | 80 |
| 8.0 | decanol | 1.7 | 0.8 | 4.2 | 80 |
| 8.0 | 2-Heptanone | 0.7 | 2.0 | 8.4 | 90 |
| 8.0 | tri-butyl phosphate | 0.6 | 1.9 | 9.8 | 90 |
| 8.0 | decanol | 0.5 | 2.2 | 12.0 | 95 |

The experiments showed that high extraction yield values could be reached. These high extraction yield values were not limited to high isobutanol starting concentrations or to high solvent phase to aqueous phase ratios. The high extraction yield values could be observed for both, low isobutanol starting concentrations and low proportions of solvent used.

Furthermore, the experiments showed that the concentration of isobutanol in the aqueous phase can be reduced to very low amounts even when starting with a saturated isobutanol solution. This allows recycling of an aqueous stream into the front end of a fermentation without limiting the alcohol productivity of the micro-organisms, since presence of high concentrations of alcohol in the fermentation broth can adversely impact the ability of the micro-organisms to produce alcohol.

Example 3

Enrichment of C3-C6 Alcohols from Aqueous Solutions Using Gasoline

This example illustrates the enrichment of C3-C6 alcohols from aqueous solutions by contacting with gasoline.

Aqueous solutions of C3-C6 alcohols, including propanol (PrOH), butanol (BuOH), isobutanol (i-BuOH) and pentanol (PenOH), were prepared and mixed with gasoline until equilibrium was reached. The gasoline used was commercial grade with a 95 octane rating. At equilibrium, the mixture formed an upper alcohol rich phase (light 5 phase) and a lower alcohol lean phase (heavy phase). Both phases were analyzed for alcohol and water content. The distribution coefficient of the alcohol was calculated for each experiment by dividing the alcohol concentration in the light phase by the concentration in the heavy phase. Similarly, the distribution coefficient for water was calculated by dividing the water concentration in the light phase by the water concentration in the heavy phase. The enrichment factor was calculated by dividing the distribution coefficient of alcohol by the distribution coefficient of water. All experiments were carried out at 24° C. The results are reported in Tables 3.1 to 3.4.

TABLE 3.1

Enrichment of 1-butanol (BuOH) by contact with gasoline at 24° C.

| Light phase composition | | Heavy phase composition | | Distribution coefficients | | Enrichment factor |
|---|---|---|---|---|---|---|
| BuOH Wt % | H$_2$O Wt % | BuOH Wt % | H$_2$O Wt % | BuOH Da | H$_2$O Dw | |
| 0.34 | 0.04 | 0.55 | 99.5 | 0.62 | 0.0004 | >1000 |
| 1.27 | 0.10 | 1.64 | 98.4 | 0.77 | 0.001 | 770 |
| 7.3 | 0.34 | 3.8 | 96.2 | 1.9 | 0.0036 | 540 |

TABLE 3.2

Enrichment of iso-butanol (i-BuOH) by contact with gasoline at 24° C.

| Light phase composition | | | Heavy phase composition | | Distribution coefficients | | Enrichment factor |
|---|---|---|---|---|---|---|---|
| i-BuOH Wt % | H$_2$O Wt % | gasoline Wt % | i-BuOH Wt % | H$_2$O Wt % | i-BuOH Da | H$_2$O Dw | |
| 0.38 | 0.08 | 99.6 | 0.58 | 99.4 | 0.66 | 0.0008 | 800 |
| 1.05 | 0.11 | 98.8 | 1.62 | 98.4 | 0.65 | 0.0011 | 600 |
| 1.71 | 0.12 | 98.2 | 2.15 | 97.8 | 0.80 | 0.0012 | 700 |
| 5.00 | 0.34 | 94.7 | 3.07 | 96.9 | 1.63 | 0.0035 | 460 |
| 6.1 | 0.33 | 93.5 | 3.96 | 96.0 | 1.55 | 0.0034 | 450 |
| 15.8 | 1.20 | 83.0 | 4.4 | 95.6 | 3.6 | 0.012 | 300 |
| 23.0 | 2.0 | 75.0 | 4.7 | 95.3 | 4.8 | 0.021 | 230 |
| 33.0 | 2.7 | 64.3 | 5.3 | 94.7 | 6.3 | 0.028 | 220 |
| 49 | 5.2 | 45.8 | 6.8 | 93.2 | 7.2 | 0.056 | 130 |
| 57 | 6.7 | 36.1 | 7.2 | 92.8 | 7.9 | 0.072 | 110 |
| 65 | 7.6 | 26.9 | 7.4 | 92.6 | 8.8 | 0.082 | 100 |
| 62 | 7.9 | 29.7 | 7.3 | 92.7 | 8.6 | 0.085 | 100 |
| 80 | 14.2 | 5.9 | (1) | (1) | | | |
| 75 | 11.1 | 13.7 | (1) | (1) | | | |

(1) not enough heavy phase formed to be analyzed.

TABLE 3.3

Enrichment of Pentanol (PenOH) by contact with gasoline at 24° C.

| Light phase composition | | Heavy phase composition | | Distribution coefficients | | Enrichment factor |
|---|---|---|---|---|---|---|
| PenOH Wt % | H$_2$O Wt % | PenOH Wt % | H$_2$O Wt % | PenOH Da | H$_2$O Dw | |
| 1.00 | 0.10 | 0.60 | 99.4 | 1.68 | 0.001 | >1000 |
| 4.9 | 0.33 | 1.15 | 98.8 | 4.2 | 0.0033 | >1000 |
| 17.8 | 1.52 | 2.7 | 97.3 | 6.6 | 0.016 | 400 |

TABLE 3.4

Enrichment of propanol (PrOH) by contact with gasoline at 24° C.

| PrOH in light phase Wt % | Water in the light phase Wt % | PrOH in heavy phase Wt % | Water in the heavy phase Wt % | Da | Dw | Enrichment factor |
|---|---|---|---|---|---|---|
| 0.08 | <0.05 | 0.61 | 99.3 | 0.12 | <0.0005 | >240 |
| 0.16 | <0.05 | 1.9 | 98 | 0.08 | <0.0005 | >160 |
| 0.50 | <0.05 | 5.1 | 94.3 | 0.10 | <0.0005 | >200 |

For all tested alcohols, high enrichment factors were observed by contacting with gasoline. The alcohol to water ratio ranged from about 100 to >1000 times higher in the light phase compared to the heavy phase. The light/upper phase was the alcohol rich phase in all cases. The experiments showed that high enrichment factors can be reached using gasoline. These high enrichment factors were not limited to high alcohol starting concentrations and high solvent phase to aqueous phase ratios, as high enrichment values could be obtained with low alcohol starting concentrations and low amounts of gasoline.

Furthermore, in case of isobutanol, the concentration of alcohol in the aqueous phase could be reduced to very low amounts even when starting with a saturated isobutanol solution. This allows recycling of an aqueous stream into the front end of a fermentation without limiting the alcohol productivity of the micro-organisms, since presence of high concentrations of alcohol in the fermentation broth can adversely impact the ability of the micro-organisms to produce alcohol.

Example 4

Enrichment of C3-C6 Alcohols from Aqueous Solutions Using Gasoline and Glucose Addition This example illustrates the enrichment of C3-C6 alcohols from aqueous solutions by addition of glucose followed by contacting with gasoline. Aqueous solutions of C3-C6 alcohols, including butanol (BuOH), iso-butanol (i-BuOH) and pentanol (PenOH), were prepared and glucose added to a final concentration of 20% (w/w). These solutions were then mixed with gasoline. The gasoline used was commercial grade with a 95 octane rating. At equilibrium, phase separation was observed forming an upper alcohol rich phase (light phase) and a lower alcohol lean phase (heavy phase). Both phases were analyzed for alcohol and water content. The distribution coefficient of the alcohol was calculated for each experiment by dividing the alcohol concentration in the light phase by the concentration in the heavy phase. The distribution coefficient for water was calculated accordingly. The Enrichment factor was calculated by dividing the distribution coefficient of alcohol by the distribution coefficient of water. All experiments were carried out at 24° C. The results are reported in Table 4.

TABLE 4

The effect of glucose on the enrichment of iso-butanol (i-BuOH) by contact with gasoline at 24° C.

| Alcohol | Light phase composition Alcohol Wt % | Heavy phase composition H$_2$O Wt % | Alcohol Wt % | H$_2$O Wt % | Alcohol Da |
|---|---|---|---|---|---|
| Isobutanol | 1.9 | 0.11 | 1.4 | 78.6 | 1.36 |
| Butanol | 1.9 | 0.11 | 1.5 | 78.5 | 1.27 |
| Pentanol | 3.4 | 0.12 | 0.16 | 79.8 | 21 |

The effect of the glucose addition can be seen when comparing these results to the results of the experiments described in example 3. The concentration of the alcohol in the gasoline phase increased by 1.6 fold for butanol, by 2 fold for isobutanol and by greater than 10 fold for pentanol in the presence of glucose. The enrichment factors increased by about the same factors.

Example 5

Enrichment of C3-C6 Alcohols from Aqueous Solutions Using Gasoline and Calcium Chloride Addition This example illustrates the enrichment of C3-C6 alcohols from dilute aqueous solutions by calcium chloride addition followed by contacting with gasoline. Aqueous solutions of C3-C6 alcohols, including butanol (BuOH), isobutanol (i-BuOH) and pentanol (PenOH), were prepared and calcium chloride was added to a final concentration of 15% (w/w). These solutions were then mixed with gasoline. The gasoline used was commercial grade with a 95 octane rating. At equilibrium, phase separation was observed, forming an upper alcohol rich phase (light phase) and a lower alcohol lean phase (heavy phase). Both phases were analyzed for alcohol and water contents. The distribution coefficient of the alcohol was calculated for each experiment by dividing the alcohol concentration in the light phase by the concentration in the heavy phase. All experiments were carried out at 24° C. The results are summarized in Table 5.

TABLE 5

The effect of calcium chloride on the enrichment of iso-butanol (i-BuOH) by contact with gasoline at 24° C.

| Alcohol | Light phase composition Alcohol Wt % | Heavy phase composition H$_2$O Wt % | Alcohol Wt % | H$_2$O Wt % | Alcohol Da |
|---|---|---|---|---|---|
| Isobutanol | 3.3 | 0.17 | 0.94 | 84.1 | 3.5 |
| Butanol | 2.6 | 0.16 | 0.86 | 84.1 | 3.0 |
| Pentanol | 2.2 | 0.08 | 0.14 | 84.9 | 15 |

The effect of the calcium chloride addition can be seen when comparing these results to the results of the experiments described in example 3. The concentration of the alcohol in the gasoline phase increased by 3 fold for butanol, by 4.5 fold for isobutanol and by greater than 10 fold for pentanol in the presence of calcium chloride. The enrichment factors increased by about the same factors.

Example 6

Enrichment of C3-C6 Alcohols from Saturated Aqueous Solutions Using Gasoline and the Addition of a Hydrophilic Compound This example illustrates the enrichment of C3-C6 alcohols from saturated aqueous solutions by addition of calcium chloride or glucose followed by contacting with gasoline.

Saturated aqueous solutions of C3-C6 alcohols, including butanol (BuOH), isobutanol (i-BuOH) and pentanol (PenOH), were prepared by addition of alcohol to water until phase separation. The heavy phase was isolated and calcium chloride or glucose was added to it to a final concentration of 15% (w/w) and 20% (w/w), respectively. These solutions were then mixed with gasoline. The gasoline used was commercial grade with a 95 octane rating. At equilibrium, phase separation was observed forming an upper, alcohol-rich phase (light phase) and a lower, alcohol-poor phase (heavy phase). Both phases were analyzed for alcohol and water content. The extraction yield was calculated for each experiment by dividing the alcohol amount in the solvent by the initial alcohol amount in the solution. One stage extraction was carried out at 24° C. The results are summarized in Table 6.

TABLE 6

The effect of glucose and calcium chloride on the enrichment of iso-butanol (i BuOH) n-butanol (BuOH) and n-Pentanol (Pentanol) by contact with gasoline at 24° C.

| The C3-C6 alcohol | Additive | Initial alcohol conc. (wt %) in aqueous solution | Solvent/aqueous solution w/w ratio | Final alcohol conc. (wt %) in aqueous solution | Alcohol conc. (wt %) in solvent solution | Extraction yield (%) |
|---|---|---|---|---|---|---|
| i-BuOH | — | 8.0 | 6.4 | 1.6 | 1.0 | 80 |
| i-BuOH | 20% glucose | 8.0 | 3.4 | 1.4 | 1.9 | 80 |
| i-BuOH | 15% CaCl2 | 8.0 | 2.1 | 0.9 | 3.3 | 90 |
| BuOH | — | 8.0 | 4.9 | 1.6 | 1.3 | 80 |
| BuOH | 20% glucose | 8.0 | 3.4 | 1.5 | 1.9 | 80 |
| BuOH | 15% CaCl2 | 8.0 | 2.7 | 0.9 | 2.6 | 90 |
| Pentanol | — | 2.7 | 2.1 | 0.6 | 1.0 | 75 |
| Pentanol | 20% glucose | 2.7 | 0.8 | 0.16 | 3.4 | 90 |
| Pentanol | 15% $CaCl_2$ | 2.7 | 1.2 | 0.14 | 2.2 | 90 |

The results illustrate that higher extraction yield values could be reached if either glucose or calcium chloride were present in the solution. Thus, a larger fraction of the alcohol can be extracted by a smaller amount of gasoline. At the same time lower concentrations of the alcohol were reached in the remaining aqueous solution.

Example 7

Phase Separation of Propanol from Aqueous Solutions by Addition of a Hydrophilic Compound This example illustrates the induction of phase separation of propanol in water solutions by addition of a hydrophilic compound. Aqueous solutions of propanol were prepared and hydrophilic compounds, including calcium chloride, sucrose or glucose, were added to various final concentrations. The number of liquid phases present in each mixture at 25° C. was noted. The results are summarized in Table 7.

TABLE 7

Enrichment by adding hydrophilic solute to propanol solutions

| Hydrophilic solute | Solute concentration | Number of phases |
|---|---|---|
| None | | 1 |
| $CaCl_2$ | 9.5% | 1 |

TABLE 7-continued

Enrichment by adding hydrophilic solute to propanol solutions

| Hydrophilic solute | Solute concentration | Number of phases |
|---|---|---|
| $CaCl_2$ | 15.1% | 2 |
| Glucose | 40% | 1 |
| Glucose | 60% | 2 |
| Sucrose | 40% | 2 |

Propanol is fully miscible with water, as it forms a single liquid phase when mixed with water at any proportion. This is also true if low concentrations of hydrophilic compounds are added to the aqueous propanol solution. However, addition of a high enough concentration, which is dependent on the particular hydrophilic compound used, resulted in the formation of a two phase systems where propanol was highly enriched in the light phase compared to the heavy phase.

Example 8

Phase Separation of Tertiary-Butanol (or t-Butanol) from Aqueous Solutions by Addition of Glucose This example illustrates the induction of phase separation of t-butanol (t-BuOH) in water solution by addition of glucose. An aqueous solution of t-butanol (50% v/v) was prepared at 25° C. and glucose was added to a final concentration of 20% (w/v). Two liquid phases formed, where 42% of the volume was heavy phase and 58% light phase. Both phases were analyzed for t-butanol concentration. The t-BuOH and glucose concentrations in the heavy phase were about 150 g/L and about 45% w/w, respectively. The light phase had about 520 g/L of t-BuOH.

t-BuOH is fully miscible with water, as it forms a single phase when mixed with water at any proportion. However, addition of glucose resulted in the formation of two phases. t-BuOH was enriched in the light phase as compared to the heavy phase by a factor of about 3.5.

Example 9

Phase Separation and Concentration of Sub-Saturated Butanol and Isobutanol Solutions by Addition of Glucose This example illustrates the induction of phase separation of butanol or isobutanol in water solutions by addition of glucose. Aqueous solutions of 7% butanol (BuOH) or isobutanol (i-BuOH) were prepared and glucose was added to a final concentration of 20% (w/w). Two liquid phases formed for both alcohols. The light and heavy phases were analyzed for alcohol content for each experiment. The results are reported in Table 9. All experiments were carried out at 25° C. The distribution coefficient was calculated by division of the concentration of butanol in the light phase by the concentration of butanol in the heavy phase.

TABLE 9

Enrichment by adding glucose to aqueous solutions of butanol and iso-butanol

| Alcohol | Alcohol in light phase (% w/w) | Alcohol in heavy phase (% w/w) | Distribution coefficient |
| --- | --- | --- | --- |
| BuOH | 85 | 4.3 | 20 |
| i-BuOH | 87 | 5.1 | 17 |

The results of this experiment show that addition of glucose to sub-saturated solutions of butanol and isobutanol forces phase separation. Two liquid phases were formed where the light/upper phase is alcohol rich and the heavy/lower phase is alcohol lean (water rich). Butanol was more concentrated in the light phase by 20 fold compared to the heavy phase and by approximately 12 fold compared to the starting solution. Isobutanol was more concentrated in the light phase by 17 fold compared to the heavy phase and by approximately 12 fold compared to the starting solution.

Example 10

Phase Separation and Concentration of Sub-Saturated Isobutanol Solutions by Addition of Glucose This example illustrates the induction of phase separation for isobutanol in water solutions by glucose addition. Sub-saturated aqueous solutions of isobutanol were prepared and glucose was added to a final concentration of 5% to 20% (w/w). Two liquid phases formed for all concentrations. Each light and heavy phase was analyzed for isobutanol content. The results are reported in Table 10. All experiments were carried out at 25° C. The distribution coefficient was calculated by division of the concentration of isobutanol in the light phase by the concentration of isobutanol in the heavy phase.

TABLE 10

| Light phase composition | | Heavy phase composition | | |
| --- | --- | --- | --- | --- |
| H$_2$O Wt % | i-BuOH Wt % | Glucose Wt % | i-BuOH Wt % | Distribution coefficient |
| 16.1 | 83.9 | 5.0 | 8.3 | 10 |
| 15.1 | 84.9 | 10.6 | 6.8 | 12.5 |
| 13.7 | 86.2 | 20.4 | 5.7 | 15 |

The results of this experiment show that the addition of glucose to sub-saturated solutions of isobutanol forces phase separation. Two liquid phases were formed where the light/upper phase is alcohol rich and the heavy/lower phase is alcohol lean (water rich). The distribution coefficient increased with higher concentrations of glucose.

Example 11

Phase Separation of Sub-Saturated Aqueous Butanol and Isobutanol Solutions by Addition of Calcium Chloride This example illustrates the induction of phase separation of butanol or isobutanol in water solutions by calcium chloride addition. Aqueous solutions of 4% butanol (BuOH) or isobutanol (i-BuOH) were prepared and calcium chloride was added to a final concentration of 15% (w/w). Two liquid phases formed for both alcohols. The light and heavy phases were analyzed for alcohol content for each experiment. The results are reported in Table 11. All experiments were carried out at 25° C. The distribution coefficient was calculated by division of the concentration of butanol in the light phase by the concentration of butanol in the heavy phase.

TABLE 11

Enrichment by adding calcium chloride to aqueous solutions of butanol and iso-butanol

| Alcohol | Alcohol in light phase (% w/w) | Alcohol in heavy phase (% w/w) | Distribution coefficient |
| --- | --- | --- | --- |
| BuOH | 90 | 2.3 | 39 |
| i-BuOH | 91 | 2.9 | 31 |

The results of this experiment show that addition of calcium chloride to sub-saturated solutions of butanol and isobutanol forces phase separation. Two liquid phases formed where the light/upper phase was alcohol rich and the heavy/lower phase was alcohol lean. Butanol was more concentrated in the light phase by 39 fold compared to the heavy phase and by approximately 23 fold compared to the starting solution. Isobutanol was more concentrated in the light phase by 31 fold compared to the heavy phase and by approximately 23 fold compared to the starting solution.

Example 12

Enrichment of Butanol by Adsorption

This example illustrates the enrichment of butanol by adsorption.

The experiment was carried out using Amberlite® XAD16, which is a non-ionic, hydrophobic, cross-linked polymeric adsorbent to extract butanol from an aqueous solution. The adsorption capacity of Amberlite® XAD16 is derived from its macromolecular structure, high surface area and the aromatic nature of its surface.

Sub-saturated aqueous solutions of butanol were prepared and contacted with the resin. The experiment was carried out at 25° C. The resin and the aqueous butanol solution were mixed and shaken for 1.5 h. After shaking the resin was separated from the aqueous solution. The composition of the separated aqueous solution, of the resin after enrichment and the distribution coefficient are reported in Table 12.

TABLE 12

Enrichment by contact with Amberlite ® XAD16

| Solution composition BuOH Wt % | Resin composition BuOH/resin Wt % | Distribution coefficient Da |
| --- | --- | --- |
| 2.9 | 30.0 | 10.3 |
| 1.39 | 21.5 | 15.5 |

TABLE 12-continued

Enrichment by contact with Amberlite ® XAD16

| Solution composition BuOH Wt % | Resin composition BuOH/resin Wt % | Distribution coefficient Da |
|---|---|---|
| 0.45 | 10.4 | 23 |
| 0.11 | 4.0 | 35 |

The results of this experiment show high efficiency of the enrichment. Butanol was more concentrated in the resin compared to the concentration in the aqueous solution with distribution coefficients ranging from about 10 to about 35.

Example 13

Enrichment of Isobutanol from Aqueous Solutions with Acidic Amine-Based Extractants This example illustrates the efficiency of isobutanol extraction from sub-saturated aqueous solutions using an acidic, amine-based extractant.

To reach amine concentrations of 1 mol/kg, trioctylamine was mixed with decane. This organic solution had to be subsequently acidified with sulfuric acid. To do so, the amine solution was mixed with sulfuric acid (30% or 75% acid w/w) resulting in the extraction of parts of the acid into the organic phase. The mixture formed two phases which were separated and the acidified organic phase was used as the acidic extractant for the extraction of isobutanol from an aqueous solution. The extraction was carried out by mixing the acidic extractant with the aqueous isobutanol solutions at 25° C. until equilibrium was reached. The phases were then separated and analyzed. In some cases only one extractant phase formed, while in other cases the formation of two extractant phases could be observed. When two extractant phases were formed, these phases were combined and octanol, acting as a co-solvent, was added to force the formation of a single liquid phase. The combined phase was analyzed and the results were corrected for the dilution by the co-solvent. The aqueous phase and the extractant phase were analyzed for sulfuric acid and isobutanol concentration. The results are summarized in Table 13.

TABLE 13

Enrichment by contact with an acidic amine-based extractant

| | Extractant phase | | | Aqueous phase | | |
|---|---|---|---|---|---|---|
| Number of extractant phases | i-BuOH Wt % | $H_2SO_4$ Mol eq./Kg | i-BuOH Wt % | $H_2SO_4$ Mol eq./Kg | $H_2SO_4$ Wt % | i-BuOH Da |
| 2 | 2.6 | 1.77 | 0.26 | 2.5 | 12.1 | 10.1 |
| 2 | 1.28 | 1.77 | 0.11 | 2.6 | 12.7 | 11.6 |
| 2 | 3.4 | 1.05 | 0.90 | 0.45 | 2.20 | 3.7 |
| 1 | 7.9 | 1.05 | 2.2 | 0.25 | 1.24 | 3.6 |
| 1 | 3.5 | 1.06 | 1.29 | 0.22 | 1.09 | 2.7 |
| 2 | 2.1 | 1.03 | 0.48 | 0.20 | 0.97 | 4.4 |
| 2 | 1.18 | 1.05 | 0.13 | 0.19 | 0.94 | 9.3 |

The results show large distribution coefficients for the extraction into the acidic, amine-based extractant. The distribution coefficients were dependent on the sulfuric acid concentration in the acidic extractant.

When the concentration of sulfuric acid in the extractant phase was about one equivalent per mol of amine, the distribution coefficients were similar or slightly higher compared to the distribution coefficients determined for polar solvents, such as tri-butyl-phosphate and decanol (see Example 1). However, when the concentrations of the sulfuric acid was greater than that, very high distribution coefficients (>10) were observed.

Example 14

Enrichment of Isobutanol from Dilute Aqueous Solutions with Low Amounts Acidic Amine-Based Extractants This example illustrates the efficiency of isobutanol enrichment from dilute aqueous isobutanol solutions using low amounts of acidic, amine-based extractant.

To reach amine concentrations of 1 mol/kg, trioctylamine was mixed with decane. This organic solution had to be subsequently acidified with sulfuric acid. To do so, the amine solution was mixed with sulfuric acid (30% or 75% acid w/w) resulting in the extraction of parts of the acid into the organic phase. The mixture formed two phases which were separated and the acidified organic phase was used as the acidic extractant for the enrichment of isobutanol from an aqueous solution. The enrichment was carried out by mixing the acidic extractant with the aqueous isobutanol solutions at 25° C. until equilibrium was reached. The phases were then separated and analyzed. In some cases only one extractant phase formed, while in other cases the formation of two extractant phases could be observed. When two extractant phases were formed, these phases were combined and octanol, acting as a co-solvent, was added to force the formation of a single liquid phase. The combined phase was analyzed and the results were corrected for the dilution by the co-solvent. The aqueous phase and the extractant phase were analyzed for sulfuric acid and isobutanol concentration, the extraction yield was calculated and the results were summarized in Table 14

TABLE 14

Enrichment of i-BuOH from aqueous solutions of various concentrations into acidic, amine-based extractants

| Initial i-BuOH conc. (wt %) in aqueous solution | H2SO4 concentration in the extractant (Wt %) | Solvent/ aqueous solution w/w ratio | Final i-BuOH conc. (%) in aqueous solution | i-BuOH conc. (Wt %) in the extractant | Extraction yield (%) |
|---|---|---|---|---|---|
| 6.1 | 1.05 | 0.5 | 2.2 | 7.9 | 64 |
| 3.0 | 1.05 | 0.5 | 1.29 | 3.5 | 56 |
| 2.6 | 1.05 | 1.0 | 0.48 | 2.1 | 80 |
| 1.3 | 1.05 | 1.0 | 0.13 | 1.18 | 90 |
| 4.3 | 1.05 | 1.0 | 0.90 | 3.4 | 80 |
| 1.6 | 1.8 | 0.5 | 0.26 | 2.6 | 80 |
| 1.4 | 1.8 | 1.0 | 0.11 | 1.3 | 93 |

The results show that high extraction yield values can be reached by a one step extraction at 25° C. even for low solvent to aqueous phase ratios. Furthermore, the same high extraction yield values could be reached for low starting concentrations of isobutanol in water. In addition, the concentration of isobutanol in the aqueous phase could be reduced to very low concentrations for all starting concentrations. This allows recycling of an aqueous stream into the front end of a fermentation without limiting the alcohol productivity of microorganisms.

Example 15

Enrichment by Contact with Molecular Sieves

This example illustrates the enrichment of alcohol/water solutions by adsorption of water to molecular sieves.

Alcohol/water feed solutions of isopropanol, isobutanol and isopentanol were prepared. For isopropanol, a solution containing about 6.5 wt % water was used as a feed stream. For isobutanol and isopentanol, approximately equal volumes of water and alcohol were mixed. The mixture was allowed to separate and the water saturated alcohol phase (light phase) was decanted and used as a feed stream. Columns consisting of oven dried ceramic substrate, 3 Angstrom, 8×12 mesh molecular sieve beds were prepared. The column used in the isopropanol case had a length to diameter ratio of 20. The columns used in the isobutanol and isopentanol cases had a length to diameter ratio of 40. Each feed solution was independently pumped from bottom to top through a separate column at a flow rate of about 10 ml/min Product samples were collected downstream of the columns for each alcohol stream and analyzed for water content using a Karl Fischer Coulometer. As shown in the column ROH/H$_2$O below, the alcohol to water ratio (ROH/H$_2$O) increased in the product stream compared to the feed stream indicating that the product stream was enriched in alcohol. As shown in the column $C_{Product}/C_{Feed}$, the alcohol concentration in the product stream to feed stream ratio ($C_{product}/C_{Feed}$) is greater than 1 indicating that the product stream was enriched in alcohol.

| Alcohol | Enrichment ROH/H$_2$O | $C_{product}/C_{Feed}$ |
|---|---|---|
| Isopropanol Feed | 14 | 1.1 |
| Isopropanol Product | 339 | |
| Isobutanol Feed | 6 | 1.2 |
| Isobutanol Product | 1147 | |
| Isopentanol Feed | 9 | 1.1 |
| Isopentanol Product | 2724 | |

Example 16

Enrichment by Generation of Isobutanol and Water Azeotrope Composition

This example illustrates the enrichment of isobutanol by the generation of the isobutanol water azeotrope composition at a pressure of about 990 mbar.

A 4.7% by weight solution of isobutanol in water solution was added to a 250 mL round bottom flask which was equipped with a short path distillation head fitting, vapor temperature reading, and 25 mL overhead condensate receiver. The 250 mL flask was heated with an electric hot plate. The isobutanol in water solution in the distillation flask was heated until vapor was formed and condensed in the overhead flask. Vapor temperature was recorded and the solution mixture was analyzed for isobutanol content. The vapor temperature of the boiling solution was about 89-92° C. The azeotropic vapor was collected into the overhead flask and condensed. The overhead condensed material formed a light phase of 10.3 mL and a heavy phase of 3.1 mL. The composition of the light phase was 670 g/L isobutanol and the heavy water rich phase was 86 g/L isobutanol. The post distillation sample remaining behind in the round bottom flask contained 17 g/L isobutanol.

The example demonstrates the efficient concentration of isobutanol to 670 g/L starting from a dilute solution comprising 47 g/L isobutanol by generating the minimum boiling point azeotropic vapor and condensing the vapor into an isobutanol rich light phase and water rich heavy phase.

Example 17

Enrichment by Generation of 1-Butanol and Water Azeotrope Composition

This example illustrates the enrichment of 1-butanol by the generation of the 1-butanol water azeotrope composition at a pressure of about 990 mbar.

A 4.6% by weight solution of 1-butanol in water was added to a 250 mL round bottom flask equipped with a short path distillation head fitting, vapor temperature reading, and 25 mL overhead condensate receiver. The 250 mL flask was heated with an electric hot plate. The solution in the distillation flask was heated until vapor was formed. Vapor temperature was recorded and compositional analysis performed on overhead condensate and post distillation sample in the flask. The temperature of condensing vapor ranged from 92-93.5° C. Azeotropic vapor was collected into the overhead flask and condensed. The overhead condensed material formed a light phase of 8.1 mL and a heavy phase of 2.8 mL. The composition of the light phase was 687 g/L 1-butanol and the heavy water rich phase was 80 g/L 1-butanol. The post distillation pot sample was 20 g/L 1-butanol.

The example demonstrates the efficient concentration of 1-butanol starting with a dilute 46 g/L composition by generating the minimum boiling point azeotrope vapor and condensing the vapor into an isobutanol rich light phase and water rich heavy phase.

Example 18

Enrichment by Generation of Iso-Butanol and Water Azeotropecomposition

This example illustrates the enrichment of isobutanol from fermentation broth by the generation of the isobutanol water azeotrope composition at a pressure of about 990 mbar.

A solution from a laboratory batch fermentation containing 2 g/L isobutanol was added to a 250 mL round bottom flask which has a short path distillation head fitting, vapor temperature reading, and 25 mL overhead condensate receiver. The 250 mL flask was heated with an electric hot plate. The solution is the distillation flask was heated until vapor was formed and condensed in the overhead flask. Vapor temperature was recorded and compositional analysis performed on overhead condensate and post distillation pot sample. The temperature of condensing vapor ranged from 89-92° C. Azeotropic vapor was condensed and collected into the overhead flask. The composition of the overhead condensed material was 40 g/L isobutanol. The post distillation pot sample was 1 g/L 1-butanol.

Example 19

Enrichment by Generation of Iso-Butanol and Water Azeotrope Composition

This example demonstrates the enrichment of isobutanol by the generation of isobutanol water azeotrope composition at a pressure of about 155 mbar.

A 400 mL solution from a laboratory batch fermentation containing 6 g/L isobutanol was added to a 1000 mL rotary vacuum evaporation apparatus. The rotary vacuum evaporation flask was heated with a hot water bath. The vaporized material was condensed with chilled water against a glass laboratory condenser connected to a vacuum source. A vapor thermocouple in the vapor stream recorded the vapor temperature. Condensed material was collected in a 100 mL vacuum collection flask. In the experiment, vacuum was pulled on the system until vapor was formed. Vapor temperature was recorded and compositional analysis performed on overhead condensate and post distillation pot sample.

The temperature of condensing vapor ranged from 27-30° C. at 155 mbar absolute. Azeotropic vapor was condensed and collected into the overhead flask. The overhead condensed material formed a light phase of 0.26 mL and a heavy phase of 0.21 mL. The composition of the light phase was 623 g/L isobutanol and the heavy water rich phase was 115 g/L 1-butanol. The post distillation pot sample was 3 g/L isobutanol. The example demonstrates the efficient concentration of starting with a dilute starting composition and generating the minimum boiling point azeotrope to vapor. Phase separation volume split was not measurable due to small total sample volume.

General methods used in Examples 20-25 and 32-33 are described below.

Sample preparation: All Samples (2 mL) from fermentation experiments performed in shake flasks were stored at −20° C. for later substrate and product analysis. Prior to analysis, samples were thawed, mixed well, and then centrifuged at 14,000×g for 10 min. The supernatant was filtered through a 0.2 µm filter. Analysis by HPLC or GC of substrates and products was performed using authentic standards (>99%, obtained from Sigma-Aldrich), and a five-point calibration curve (with 1-pentanol as an internal standard for analysis by gas chromatography).

Determination of optical density and cell dry weight: The optical density of cultures was determined at 600 nm using a DU 800 spectrophotometer (Beckman-Coulter, Fullerton, Calif., USA). Samples were diluted as necessary to yield an optical density of between 0.1 and 0.8. The cell dry weight was determined by centrifuging 50 mL of culture prior to decanting the supernatant. The cell pellet was washed once with 50 mL of milliQ $H_2O$, centrifuged and the pellet was washed again with 25 mL of milliQ $H_2O$. The cell pellet was then dried at 80° C. for at least 72 hours. The cell dry weight was calculated by subtracting the weight of the centrifuge tube from the weight of the centrifuge tube containing the dried cell pellet. For *E. coli* cultures, an OD600 to cell dry weight conversion factor of 0.25 was used.

Gas Chromatography: Analysis of volatile organic compounds, including ethanol and isobutanol, was performed on a HP 5890 gas chromatograph fitted with an HP 7673 Autosampler, a DB-FFAP column (J&W; 30 m length, 0.32 mm ID, 0.25 µm film thickness) or equivalent connected to a flame ionization detector (FID). The temperature program was as follows: 200° C. for the injector, 300° C. for the detector, 100° C. oven for 1 minute, 70° C./minute gradient to 235° C., and then hold for 2.5 min Analysis was performed using authentic standards (>99%, obtained from Sigma-Aldrich), and a 5-point calibration curve with 1-pentanol as the internal standard.

High Performance Liquid Chromatography: Analysis of glucose and organic acids was performed on a HP-1100 High Performance Liquid Chromatography system equipped with a Aminex HPX-87H Ion Exclusion column (Bio-Rad, 300× 7.8 mm) or equivalent and an $H^+$ cation guard column (Bio-Rad) or equivalent. Organic acids were detected using an HP-1100 UV detector (210 nm, 8 nm, 360 nm reference) while glucose was detected using an HP-1100 refractive index detector. The column temperature was 60° C. This method was isocratic with 0.008 N sulfuric acid in water as mobile phase. Flow was set at 0.6 mL/min. Injection size was 20 µL and the run time was 30 minutes.

Molecular biology and bacterial cell culture: Standard molecular biology methods for cloning and plasmid construction were generally used, unless otherwise noted (Sambrook, J., Russel, D. W. *Molecular Cloning, A Laboratory Manual*. 3 ed. 2001, Cold Spring Harbor, N.Y.: Cold Spring Harbor Laboratory Press). Standard recombinant DNA and molecular biology techniques used in the Examples are well known in the art and are described by Sambrook, J., Russel, D. W. *Molecular Cloning, A Laboratory Manual*. 3 ed. 2001, Cold Spring Harbor, New York: Cold Spring Harbor Laboratory Press; and by T. J. Silhavy, M. L. Bennan, and L. W. Enquist, *Experiments with Gene Fusions*, Cold Spring Harbor Laboratory Press, Cold Spring Harbor, N.Y. (1984) and by Ausubel, F. M. et al., *Current Protocols in Molecular Biology*, pub. by Greene Publishing Assoc. and Wiley-Interscience (1987).

General materials and methods suitable for the routine maintenance and growth of bacterial cultures are well known in the art. Techniques suitable for use in the following examples may be found as set out in *Manual of Methods for General Bacteriology* (Phillipp Gerhardt, R. G. E. Murray, Ralph N. Costilow, Eugene W. Nester, Willis A. Wood, Noel R. Krieg and G. Briggs Phillips, eds.), American Society for Microbiology, Washington, D.C. (1994)) or by Thomas D. Brock in *Biotechnology: A Textbook of Industrial Microbiology*, Second Edition, Sinauer Associates, Inc., Sunderland, Mass. (1989).

Preparation of Electrocompetent Cells and Transformation: the Acceptor Strain Culture was grown in SOB-medium (Sambrook, J., Russel, D. W. *Molecular Cloning, A Laboratory Manual*. 3 ed. 2001, Cold Spring Harbor, N.Y.: Cold Spring Harbor Laboratory Press) to an OD600 of about 0.6 to 0.8. The culture was concentrated 100-fold, washed once with ice cold water and 3 times with ice cold 10% glycerol. The cells were then resuspended in 150 µL of ice-cold 10% glycerol and aliquoted into 50 µL portions. These aliquots were used immediately for standard transformation or stored at −80° C. These cells were transformed with the desired plasmid(s) via electroporation. After electroporation, SOC medium (Sambrook, J., Russel, D. W. *Molecular Cloning, A Laboratory Manual*. 3 ed. 2001, Cold Spring Harbor, N.Y.: Cold Spring Harbor Laboratory Press) was immediately added to the cells. After incubation for an hour at 37° C. the cells were plated onto LB-plates containing the appropriate antibiotics and incubated overnight at 37° C.

Example 20

Production and Recovery of Isobutanol Using an Integrated Fermentation and Recovery System This example illustrates the production and recovery of isobutanol using an integrated fermentation and recovery system.

GEVO1780 is a modified bacterial biocatalyst that contains genes on two plasmids which encode a pathway of enzymes that convert pyruvate into isobutanol. When the biocatalyst GEVO1780 was contacted with glucose in a medium suitable for growth of the biocatalyst, at about 30° C., the biocatalyst produced isobutanol from the glucose. An overnight starter culture was started in a 250 mL Erlenmeyer flask with GEVO1780 cells from a freezer stock with a 40 mL volume of modified M9 medium consisting of 85 g/L glucose, 20 g/L yeast extract, 20 µM ferric citrate, 5.72 mg/L $H_3BO_3$, 3.62 mg/L $MnCl_2.4H_2O$, 0.444 mg/L $ZnSO_4.7H_2O$, 0.78 mg/L $Na_2MnO_4.2H_2O$, 0.158 mg/L $CuSO_4.5H_2O$, 0.0988 mg/L $CoCl_2.6H_2O$, 6.0 g/L $NaHPO_4$, 3.0 g/L $KH_2PO_4$, 0.5 g/L NaCl, 2.0 g/L $NH_4Cl$, 0.0444 g/L $MgSO_4$, and 0.00481 g/L $CaCl_2$ and at a culture $OD_{600}$ of about 0.05. The starter culture was grown for approximately 14 hrs in a 30° C. shaker at 250 rpm. Some of the starter culture was then transferred to a 2000 mL DasGip fermentor vessel containing about 1500 mL of modified M9 medium to achieve an initial culture $OD_{600}$ of about 0.1. The fermentor vessel was attached to a computer control system to monitor and control pH at 6.5 through addition of base, temperature at about 30° C., dissolved oxygen, and agitation. The vessel was agitated, with a minimum agitation of 400 rpm and agitation was varied to maintain a dissolved oxygen content of about 50% using a 25 sL/h air sparge until the $OD_{600}$ was about 1.0. The vessel was then induced with 0.1 mM IPTG. After continuing growth for approximately 8-10 hrs, the dissolved oxygen content was decreased to 5% with 400 rpm minimum agitation and 10 sl/h airflow. Continuous measurement of the fermentor vessel off-gas by GC-MS analysis was performed for oxygen, isobutanol, ethanol, and carbon dioxide throughout the experiment. Samples were aseptically removed from the fermentor vessel throughout the experiment and used to measure $OD_{600}$, glucose concentration and isobutanol concentration in the broth. Throughout the experiment, supplements of pre-grown and pre-induced biocatalyst cells were added as a concentrate three times since the start of the experiment: at 21 h, 38 h, and 46.3 h. These cells were the same strain and plasmids shown above and used in the fermentor. Supplemented cells were grown as 1 L cultures in 2.8 L Fernbach flasks and incubated at 30° C., 250 RPM in Modified M9 Medium with 85 g/L of glucose. Cultures were induced upon inoculation with 0.1 mM IPTG. When the cells had reached an $OD_{600}$ of about 4.0-5.0, the culture was concentrated by centrifugation and then added to the fermentor. A sterile glucose feed of 500 g/L glucose in DI water was used intermittently during the production phase of the experiment at time points great than 12 h to maintain glucose concentration in the fermentor of about 30 g/L or above.

The fermentor vessel was attached by tubing to a smaller 400 mL fermentor vessel that served as a flash tank and operated in a recirculation loop with the fermentor. The biocatalyst cells within the fermentor vessel were isolated from the flash tank by means of a cross-flow filter placed in-line with the fermentor/flash tank recirculation loop. The filter only allowed cell-free fermentation broth to flow from the fermentor vessel into the flash tank. The volume in the flash tank was approximately 100 mL and the hydraulic retention time was about 10 minutes. Heat and vacuum were applied to the flash tank. The vacuum level applied to the flash tank was initially set at 45 mBar and the flash tank was set at about 45° C. These parameters were adjusted to maintain approximately 6-10 g/L isobutanol in the fermentor throughout the experiment. Generally, the vacuum ranged from 45-100 mBar and the flash tank temperature ranged from 43° C. to 45° C. throughout the experiment. Vapor from the heated flash tank was condensed into a collection vessel as distillate. Cell-free fermentation broth was continuously returned from the flash tank to the fermentation vessel.

The distillate recovered in the experiment was strongly enriched for isobutanol. Isobutanol formed an azeotrope with water and usually lead to a two phase distillate: an isobutanol rich top phase and an isobutanol lean bottom phase. Distillate samples were analyzed by GC for isobutanol concentration. Isobutanol production reached a maximum at around 95 hrs with a batch concentration of about 63 g/L. The isobutanol production rate was about 0.64 g/L/h and the percent theoretical yield was approximately 86%.

Example 21

Production and Recovery of Isobutanol Using an Integrated Fermentation and Recovery System This example illustrates the production and recovery of isobutanol using an integrated fermentation and recovery system.

GEV01780 is a modified bacterial biocatalyst that contains genes on two plasmids which encode a pathway of enzymes that convert pyruvate into isobutanol. When the biocatalyst GEV01780 was contacted with glucose in a medium suitable for growth of the biocatalyst, at about 30° C., the biocatalyst produced isobutanol from the glucose. An overnight starter culture was started in a 250 mL Erlenmeyer flask with GEV01780 cells from a freezer stock with a 40 mL volume of modified M9 medium consisting of 85 g/L glucose, 20 g/L yeast extract, 20 µM ferric citrate, 5.72 mg/L $H_3BO_3$, 3.62 mg/L $MnCl_2.4H_2O$, 0.444 mg/L $ZnSO_4.7H_2O$, 0.78 mg/L $Na_2MnO_4.2H_2O$, 0.158 mg/L $CuSO_4.5H_2O$, 0.0988 mg/L $CoCl_2.6H_2O$, 6.0 g/L $NaHPO_4$, 3.0 g/L $KH_2PO_4$, 0.5 g/L NaCl, 2.0 g/L $NH_4Cl$, 0.0444 g/L $MgSO4$, and 0.00481 g/L $CaCl_2$ and at a culture $OD_{600}$ of 0.02 to 0.05. The starter culture was grown for approximately 14 hrs in a 30° C. shaker at 250 rpm. Some of the starter culture was then transferred to a 2000 mL DasGip fermentor vessel containing about 1500 mL of modified M9 medium to achieve an initial culture $OD_{600}$ of about 0.1. The vessel was attached to a computer control system to monitor and control pH at 6.5 through addition of base, temperature at about 30° C., dissolved oxygen, and agitation. The vessel was agitated, with a minimum agitation of 400 rpm and agitation was varied to maintain a dissolved oxygen content of about 50% using a 25 sL/h air sparge until the $OD_{600}$ was about 1.0. The vessel was then induced with 0.1 mM IPTG. After continuing growth for approximately 8-10 hrs, the dissolved oxygen content was decreased to 5% with 400 rpm minimum agitation and 10 sl/h airflow. Continuous measurement of the fermentor vessel off-gas by GC-MS analysis was performed for oxygen, isobutanol, ethanol, and carbon dioxide throughout the experiment. Samples were aseptically removed from the fermentor vessel throughout the experiment and used to measure $OD_{600}$, glucose concentration, and isobutanol concentration in the broth. Throughout the experiment, supplements of pre-grown and pre-induced biocatalyst cells were added as a concentrate two times after the start of the experiment: at 40 h and 75 h. These cells were the same strain and plasmids shown above and used in the fermentor. Supplemented cells were grown as 1 L cultures in 2.8 L Fernbach flasks and incubated at 30° C., 250 RPM in Modified M9 Medium with 85 g/L glucose. Cultures were induced upon inoculation with 0.1 mM IPTG. When the cells had reached an $OD_{600}$ of about 4.0-5.0, the culture was concentrated by centrifugation and then added to the fermentor. A glucose feed of about 500 g/L glucose in DI water was used intermittently during the production phase of the experiment at time points greater than 12 h to maintain glucose concentration in the fermentor of about 30 g/L or above.

The fermentor vessel was attached by tubing to a smaller 400 mL fermentor vessel that served as a flash tank and operated in a recirculation loop with the fermentor. The biocatalyst cells within the fermentor vessel were isolated from the flash tank by means of a cross-flow filter placed in-line with the fermentor/flash tank recirculation loop. The filter only allowed cell-free fermentation broth to flow from the fermentor vessel into the flash tank. The volume in the flash tank was approximately 100 mL and the hydraulic retention time was about 10 minutes. Heat and vacuum were applied to the flash tank. The vacuum level applied to the flash tank was initially set at about 50 mBar and the flash tank was set at about 45° C. These parameters were adjusted to maintain approximately 6-13 g/L isobutanol in the fermentor throughout the experiment. Generally, the vacuum ranged from 45-100 mBar and the flash tank temperature ranged from 43° C. to 45° C. throughout the experiment. Vapor from the heated flash tank was condensed into a collection vessel as distillate. Cell-free fermentation broth was continuously returned from the flash tank to the fermentation vessel.

The distillate recovered in the experiment was strongly enriched for isobutanol. Isobutanol formed an azeotrope with water and usually lead to a two phase distillate: an isobutanol rich top phase and an isobutanol lean bottom phase. Distillate samples were analyzed by GC for isobutanol concentration. Isobutanol production reached a maximum at around 118 hrs with a batch concentration of about 87 g/L. The isobutanol production rate was about 0.74 g/L/h on average over the course of the experiment. The percent theoretical yield of isobutanol was approximately 90.4% at the end of the experiment.

Example 22

Integrated Fermentation and Recovery System for Isobutanol

This example illustrates an embodiment of an integrated fermentation and recovery system for a C3-C6 alcohol.

GEV01780 is a modified bacterial biocatalyst that contains genes on two plasmids which encode a pathway of enzymes that convert pyruvate into isobutanol. When the biocatalyst GEV01780 was contacted with glucose in a medium suitable for growth of the biocatalyst, at about 30° C., the biocatalyst produced isobutanol from the glucose. An overnight starter culture was started in a 250 mL Erlenmeyer flask with GEV01780 cells from a freezer stock with a 40 mL volume of modified M9 medium consisting of 85 g/L glucose, 20 g/L yeast extract, 20 μM ferric citrate, 5.72 mg/L $H_3BO_3$, 3.62 mg/L $MnCl_2.4H_2O$, 0.444 mg/L $ZnSO_4.7H_2O$, 0.78 mg/L $Na_2MnO_4.2H_2O$, 0.158 mg/L $CuSO_4.5H_2O$, 0.0988 mg/L $CoCl_2.6H_2O$, 6.0 g/L $NaHPO_4$, 3.0 g/L $KH_2PO_4$, 0.5 g/L NaCl, 2.0 g/L $NH_4Cl$, 0.0444 g/L $MgSO4$, and 0.00481 g/L $CaCl_2$ and at a culture $OD_{600}$ of about 0.05. The starter culture was grown for approximately 14 hrs in a 30° C. shaker at 250 rpm. Some of the starter culture was then transferred to a 2000 mL DasGip fermentor vessel containing about 1500 mL of modified M9 medium to achieve an initial culture $OD_{600}$ of about 0.1. The vessel was attached to a computer control system to monitor and control pH at 6.5 through addition of base, temperature at about 30° C., dissolved oxygen, and agitation. The vessel was agitated, with a minimum agitation of 400 rpm and agitation was varied to maintain a dissolved oxygen content of about 50% using a 25 sL/h air sparge until the $OD_{600}$ was about 1.0. The vessel was then induced with 0.1 mM IPTG. After continuing growth for approximately 8-10 hrs, the dissolved oxygen content was decreased to 5% with 400 rpm minimum agitation and 10 sl/h airflow. Continuous measurement of the fermentor vessel off-gas by GC-MS analysis was performed for oxygen, isobutanol, ethanol, and carbon dioxide throughout the experiment. Samples were aseptically removed from the fermentor vessel throughout the experiment and used to measure $OD_{600}$, glucose concentration, and isobutanol concentration in the broth. Throughout the experiment, supplements of pre-grown and pre-induced biocatalyst cells were added as a concentrate after the start of the experiment: at 62.5 h, 87 h, 113 h, and 142 h. These cells were the same strain and plasmids shown above and used in the fermentor. Supplemented cells were grown as 1 L cultures in 2.8 L Fernbach flasks and incubated at 30° C., 250 RPM in Modified M9 Medium. Cultures were induced upon inoculation with 0.1 mM IPTG. When the cells had reached an $OD_{600}$ of about 4.0-5.0, the culture was concentrated by centrifugation and then added to the fermentor. A glucose feed of about 500 g/L glucose in DI water was used intermittently during the production phase of the experiment at time points greater than 12 h to maintain glucose concentration in the fermentor of about 30 g/L or above.

The fermentor vessel was attached by tubing to a smaller 400 mL fermentor vessel that served as a flash tank and operated in a recirculation loop with the fermentor. The volume in the flash tank was approximately 100 mL and the hydraulic retention time was about 5-10 minutes. Heat and vacuum were applied to the flash tank. The vacuum level applied to the flash tank was initially set at about 40 mBar and the flash tank was set at about 36° C. These parameters were adjusted to maintain approximately 5-10 g/L isobutanol in the fermentor throughout the experiment. Generally, the vacuum ranged from about 20-50 mBar and the flash tank temperature of about 36° C. throughout the experiment. Vapor from the heated flash tank was condensed into a collection vessel as distillate. The fermentation broth was continuously returned from the flash tank to the fermentation vessel.

The distillate recovered in the experiment was strongly enriched for isobutanol. Isobutanol formed an azeotrope with water and led to a two phase distillate: an isobutanol rich top phase and an isobutanol lean bottom phase. Distillate samples were analyzed by GC for isobutanol concentration. Isobutanol production reached a maximum at around 166 hrs with a batch concentration of about 106 g/L. The isobutanol production rate was about 0.64 g/L/h and the percent theoretical yield was approximately 91% at the end of the experiment.

Example 23

Production and Recovery of Isobutanol Using an Integrated Fermentation and Recovery System This example illustrates the production and recovery of isobutanol using an integrated fermentation and recovery system.

GEV01780 is a modified bacterial biocatalyst that contains genes on two plasmids which encode a pathway of enzymes that convert pyruvate into isobutanol. When the biocatalyst GEV01780 was contacted with glucose in a medium suitable for growth of the biocatalyst, at about 30° C., the biocatalyst produced isobutanol from the glucose. Overnight starter cultures were started in four 2.8 L Fernbach flasks with GEV01780 cells from freezer stocks with four 1000 mL volumes of modified M9 medium consisting of 85 g/L glucose, 20 g/L yeast extract, 20 μM ferric citrate, 5.72 mg/L $H_3BO_3$, 3.62 mg/L $MnCl_2.4H_2O$, 0.444 mg/L $ZnSO_4.7H_2O$, 0.78 mg/L $Na_2MnO_4.2H_2O$, 0.158 mg/L $CuSO_4.5H_2O$, 0.0988 mg/L $CoCl_2.6H_2O$, 6.0 g/L $NaHPO_4$, 3.0 g/L $KH_2PO_4$, 0.5 g/L NaCl, 2.0 g/L $NH_4Cl$, 0.0444 g/L $MgSO4$, and 0.00481 g/L $CaCl_2$ and at a culture $OD_{600}$ of about 0.05. The cultures were induced with 1 mM IPTG at the point of inoculation and grown for approximately 14 hrs in a 30° C. shaker at 250 rpm. At about 14 hours, the contents of the flasks were then poured into 500 mL sterile graduated plastic bottles and centrifuged for 20 minutes at 4500 rpm. The cells were resuspended in about 100 mL total volume of modified M9 medium without glucose, then transferred to a 2000 mL DasGip fermentor vessel containing about 1500 mL of modified M9 medium, wherein the glucose was replaced by clarified corn liquefact to give an approximate glucose concentration of about 100 g/L and to achieve an initial culture $OD_{600}$ of about 10. Clarified corn liquefact was prepared by incubating a slurry of ground corn at about 60° C. for about 24 hrs to which alpha-amyalse and gluco-amalyase enzymes had been added in sufficient amounts to liberate free glucose from the corn starch. After about 24 hours of treatment as described above, the corn liquefact was clarified by centrifugation and filtration to remove most of the solids and generate a clarified corn liquefact solution of about 250 g/L glucose. The fermentor vessel was attached to a computer control system to monitor and control pH at 6.5 through addition of base, temperature at about 30° C., dissolved oxygen, and agitation. The vessel was agitated, with a minimum agitation of 400 rpm and agitation was varied to maintain a dissolved oxygen content of about 5% using a 10 sL/h air sparge. Continuous measurement of the fermentor vessel off-gas by GC-MS analysis was performed for oxygen, isobutanol, ethanol, and carbon dioxide throughout the experiment. Samples were aseptically removed from the fermentor vessel throughout the experiment and used to measure $OD_{600}$, glucose concentration, and isobutanol concentration in the broth. Supplements of pregrown and pre-induced biocatalyst cells were added as a concentrate throughout this experiment. These cells were the same strain and plasmids shown above and used in the fermentor. Supplemented cells were grown as 1 L cultures in 2.8 L Fernbach flasks and incubated at 30° C., 250 RPM in Modified M9 Medium using glucose as the main carbon source. Cultures were induced upon inoculation with 1 mM IPTG. When the cells had reached an $OD_{600}$ of about 2.0-5.0, the culture was concentrated by centrifugation and then added to the fermentor. A feed of clarified corn liquefact containing about 250 g/L glucose was used intermittently during the experiment to maintain glucose concentration in the fermentor of about 30 g/L or above.

The fermentor vessel was attached by tubing to a smaller 400 mL fermentor vessel that served as a flash tank and operated in a recirculation loop with the fermentor. The volume in the flash tank was approximately 100 mL and the hydraulic retention time was about 5-10 minutes. Heat and vacuum were applied to the flash tank. The vacuum level applied to the flash tank was initially set at about 40 mBar and the flash tank was set at about 36° C. These parameters were adjusted to maintain approximately 5-10 g/L isobutanol in the fermentor throughout the experiment. Generally, the vacuum ranged from about 20-50 mBar and the flash tank temperature of about 36° C. throughout the experiment. Vapor from the heated flash tank was condensed into a collection vessel as distillate. The fermentation broth was continuously returned from the flash tank to the fermentation vessel.

The distillate recovered in the experiment was strongly enriched for isobutanol. Isobutanol formed an azeotrope with water and led to a two phase distillate: an isobutanol rich top phase and an isobutanol lean bottom phase. Distillate samples were analyzed by GC for isobutanol concentration. Isobutanol production reached a maximum at around 217 hrs with a batch concentration of about 124 g/L. The isobutanol production rate was about 0.57 g/L/h on average over the course of the experiment, but a maximum isobutanol production rate of about 1.3 g/L/h was achieved in the experiment. The percent theoretical yield was approximately 74% at the end of the experiment, but a maximum theoretical yield of about 88% theoretical yield was achieved during the experiment.

Example 24

Production and Recovery of Isobutanol Using an Integrated Fermentation and Recovery System This example illustrates the production and recovery of isobutanol using an integrated fermentation and recovery system.

GEV01780 is a modified bacterial biocatalyst that contains genes on two plasmids which encode a pathway of enzymes that convert pyruvate into isobutanol. When the biocatalyst GEV01780 was contacted with glucose in a medium suitable for growth of the biocatalyst, at about 30° C., the biocatalyst produced isobutanol from the glucose. An overnight starter culture was started in a 2.8 L Fernbach flask with GEV01780 cells from a freezer stock with a 1000 mL volume of modified M9 medium consisting of 85 g/L glucose, 20 g/L yeast extract, 20 μM ferric citrate, 5.72 mg/L $H_3BO_3$, 3.62 mg/L $MnCl_2.4H_2O$, 0.444 mg/L $ZnSO_4.7H_2O$, 0.78 mg/L $Na_2MnO_4.2H_2O$, 0.158 mg/L $CuSO_4.5H_2O$, 0.0988 mg/L $CoCl_2.6H_2O$, 6.0 g/L $NaHPO_4$, 3.0 g/L $KH_2PO_4$, 0.5 g/L NaCl, 2.0 g/L $NH_4Cl$, 0.0444 g/L $MgSO4$, and 0.00481 g/L $CaCl_2$ and at a culture $OD_{600}$ of about 0.05. The culture was induced with 1 mM IPTG at the point of inoculation and grown for approximately 14 hrs in a 30° C. shaker at 250 rpm. At about 14 hours, the contents of the flask was then poured into 500 ml sterile graduated plastic bottles and centrifuged for 20 minutes at 4500 rpm. The cells were resuspended in about 40 ml total volume of modified M9 medium, then transferred to a 2000 mL DasGip fermentor vessel containing about 1500 mL of modified M9 medium, wherein the glucose was replaced by corn liquefact with about 17% dry solids concentration and to achieve an initial calculated culture $OD_{600}$ of about 3. Corn liquefact, which was treated with alpha-amyalse, was prepared by diluting sterilized corn liquefact with a dry solids concentration of about 35% with sterile dionized water to a final dry solids concentration of about 17%. The diluted corn liquefact was then added to the modified M9 medium components described above without additional glucose and placed in the 2000 mL fermentor vessel. At the point of inoculation, a dose of gluco-amylase was added to the fermentor vessel in sufficient quantity to hydrolyse the corn starch oligomers present in the corn liquefact to monomeric glucose. The vessel was attached to a computer control system to monitor and control pH at about 6.5 through addition of base, temperature at about 30° C., dissolved oxygen, and agitation. The vessel was agitated, with a minimum agitation of 400 rpm and agitation was varied to maintain a dissolved oxygen content of about 5% using a 10 sL/h air sparge. Continuous measurement of the fermentor vessel off-gas by GC-MS analysis was performed for oxygen, isobutanol, ethanol, and carbon dioxide throughout the experiment. Samples were aseptically removed from the fermentor vessel throughout the experiment and used to measure glucose concentration and isobutanol concentration in the broth. Supplements of pre-grown and pre-induced biocatalyst cells were added as a concentrate throughout this experiment. These cells were the same strain shown above and used in the fermentor. Supplemented cells were grown as 1 L cultures in 2.8 L Fernbach flasks and incubated at 30° C., 250 RPM in Modified M9 Medium using glucose as the main carbon source. Cultures were induced upon inoculation with 1 mM IPTG. When the cells had reached an $OD_{600}$ of about 2.0-5.0, the culture was concentrated by centrifugation and then added to the fermentor. A feed of corn liquefact was prepared by adding dose of gluco-amylase in sufficient quantity to hydrolyse the corn starch oligomers present in the corn liquefact to monomeric glucose and incubation at about 50°

C. for 24 hrs prior to use. The resulting solution contained about 188 g/L glucose and was used intermittently during the experiment to maintain glucose concentration in the fermentor of about 40 g/L or above.

The fermentor vessel was attached by tubing to a smaller 400 mL fermentor vessel that served as a flash tank and operated in a recirculation loop with the fermentor. The volume in the flash tank was approximately 100 mL and the hydraulic retention time was about 5-10 minutes. Heat and vacuum were applied to the flash tank. The vacuum level applied to the flash tank was initially set at about 40 mBar and the flash tank was set at about 36° C. These parameters were adjusted to maintain approximately 5-10 g/L isobutanol in the fermentor throughout the experiment. Generally, the vacuum ranged from about 20-50 mBar and the flash tank temperature was about 36° C. throughout the experiment. Vapor from the heated flash tank was condensed into a collection vessel as distillate. The fermentation broth was continuously returned from the flash tank to the fermentation vessel.

The distillate recovered in the experiment was strongly enriched for isobutanol. Isobutanol formed an azeotrope with water and led to a two phase distillate: an isobutanol rich top phase and an isobutanol lean bottom phase. Distillate samples were analyzed by GC for isobutanol concentration. Isobutanol production reached a maximum at around 166 hrs with a batch concentration of about 30 g/L. The isobutanol production rate was about 0.31 g/L/h on average over the course of the experiment. The percent theoretical yield was not determined in this experiment.

Example 25

Integrated Fermentation and Recovery System for Isobutanol

This example illustrates an embodiment of an integrated anaerobic batch fermentation and recovery system for a C3-C6 alcohol and shows that an engineered microorganism produces a C3-C6 alcohol at a yield of at greater than about 95% of theoretical.

An overnight culture was started in a 250 mL Erlenmeyer flask with GEV01886 cells from a freezer stock with a 40 mL volume of modified M9 medium consisting of 85 g/L glucose, 20 g/L yeast extract, 20 µM ferric citrate, 5.72 mg/L $H_3BO_3$, 3.62 mg/L $MnCl_2.4H_2O$, 0.444 mg/L $ZnSO_4.7H_2O$, 0.78 mg/L $Na_2MnO_4.2H_2O$, 0.158 mg/L $CuSO_4.5H_2O$, 0.0988 mg/L $CoCl_2.6H_2O$, 6.0 g/L $NaHPO_4$, 3.0 g/L $KH_2PO_4$, 0.5 g/L NaCl, 2.0 g/L $NH_4Cl$, 0.0444 g/L MgSO4, and 0.00481 g/L $CaCl_2$ and at a culture $OD_{600}$ of about 0.05. The starter culture was grown for approximately 14 hrs in a 30° C. shaker at 250 rpm. Some of the starter culture was transferred to a 2000 mL DasGip fermentor vessel containing about 1500 mL of modified M9 medium to achieve an initial culture $OD_{600}$ of about 0.1. The fermentor vessel was attached to a computer control system to monitor and control pH at 6.5 through addition of base, temperature at about 30° C., dissolved oxygen, and agitation. The vessel was agitated, with a minimum agitation of 400 rpm and agitation was varied to maintain a dissolved oxygen content of about 50% using a 25 sL/h air sparge until the $OD_{600}$ is about 1.0. The vessel was then induced with 0.1 mM IPTG. After continuing growth for about 3 hours, the dissolved oxygen content was decreased to 0% with 200 rpm agitation and 2.5 sL/h sparge with nitrogen ($N_2$) gas. Continuous measurement of the fermentor vessel off-gas by GC-MS analysis was performed for, isobutanol, ethanol, and carbon dioxide throughout the experiment. Samples were aseptically removed from the fermentor vessel throughout the experiment and used to measure $OD_{600}$, glucose concentration and isobutanol concentration in the broth. Throughout the experiment, supplements of pre-grown and pre-induced biocatalyst cells were added as a concentrate several times since the start of the experiment. These cells were the same strain and plasmids shown above and used in the fermentor. Supplemented cells were grown as 1 L cultures in 2.8 L Fernbach flasks and incubated at 30° C., 250 RPM in Modified M9 Medium with 85 g/L of glucose. Cultures were induced upon inoculation with 0.1 mM IPTG. When the cells reached an $OD_{600}$ of about 4.0-5.0, the culture was concentrated by centrifugation and then added to the fermentor. A sterile glucose feed of 500 g/L glucose in DI water was used intermittently during the production phase of the experiment at time points greater than 12 h to maintain glucose concentration in the fermentor of about 30 g/L or above.

The fermentor vessel was attached by tubing to a smaller 400 mL fermentor vessel that serves as a flash tank and is operated in a recirculation loop with the fermentor. The volume in the flash tank was approximately 100 mL and the hydraulic retention time is about 10 minutes. Heat and vacuum were applied to the flash tank. The vacuum level applied to the flash tank was initially set at about 45 mBar and the flash tank was set at about 36° C. These parameters were adjusted to maintain approximately 6-10 g/L isobutanol in the fermentor throughout the experiment. Generally, the vacuum ranged from about 30-100 mBar and the flash tank temperature ranged from 34° C. to 36° C. throughout the experiment. Vapor from the heated flash tank was condensed into a collection vessel as distillate. The fermentation broth was continuously returned from the flash tank to the fermentation vessel.

The distillate recovered in the experiment was strongly enriched for isobutanol. Isobutanol formed an azeotrope with water and led to a two phase distillate: an isobutanol rich top phase and an isobutanol lean bottom phase. Distillate samples were analyzed by GC for isobutanol concentration. Isobutanol production reached a maximum with a batch concentration of greater than 50 g/L. The percent theoretical yield was approximately 95%.

Example 26

Enrichment by Vacuum Distillation

This example illustrates the enrichment of unsaturated, aqueous isobutanol solutions by vacuum distillation.

The distillation set-up consisted of a 3 neck reaction vessel, a water cooled condenser and a collection flask. During each distillation, an electric heating mantle was used to heat the reaction vessel; a recirculating bath was used to cool the condenser with 3-5° C. water; and a vacuum pump maintained a vacuum of approximately 50 mBar absolute. Thermometers were in place to measure the temperature of the reaction solution and the water bath. The collection flask and reaction vessel were sampled after a target volume of 1-5 mL was collected. Three distillations were performed with aqueous isobutanol solutions of approximately 5, 15 and 40 g/L.

During distillation of the 5 g/L solution, condensation began at a liquid temperature of 35.2° C. 1.75 ml of single phase material was collected. The 4.1 g/L starting material was concentrated 21-fold in the overhead condensed vapor phase material. During distillation of the 15 g/L solution, condensation began at a liquid temperature of 34.3° C. 2 mL of heavy phase and 0.5 mL of light phase were collected. The 12.3 g/L starting material was concentrated 17-fold in the overhead condensed vapor phase material. During distillation of the 40 g/L solution, condensation began at a liquid temperature of 31.9° C. 2.5 mL of heavy phase and 3.5 mL of light phase were collected. The 43.2 g/L starting material was concentrated 10-fold in the overhead condensed vapor phase material. The isobutanol concentration (g/L) from various solutions during the 3 isobutanol distillations are summarized in the table below.

TABLE 26

| | Isobutanol Distillations | | |
|---|---|---|---|
| | 5 g/L | 15 g/L | 40 g/L |
| Starting Solution | 4.1 | 12.3 | 43.2 |
| Final Pot | 3.5 | 10.7 | 36.8 |
| Collection: Heavy | 86.7 | 86.9 | 91.9 |
| Collection: Light | — | 717.8 | 706.6 |

The increase in isobutanol concentration from the starting solution to the vapor phase is shown in the table below.

| | Isobutanol Distillations | | |
|---|---|---|---|
| | 5 g/L | 15 g/L | 40 g/L |
| Concentration in Vapor Phase | 21x | 17x | 10x |

Example 27

Enrichment by Vacuum Distillation

This example illustrates the enrichment of unsaturated, aqueous isopentanol solutions by vacuum distillation.

The distillation set-up consisted of a 3 neck reaction vessel, water cooled condenser and collection flask. During each distillation, an electric heating mantle was used to heat the reaction vessel, a recirculating bath was used to cool the condenser with 3-5° C. water and a vacuum pump maintained a vacuum of approximately 50 mBar absolute. Thermometers were in place to measure reaction solution temperature and water bath temperature. The collection flask and reaction vessel were sampled after a target volume of at least 1-5 mL was collected. Three distillations were performed with aqueous isopentanol solutions of approximately 5, 15 and 40 g/L.

During distillation of the 5 g/L solution, condensation began at a liquid temperature of 35.2° C. 2.5 mL of single phase material were collected. The 4.2 g/L starting material was concentrated 7-fold in the overhead condensed vapor phase material. During distillation of the 15 g/L solution, condensation began at a liquid temperature of 34.3° C. 3 mL of heavy phase and 1 mL of light phase were collected. The 12.2 g/L starting material was concentrated 17-fold in the overhead condensed vapor phase material. During distillation of the 40 g/L solution, condensation began at a liquid temperature of 33.5° C. 5 mL of heavy phase and 3 mL of light phase were collected. The 31.5 g/L starting material was concentrated 10-fold in the overhead condensed vapor phase material. The isopentanol concentration (g/L) from various solutions during the 3 isopentanol distillations are summarized in the table below.

| | Isopentanol Distillations | | |
|---|---|---|---|
| | 5 g/L | 15 g/L | 40 g/L |
| Starting Solution | 4.2 | 12.2 | 31.5 |
| Final Pot | 3.4 | 10.2 | 23.7 |
| Collection: Heavy | 31.2 | 34.1 | 35.9 |
| Collection: Light | — | 724.7 | 763.7 |

The increase in isopentanol concentration from the starting solution to the vapor phase are shown in the table below.

| | Isopentanol Distillations | | |
|---|---|---|---|
| | 5 g/L | 15 g/L | 40 g/L |
| Concentration in the Vapor Phase | 7x | 17x | 10x |

Example 28

Enrichment by Vacuum Distillation

This example illustrates the enrichment of aqueous isopropanol solutions by vacuum distillation.

The distillation set-up consisted of a 3 neck reaction vessel, water cooled condenser and collection flask. During each distillation, an electric heating mantle was used to heat the reaction vessel, a recirculating bath was used to cool the condenser with 3-5° C. water and a vacuum pump maintained a vacuum of approximately 50 mBar. Thermometers were in place to measure reaction solution temperature and water bath temperature. The collection flask and reaction vessel were sampled after a target volume of at least 1-5 ml was collected. Three distillations were performed with aqueous isopropanol solutions of approximately 5, 15 and 40 g/L.

During distillation of the 5 g/L solution, condensation began at a liquid temperature of 35.0° C. 3.3 mL of single phase material were collected. The 5.0 g/L starting material was concentrated 25-fold in the overhead condensed vapor phase material. During distillation of the g/L solution, condensation began at a liquid temperature of 34.7° C. 5 mL of single phase material were collected. The 14.9 g/L starting material was concentrated 12-fold in the overhead condensed vapor phase material. For the 40 g/L starting solution, condensation began at a liquid temperature of 33.3° C. 8.1 mL of single phase material were collected. The 49.2 g/L starting material was concentrated 7-fold in the overhead condensed vapor phase material. The isopropanol concentration (g/L) from various solutions during the 3 isopropanol distillations are shown in the table below.

| | Isopropanol Distillations | | |
|---|---|---|---|
| | 5 g/L | 15 g/L | 40 g/L |
| Starting Solution | 5.0 | 14.9 | 49.2 |
| Final Pot | 3.8 | 12.3 | 31.9 |
| Collection: Heavy | 126.3 | 184.2 | 347.5 |
| Collection: Light | — | — | — |

The increase in isopropanol concentration from the starting solution to the vapor phase is shown in the table below.

|  | Isopropanol Distillations | | |
| --- | --- | --- | --- |
|  | 5 g/L | 15 g/L | 40 g/L |
| Concentration in the Vapor Phase | 25x | 12x | 7x |

Example 29

Enrichment by Vacuum Distillation

This example illustrates the enrichment of unsaturated, aqueous isobutanol by distillation.

A glass distillation set-up with a packed bead reflux column was used. The distillation was conducted in two parts, the vacuum was removed and pot cooled between parts. During the distillation, a heating mantle was used to heat the reaction pot, an agitator kept the reaction pot well mixed, a recirculating bath was used to cool the condenser, a vacuum pump maintained a vacuum of approximately 75 mBar absolute in the system and an alcohol/dry ice trap was used downstream from the condenser. Thermometers were in place to measure reaction pot temperature, vapor temperature above the reflux column and water bath temperature.

During the distillations, a sample valve allowed collection from above the reflux column or redirection of condensate flow through a splitter onto the reflux column. Material was collected when good reflux was observed and the entire column was active. The starting material was a single phase isobutanol solution collected by vacuum evaporation from a 400 L scale fermentation of GEV01780. Condensation was observed on the bottom of the condenser coils as soon as the vacuum was generated with a distillation pot temperature of 22° C. and a vapor temperature of 16° C. When good reflux was observed at a pot temperature of 31° C. and a vapor temperature of 20° C. the distillate collection was initiated. After collection of 840 mL, the distillation was interrupted and the distillation pot was sampled. The isobutanol in the distillation pot was reduced to a concentration of 17 g/L which is 27.9% of the initial amount.

During the second part of the distillation, condensation was also observed as soon as the vacuum was generated. A maximum reaction pot temperature of 40° C. and vapor temperature of 26° C. was reached. These conditions further decreased the reaction pot isobutanol concentration from 17 g/L to 1.5 g/L. At the end of the distillation, 62.2% of the isobutanol initially in the distillation pot was collected as light phase distillate and 14.3% as heavy phase distillate, 15.4% was collected as light phase in the vacuum ice trap and 2.7% as heavy phase in the vacuum ice trap and 2.2% was left behind in the distillation pot. Overall, the concentration increase from the starting material to the vapor phase was 5.0 fold.

Example 30

Removal of Water from the Alcohol-Rich Phase

This example illustrates the effective removal of water from the alcohol rich phase (light phase) by distillation.

A glass distillation set-up with a packed bead reflux column was used. The distillation was conducted in two parts, the vacuum was removed and pot cooled between parts. During the distillation, a heating mantle was used to heat the reaction pot, a recirculating bath was used to cool the condenser and agitator, a vacuum pump maintained a vacuum of approximately 75 mBar absolute in the system and an alcohol/dry ice trap was used downstream from the condenser. Thermometers were in place to measure reaction pot temperature, vapor temperature above the reflux column and water bath temperature. During the distillations, a sample valve allowed collection from above the reflux column or redirection of condensate flow through a splitter onto the reflux column Material was collected when good reflux was observed and the entire column was active.

The light phase (alcohol-rich phase) from 3 different Gevo fermentations was combined. Good reflux was observed at a reaction pot temperature of 27° C. and a vapor temperature of 18.5° C., collection was initiated at this point. After collection of 580 mL, the distillation was interrupted. The distillation pot liquid was 1.44 wt % water at this point. Distillation was resumed and after reaching a maximum liquid temperature of 48° C. and a vapor temperature of 36.5° C., the distillation was ended. The final reaction pot solution was dried to 0.3671 wt % water. The wt % water in the distillation pot was decreased 40-fold.

Example 31

Impact of Temperature on Light and Heavy Phase Composition

This example illustrates the mutual solubility of isobutanol and water as a function of temperature.

First, 20 g of water were mixed with 20 g isobutanol in closed vials at room temperature. The vials were then mixed at 5, 10, 20, 40, 60 or 80° C. The vials were held at the stated temperature while being mixed until equilibrium was established. Then the samples were separated into light and heavy phases while being held at temperature. The samples from the light and the heavy phases were analyzed by HPLC and by Karl-Fischer titration. The results are presented in Table 31.1 and show that the isobutanol concentrations in each phase are temperature dependent.

Table 31.2 summarizes literature data for normal butanol (n-butanol) solubility in water at various temperatures. As expected the solubility of isobutanol is similar to n-butanol and shows similar dependence on temperature.

TABLE 31.1

Light and Heavy Phase Composition of Isobutanol-Water at Various Temperatures

|  | Light phase | | Heavy phase | |
| --- | --- | --- | --- | --- |
| Temperature °C. | Isobutanol Wt % | $H_2O$ Wt % | Isobutanol Wt % | $H_2O$ Wt % |
| 5 | 83.9 | 16.1 | 11.7 | 88.3 |
| 10 | 84.0 | 16.0 | 10.6 | 89.4 |
| 20 | 83.4 | 16.6 | 11.2 | 88.8 |
| 40 | 81.5 | 18.5 | 9.24 | 90.8 |
| 60 | 79.1 | 20.9 | 7.90 | 92.1 |
| 80 | 76.5 | 23.5 | 6.04 | 94.0 |

TABLE 31.2 n-Butanol Solubility in Water at Various Temperatures

| Temperature °C. | heavy phase Butanol Wt % | Light phase Butanol Wt % |
| --- | --- | --- |
| 5 | 9.55 | 80.38 |
| 10 | 8.91 | 80.33 |
| 15 | 8.21 | 80.14 |

TABLE 31.2-continued n-Butanol Solubility in Water at Various Temperatures

| Temperature °C. | heavy phase Butanol Wt % | Light phase Butanol Wt % |
|---|---|---|
| 20 | 7.81 | 79.93 |
| 25 | 7.35 | 79.73 |
| 30 | 7.08 | 79.38 |
| 35 | 6.83 | 78.94 |
| 40 | 6.6 | 78.59 |
| 50 | 6.46 | 77.58 |
| 60 | 5.62 | 76.38 |
| 70 | 6.73 | 74.79 |
| 80 | 6.89 | 73.53 |

Example 32

High Volumetric Productivity Batch Fermentation

This example illustrates a batch fermentation using a biocatalyst with high volumetric productivity.

Gevo 1780 is a modified bacterial biocatalyst that contains genes on two plasmids which encode a pathway of enzymes that convert pyruvate into isobutanol. When the biocatalyst Gevo 1780 was contacted with glucose in a medium suitable for growth of the biocatalyst, at about 30° C., the biocatalyst produced isobutanol from the glucose. Two 400 mL DasGip fermentor vessels containing 200 mL each of modified M9 medium consisting of 85 g/L glucose, 20 g/L yeast extract, 20 µM ferric citrate, 5.72 mg/L $H_3BO_3$, 3.62 mg/L $MnCl_2.4H_2O$, 0.444 mg/L $ZnSO_4.7H_2O$, 0.78 mg/L $Na_2MnO_4.2H_2O$, 0.158 mg/L $CuSO_4.5H_2O$, 0.0988 mg/L $CoCl_2.6H_2O$, 6.0 g/L $NaHPO_4$, 3.0 g/L $KH_2PO_4$, 0.5 g/L NaCl, 2.0 g/L $NH_4Cl$, 0.0444 g/L $MgSO_4$, and 0.00481 g/L $CaCl_2$ were inoculated with GEV01780 cells from frozen stocks. The fermentor vessels were attached to a computer control system to monitor and control pH at 6.5 through addition of base, temperature at 30° C., dissolved oxygen, and agitation. The vessels were agitated, with a minimum agitation of 300 rpm and agitation was varied to maintain a dissolved oxygen content of about 50% using a 12 sL/h air sparge until the $OD_{600}$ was about 1.0. The vessels were then induced with 0.1 mM IPTG. The vessels were operated under these conditions for about 12 hours. At about 12 hours, the contents of the fermentor vessels were then poured into 500 ml sterile graduated plastic bottles and centrifuged for 20 minutes at 4500 rpm. The cells were resuspended in 50 ml total volume of modified M9 medium. A 400 mL DasGip vessel containing 150 mL of modified M9 medium was inoculated with 50 ml of the cell containing medium and then induced with 0.1 mM IPTG. Constant dissolved oxygen content of 5% was maintained using a 2.5 sL/h air sparge with variable agitation automatically controlled from 300 to 1200 rpm. Continuous measurement of the fermentor vessel off gas by GC-MS analysis was performed for oxygen, isobutanol, ethanol, carbon dioxide, and nitrogen throughout the experiment. Samples were aseptically removed from the fermentor vessel throughout the experiment and used to measure $OD_{600}$, glucose concentration by HPLC, and isobutanol concentration in the broth by GC. Isobutanol production reached a maximum at around 22 hours with a batch concentration of about 22 g/L and with a yield of approximately 80% maximum theoretical. Volumetric productivity of the fermentation, calculated when the isobutanol was between 1 g/L and 15 g/L, was about 2.3 g/L/h.

Example 33

High Volumetric Productivity Batch Fermentation

This example illustrates a batch fermentation using a biocatalyst with high volumetric productivity. The modified biocatalyst Gevo 1530 was transformed with the two plasmids pSA69 and pSA55, which encode a pathway of enzymes that convert pyruvate into isobutanol. When the biocatalyst Gevo 1530 (pSA69, pSA55) was contacted with glucose in a medium suitable for growth of the biocatalyst, at about 30° C., the biocatalyst produced isobutanol from the glucose. Two 400 mL DasGip fermentor vessels containing 200 mL each of EZ Rich medium (Neidhardt, F. C., P. L. Bloch, and D. F. Smith. 1974. Culture medium for enterobacteria. Bacteriol. 119:736-47) containing 72 g/L glucose and 10 g/L yeast extract were inoculated with Gevo 1530 (pSA69, pSA55) cells. The vessels were attached to a computer control system to monitor and control pH at 6.5 through addition of base, temperature at about 30° C., dissolved oxygen, and agitation. The vessels were agitated, with a minimum agitation of 300 rpm and agitation was varied to maintain a dissolved oxygen content of about 50% using a 12 sL/h air sparge until the $OD_{600}$ was about 1.0. The vessels were then induced with 0.1 mM IPTG. The vessels were operated under these conditions for about 11 hours. At about 11 hours, the contents of the fermentor vessels were then poured into 500 mL sterile graduated plastic bottles and centrifuged for 20 minutes at 4500 rpm. The cells were resuspended in 50 ml total volume of modified M9 medium. A 400 mL DasGip vessel containing 150 ml of EZ Rich medium containing 72 g/L glucose and 10 g/L yeast extract was inoculated with 50 mL of the cell containing medium and then induced with 0.1 mM IPTG. Cell concentration was approximately 6 g CDW per L. Constant dissolved oxygen content of 5% was maintained using a 2.5 sL/h air sparge with variable agitation automatically controlled from 300 to 1200 rpm. Measurement of the fermentor vessel off-gas by trapping in an octanol bubble trap and then measurement by GC was performed for isobutanol and ethanol. Continuous measurement of off-gas concentrations of carbon dioxide and oxygen were also measured by a DasGip off-gas analyzer throughout the experiment. Samples were aseptically removed from the fermentor vessel throughout the experiment and used to measure $OD_{600}$, glucose concentration by HPLC, and isobutanol concentration in the broth by GC. Isobutanol production reached a maximum at around 4 hours with a batch concentration of 15 g/L and with a yield of approximately 86% maximum theoretical. Volumetric productivity of the fermentation, calculated from the inception of the fermentation at time 0 h to an elapsed fermentation time of about 4 h, was about 3.5 g/L/h.

Example 34

Enrichment by Contact with a Water Adsorbent

This example illustrates the isobutanol enrichment from aqueous isobutanol solutions using molecular sieves to adsorb water. A sub-saturated solution of isobutanol in water was prepared. Two grams of this solution were thoroughly mixed with 1.5 g of 3 Angstrom molecular sieve particles in a vial. After mixing, the vial was left to settle. Three phases were observed—a solid phase containing the molecular sieve particles and two liquid phases comprising an upper, light, isobutanol-rich phase and a lower, heavy, isobutanol-lean phase.

What is claimed is:

1. A method for producing isobutanol comprising:
    (a) culturing a microorganism capable of producing isobutanol in a fermentor, thereby forming a fermentation broth comprising microorganisms and isobutanol;
    (b) removing a portion of the fermentation broth from the fermentor;
    (c) distilling the portion, thereby forming an isobutanol-depleted liquid phase and an isobutanol-enriched vapor phase comprising water and isobutanol;
    (d) condensing the isobutanol-enriched vapor phase formed in step (c), thereby forming an isobutanol-rich liquid phase and a water-rich liquid phase; and
    (e) separating the isobutanol-rich phase liquid from the water-rich liquid phase using a liquid-liquid separator;
    wherein:
        (1) said steps (b)-(e) are conducted simultaneously with step (a);
        (2) the isobutanol-depleted liquid phase comprises viable microorganisms; and
        (3) the isobutanol-depleted liquid phase is returned to the fermentor.

2. The method of claim 1, wherein the isobutanol-enriched vapor phase has an isobutanol concentration at least about 5-fold greater than the isobutanol concentration of the portion of the fermentation broth.

3. The method of claim 1, wherein the isobutanol-enriched vapor phase has an isobutanol concentration at least about 10-fold greater than the isobutanol concentration of the portion of the fermentation broth.

4. The method of claim 1, wherein the isobutanol-enriched vapor phase has an isobutanol concentration at least about 11-fold greater than the isobutanol concentration of the portion of the fermentation broth.

5. The method of claim 1, wherein the isobutanol-enriched vapor phase has an isobutanol concentration at least about 12-fold greater than the isobutanol concentration of the portion of the fermentation broth.

6. The method of claim 1, wherein the isobutanol-enriched vapor phase has an isobutanol concentration at least about 13-fold greater than the isobutanol concentration of the portion of the fermentation broth.

7. The method of claim 1, wherein the isobutanol-enriched vapor phase has an isobutanol concentration at least about 14-fold greater than the isobutanol concentration of the portion of the fermentation broth.

8. The method of claim 1, wherein the isobutanol-enriched vapor phase has an isobutanol concentration at least about 15-fold greater than the isobutanol concentration of the portion of the fermentation broth.

9. The method of claim 1, wherein the isobutanol-rich liquid phase of step (d) has a ratio of isobutanol to water of greater than about 2.

10. The method of claim 1, wherein the isobutanol-rich liquid phase of step (d) has a ratio of isobutanol to water of greater than about 8.

11. The method of claim 1, wherein the ratio of isobutanol to water in the isobutanol-rich liquid phase is greater than the ratio of isobutanol to water in the fermentation broth by at least about 5-fold.

12. The method of claim 1, wherein the ratio of isobutanol to water in the isobutanol-rich liquid phase is greater than the ratio of isobutanol to water in the fermentation broth by at least about 25-fold.

13. The method of claim 1, further comprising cooling the isobutanol-rich liquid phase, thereby increasing the ratio of isobutanol to water in the isobutanol-rich liquid phase.

14. The method of claim 1, wherein said distilling is carried out at a temperature ranging from about 20° C. to about 95° C.

15. The method of claim 1, wherein said distilling is carried out at a temperature ranging from about 25° C. to about 95° C.

16. The method of claim 1, wherein said distilling is carried out at a temperature ranging from about 35° C. to about 95° C.

17. The method of claim 1, wherein said distilling is carried out at a reduced pressure compared to the pressure of the fermentor.

18. The method of claim 1, wherein:
    the distilling is carried out at a reduced pressure compared to the pressure of the fermentor, and at a temperature ranging from about 35° C. to about 95° C.;
    the isobutanol-enriched vapor phase comprises an azeotrope of isobutanol and water;
    the isobutanol-enriched vapor phase has an isobutanol concentration at least about 5-fold greater than the isobutanol concentration of the portion of the fermentation broth; and
    the isobutanol-rich liquid phase has a ratio of isobutanol to water of greater than about 8.

* * * * *

(12) INTER PARTES REVIEW CERTIFICATE (71st)
United States Patent
Evanko et al.

(10) Number: US 8,283,505 K1
(45) Certificate Issued: Mar. 24, 2015

(54) RECOVERY OF HIGHER ALCOHOLS FROM DILUTE AQUEOUS SOLUTIONS

(75) Inventors: William A. Evanko; Aharon M. Eyal; David A. Glassner; Fudu Miao; Aristos A. Aristidou; Kent Evans; Patrick R. Gruber; Andrew C. Hawkins

(73) Assignees: Gevo, Inc.; Gevo Development, LLC; Agri-Energy, LLC

Trial Number:

IPR2013-00215 filed Mar. 26, 2013

Petitioner: Butamax Advanced Biofuels LLC

Patent Owner: Gevo, Inc.

Inter Partes Review Certificate for:

Patent No.: 8,283,505
Issued: Oct. 9, 2012
Appl. No.: 13/344,460
Filed: Jan. 5, 2012

The results of IPR2013-00215 are reflected in this inter partes review certificate under 35 U.S.C. 318(b).

INTER PARTES REVIEW CERTIFICATE
U.S. Patent 8,283,505 K1
Trial No. IPR2013-00215
Certificate Issued Mar. 24, 2015

AS A RESULT OF THE INTER PARTES REVIEW PROCEEDING, IT HAS BEEN DETERMINED THAT:

Claims 1-18 are cancelled.

\* \* \* \* \*